(12) United States Patent
Murakami et al.

(10) Patent No.: US 11,459,546 B2
(45) Date of Patent: Oct. 4, 2022

(54) METHOD FOR PRODUCING SOMATIC CELL, SOMATIC CELL, AND COMPOSITION

(71) Applicants: Kyoto Prefectural Public University Corporation, Kyoto (JP); KATAOKA CORPORATION, Kyoto (JP)

(72) Inventors: Yuta Murakami, Kanagawa (JP); Yasuhiro Yoshioka, Kanagawa (JP); Ping Dai, Kyoto (JP); Toshikazu Yoshikawa, Kyoto (JP); Yoshinori Harada, Kyoto (JP)

(73) Assignees: Kyoto Prefectural Public University Corporation, Kyoto (JP); Kataoka Corporation, Kyoto (JP)

( * ) Notice: Subject to any disclaimer, the term of this patent is extended or adjusted under 35 U.S.C. 154(b) by 490 days.

(21) Appl. No.: 16/336,985

(22) PCT Filed: Sep. 27, 2017

(86) PCT No.: PCT/JP2017/034955
§ 371 (c)(1),
(2) Date: Mar. 27, 2019

(87) PCT Pub. No.: WO2018/062269
PCT Pub. Date: Apr. 5, 2018

(65) Prior Publication Data
US 2019/0218516 A1  Jul. 18, 2019

(30) Foreign Application Priority Data

| Sep. 30, 2016 | (JP) | JP2016-193444 |
| Sep. 30, 2016 | (JP) | JP2016-193445 |
| Sep. 30, 2016 | (JP) | JP2016-193446 |
| Sep. 30, 2016 | (JP) | JP2016-193447 |
| Sep. 30, 2016 | (JP) | JP2016-193448 |
| Feb. 3, 2017 | (JP) | JP2017-018779 |

(51) Int. Cl.
*C12N 5/077* (2010.01)
*C12N 5/0793* (2010.01)

(52) U.S. Cl.
CPC ......... *C12N 5/0653* (2013.01); *C12N 5/0619* (2013.01); *C12N 5/0654* (2013.01); *C12N 5/0655* (2013.01); *C12N 5/0657* (2013.01); *C12N 2501/148* (2013.01); *C12N 2501/39* (2013.01); *C12N 2501/727* (2013.01); *C12N 2501/999* (2013.01); *C12N 2506/1307* (2013.01)

(58) Field of Classification Search
CPC .............. C12N 5/0653; C12N 2501/999
See application file for complete search history.

(56) References Cited

U.S. PATENT DOCUMENTS

| 10,087,416 B2 | 10/2018 | Chan et al. |
| 2011/0117066 A1 | 5/2011 | Ailhaud et al. |
| 2012/0276063 A1 | 11/2012 | Meyer et al. |
| 2015/0004144 A1 | 1/2015 | Cowan et al. |
| 2018/0080009 A1 | 3/2018 | Okano et al. |

FOREIGN PATENT DOCUMENTS

| JP | 2017-104091 A | 6/2017 |
| WO | 2016/086092 A1 | 6/2016 |

OTHER PUBLICATIONS

Remst (Cell Tissue Res, 2014,355:163-171).*
Xu (Molecular Psychiatry, 2016, 21:62-70; published online Jul. 28, 2015).*
Madhu (2016, Stem Cells International, Article 1035374, pp. 1-13).*
Grath, 2019, Journal of Biological Engineering, 13: pp. 1-15.*
Grotheer, 2021, Scientific Reports, 11:11968, 17 pages.*
Takeda,, 2018, Bioscience Reports, 38:BSER20171650, pp. 1-19.*
Miwako Nishio et al., "Production of Functional Classical Brown Adipocytes from Human Pluripotent Stem Cells using Specific Hemopoietin Cocktail without Gene Transfer", Cell Metabolism, vol. 16, pp. 394-406 (Sep. 5, 2012), Elsevier Inc.
Haixia Wang et al., "Small molecules enable cardiac reprogramming of mouse fibroblasts with a single factor, Oct4", Cell Rep., vol. 6, Issue 5, pp. 951-960 (Mar. 13, 2014), doi: 10.1016/j.celrep.2014.01.038.
The International Bureau of WIPO, "International Preliminary Report on Patentability," issued in International Application No. PCT/JP2017/034955, of which U.S. Appl. No. 16/336,985 is a U.S. national phase entry, dated Apr. 2, 2019, 41 pages.
Ping Dai et al., "Highly efficient direct conversion of human fibroblasts to neuronal cells by chemical compounds," Journal of Clinical Biochemistry and Nutrition, vol. 56, No. 3, pp. 166-170 (May 2015).
Hirofumi Yoshida et al., "Regulation of brown adipogenesis by the Tgf-β family: Involvement of Srebp1c in Tgf-β- and Activin-induced inhibition of adipogenesis," Biochimica et Biophysica Acta, vol. 1830, pp. 5027-5035, 2013, Elsevier B.V.

\* cited by examiner

*Primary Examiner* — Valarie E Bertoglio

(57) ABSTRACT

The present invention addresses the problem of providing: a method for producing brown adipocytes, osteoblasts, cartilage cells, neural cells, or cardiac cells from somatic cells without performing artificial gene transfer; brown adipocytes, osteoblasts, cartilage cells, neural cells, or cardiac cells; or a composition including a combination of chemical substances that can be used for the aforementioned production method. An example of the present invention is a method for producing brown adipocytes, osteoblasts, cartilage cells, neural cells, or cardiac cells including a step for culturing somatic cells in the presence or absence of an inhibitor or activator selected from the group consisting of an ALK5 inhibitor, an ALK6 inhibitor, an AMPK inhibitor, a cAMP activator, an ALK2 inhibitor, an ALK3 inhibitor, a GSK3 inhibitor, and an Erk inhibitor.

9 Claims, 15 Drawing Sheets

Specification includes a Sequence Listing.

[Figure 1]
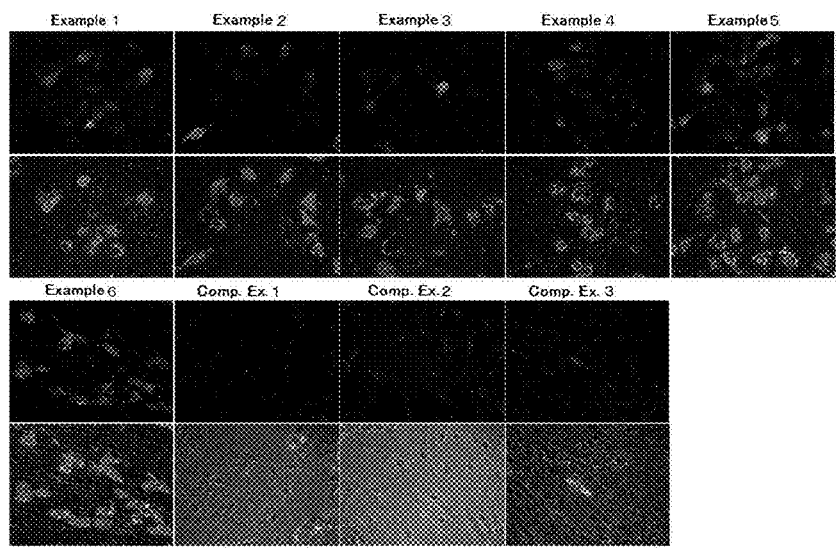
[Figure 2]
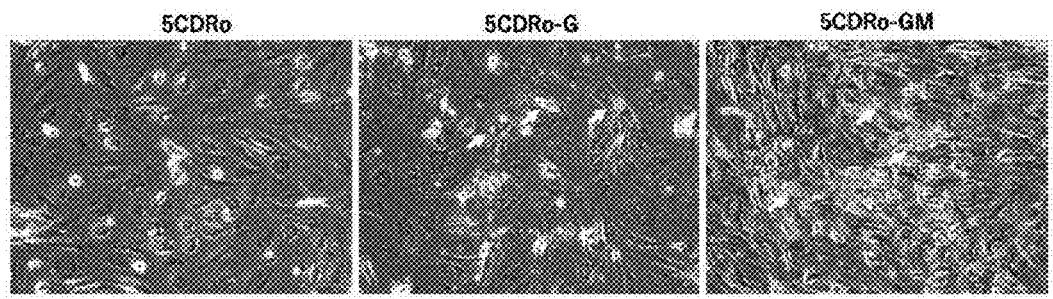
[Figure 3]
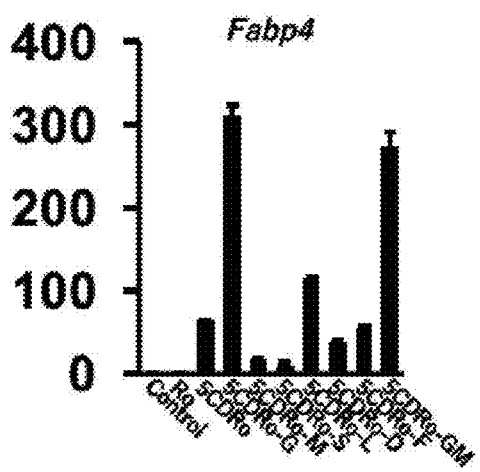

[Figure 4]
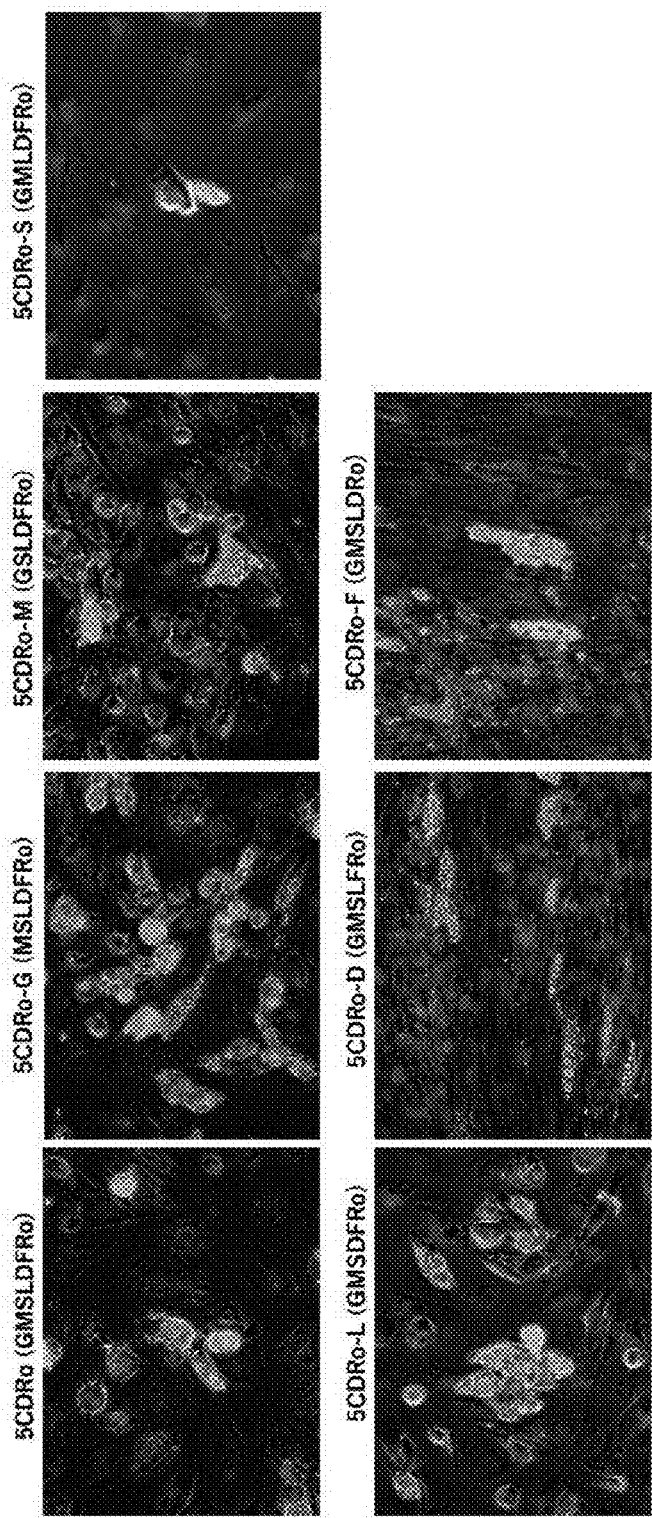

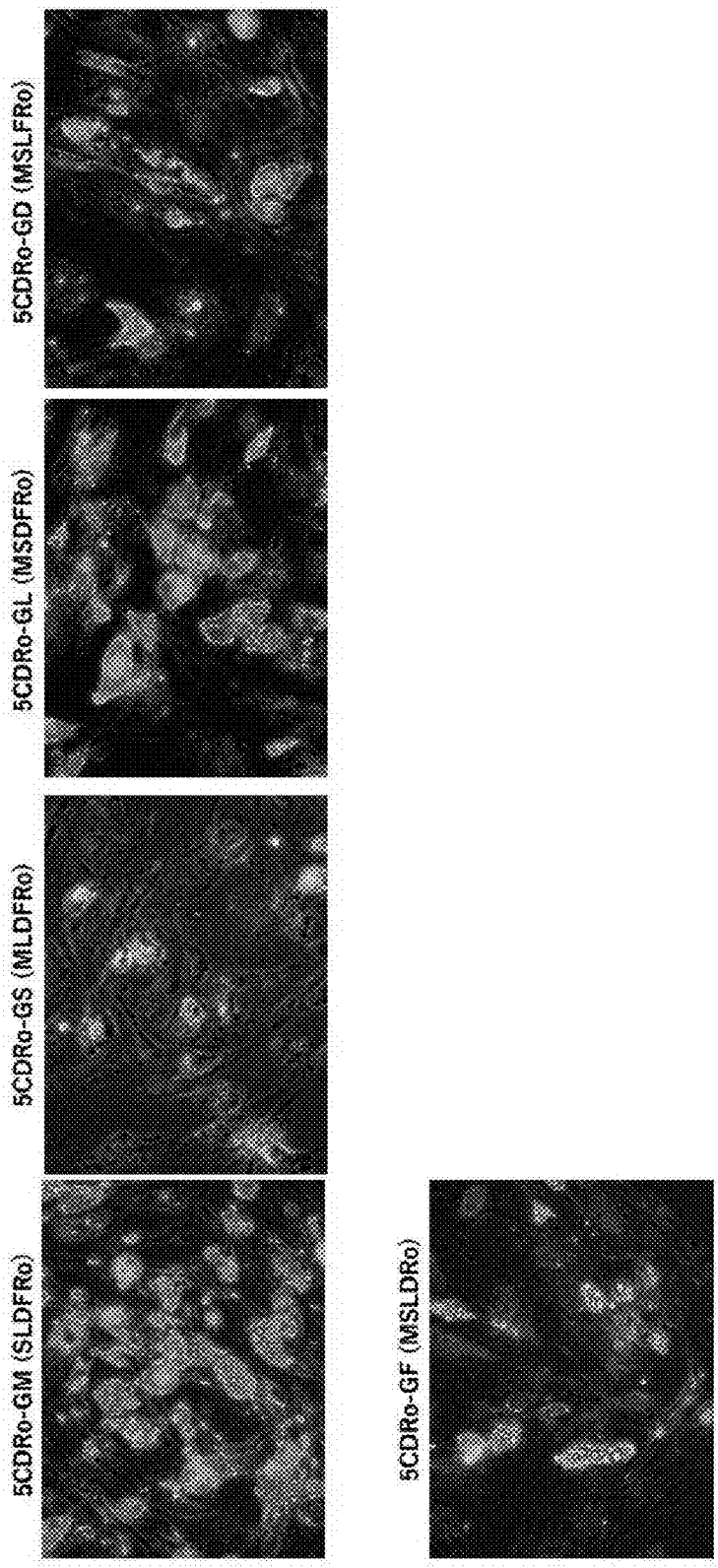
[Figure 5]

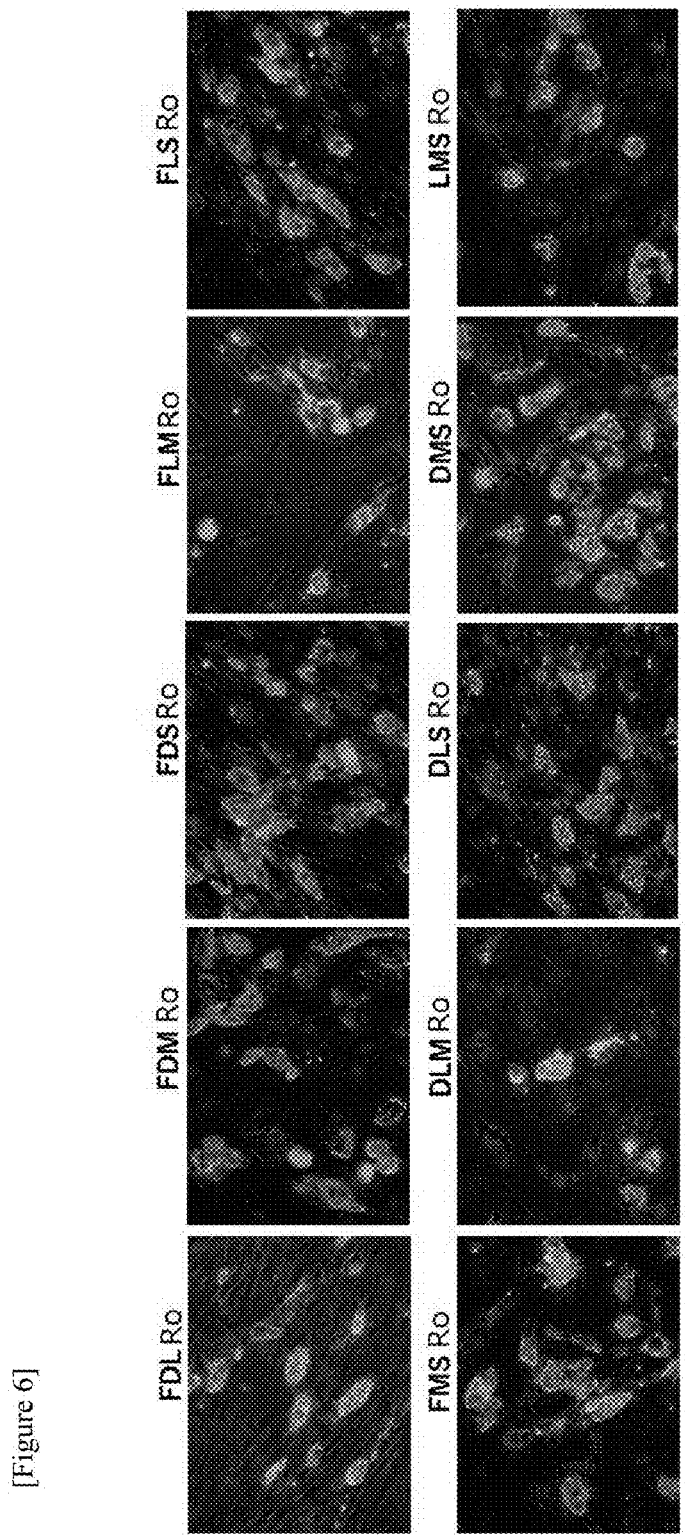
[Figure 6]

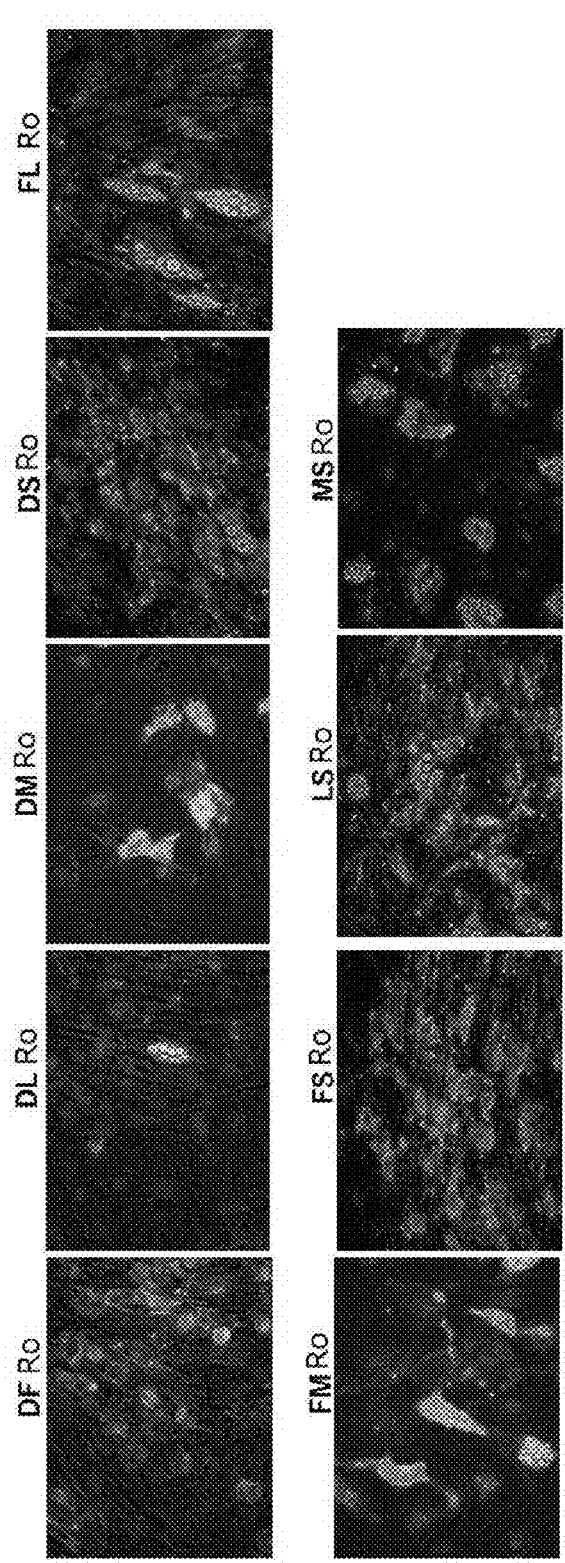
[Figure 7]

[Figure 8]
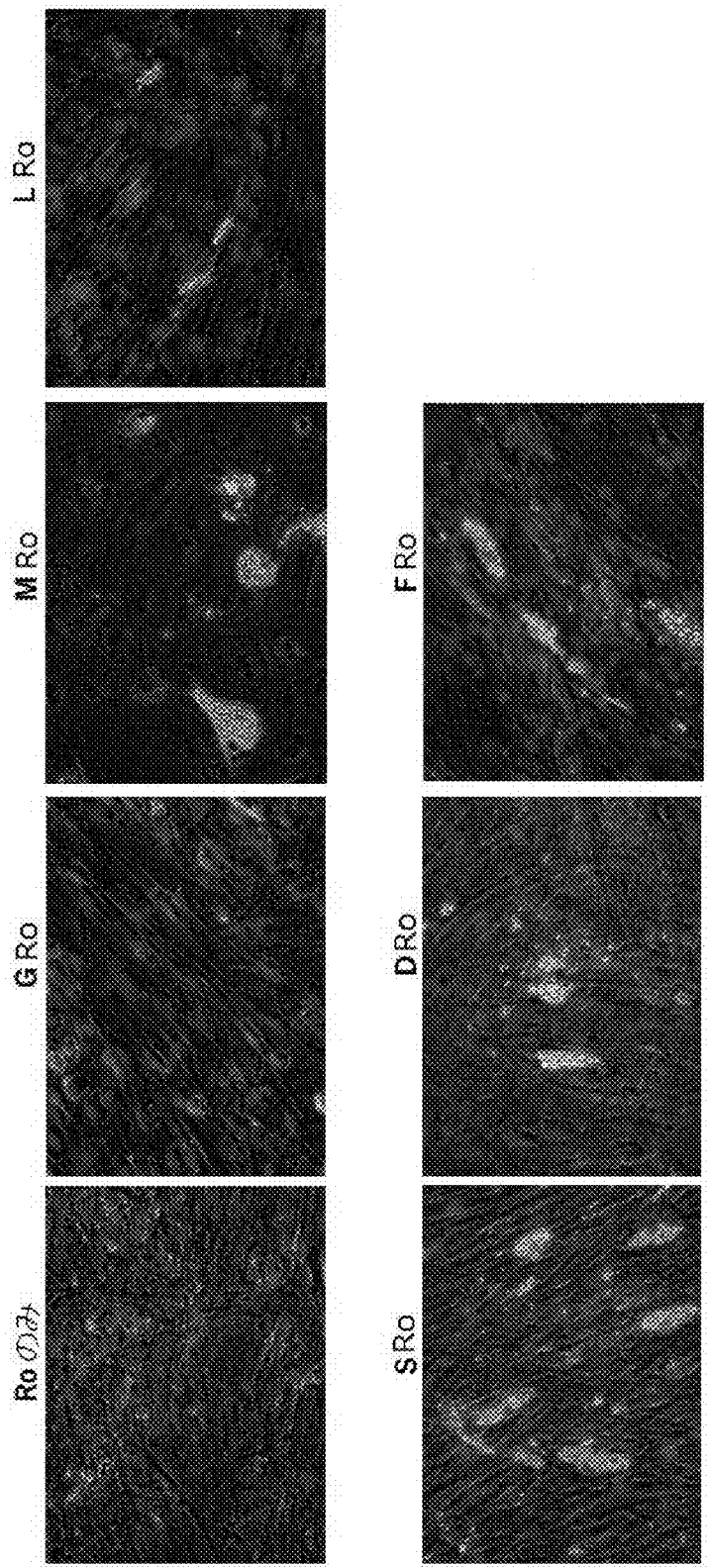

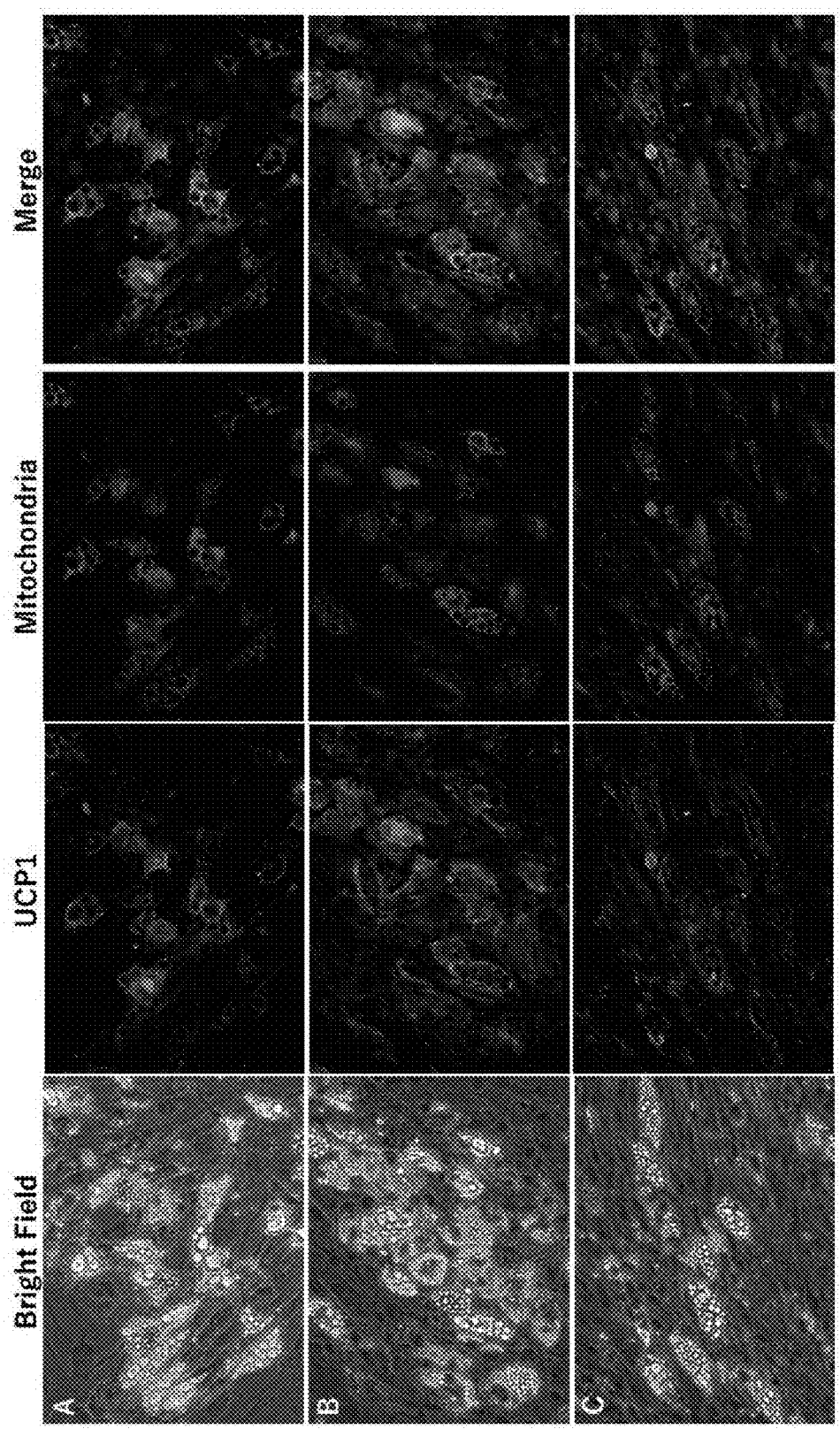
[Figure 9]

[Figure 10]
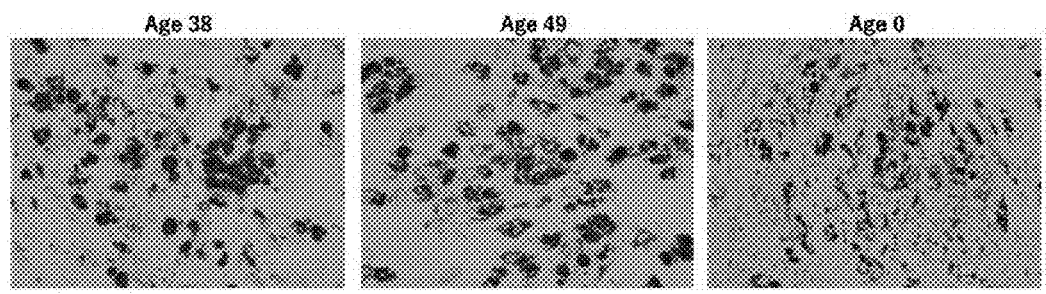

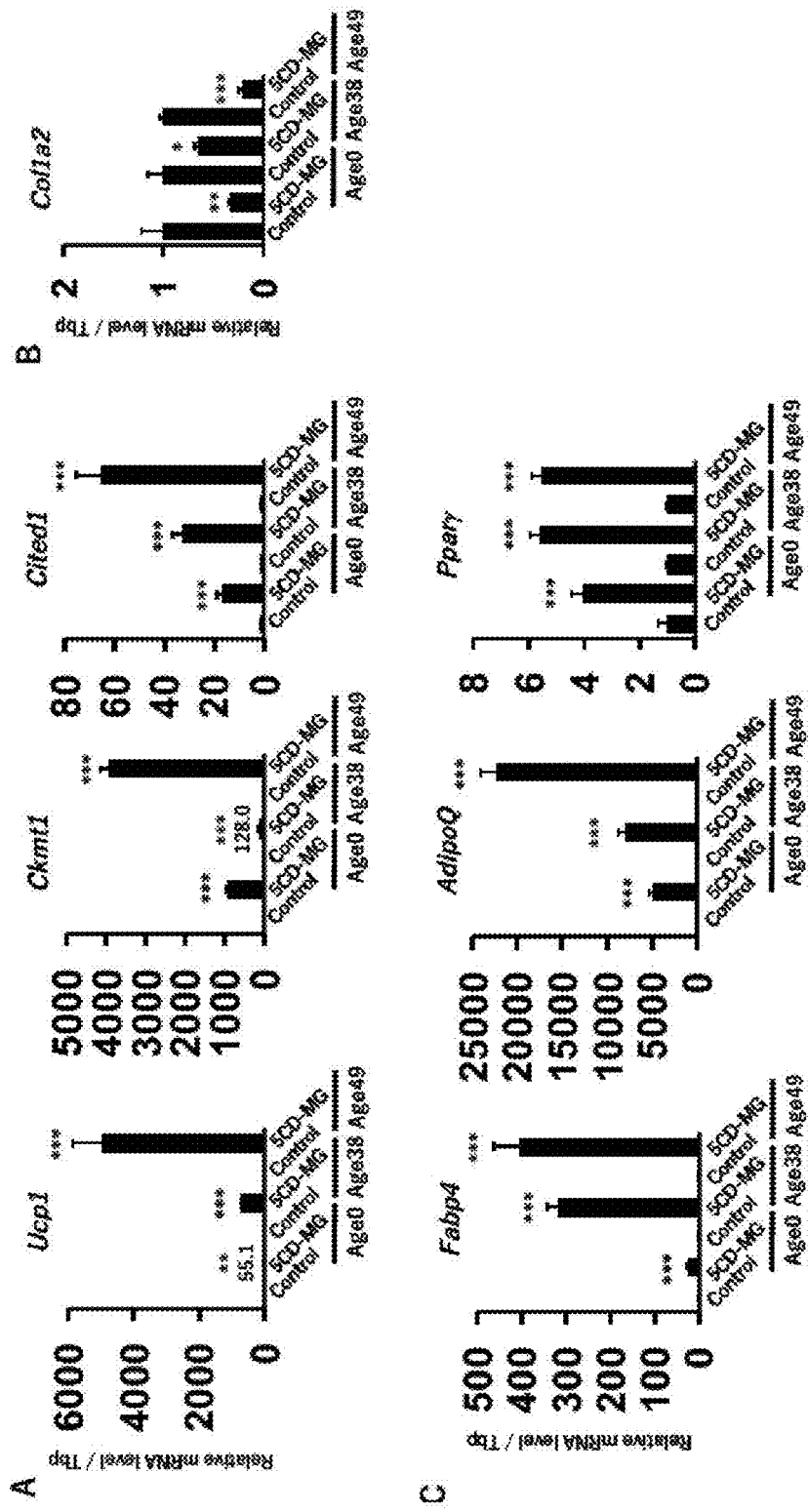
[Figure 11]

[Figure 12]
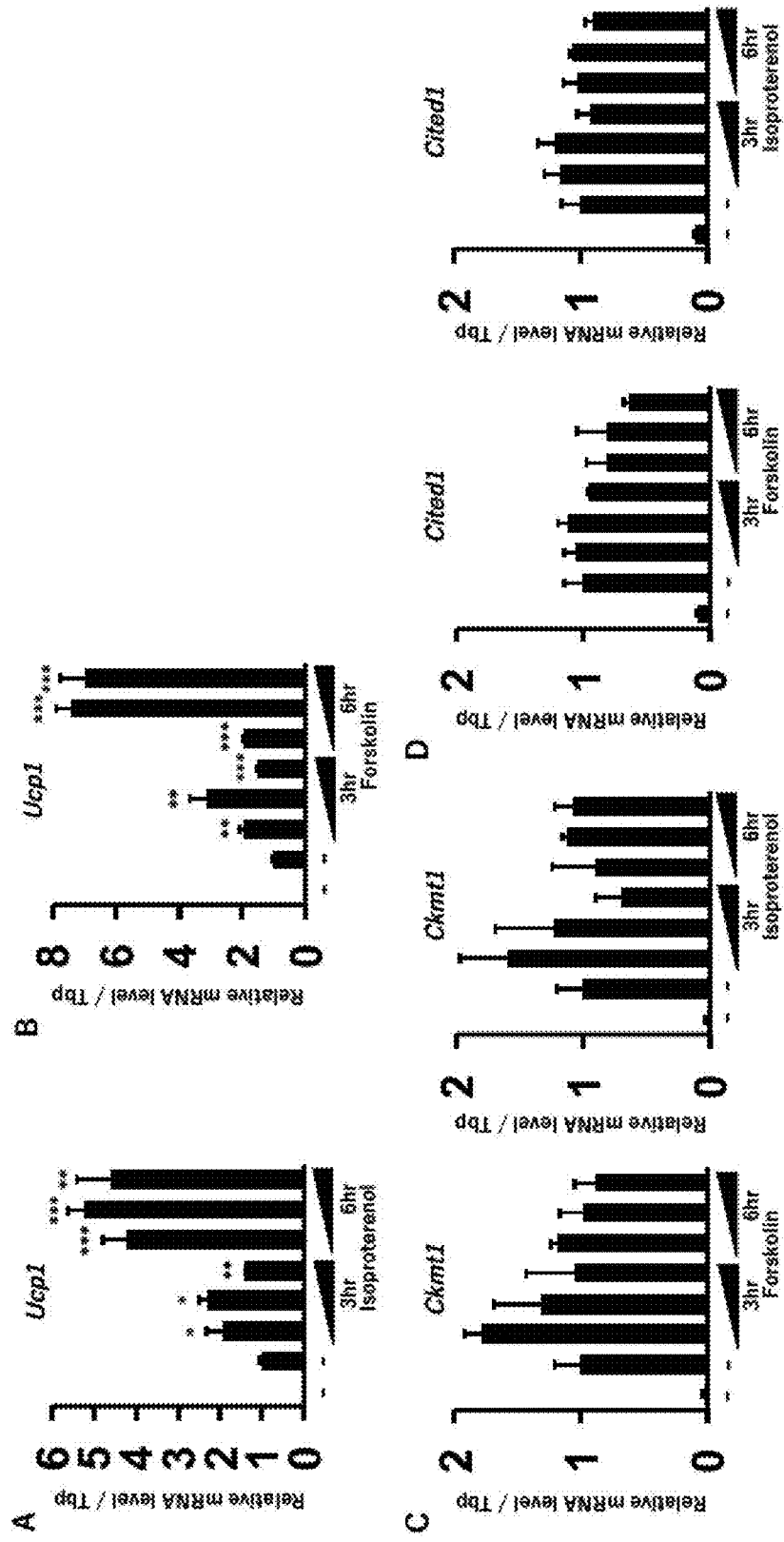

[Figure 13]
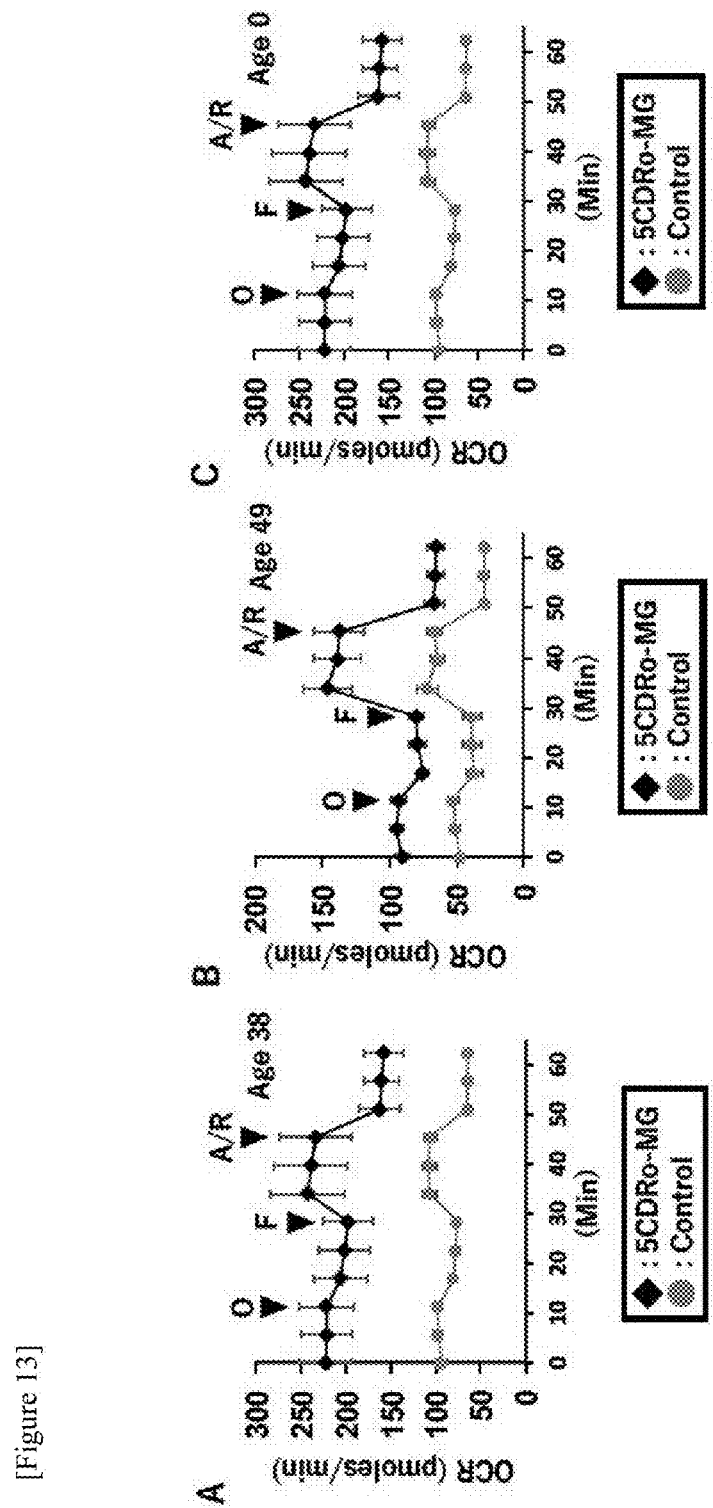

[Figure 14]
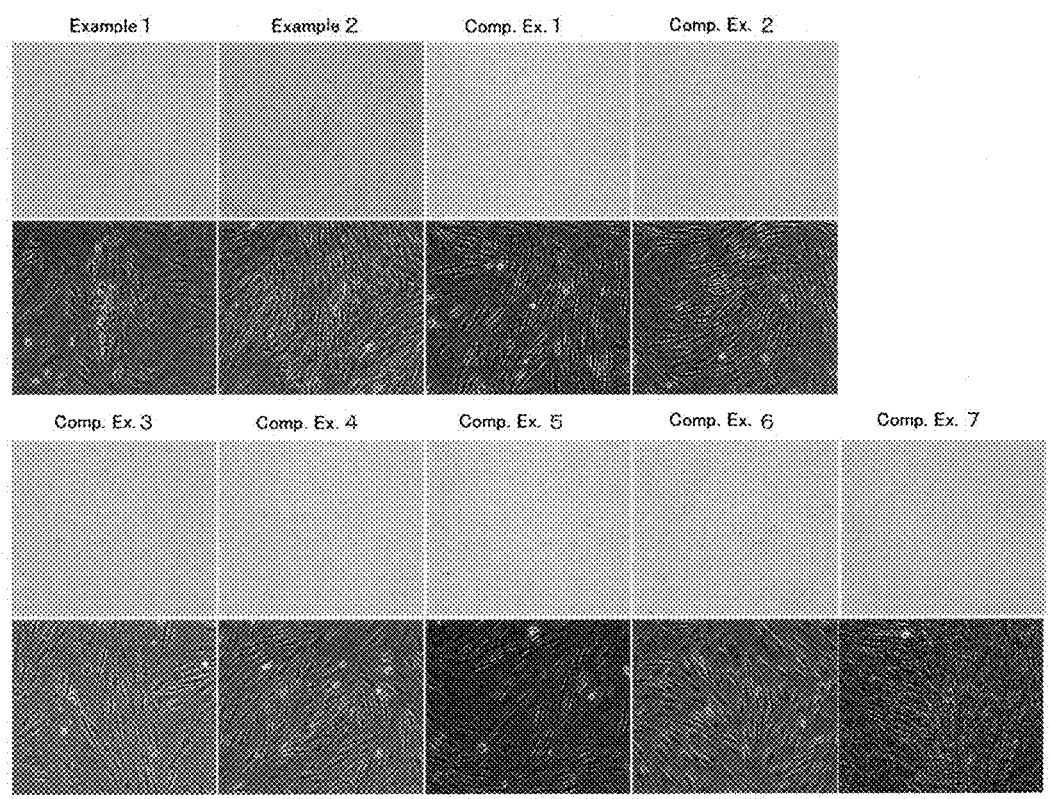

[Figure 15]
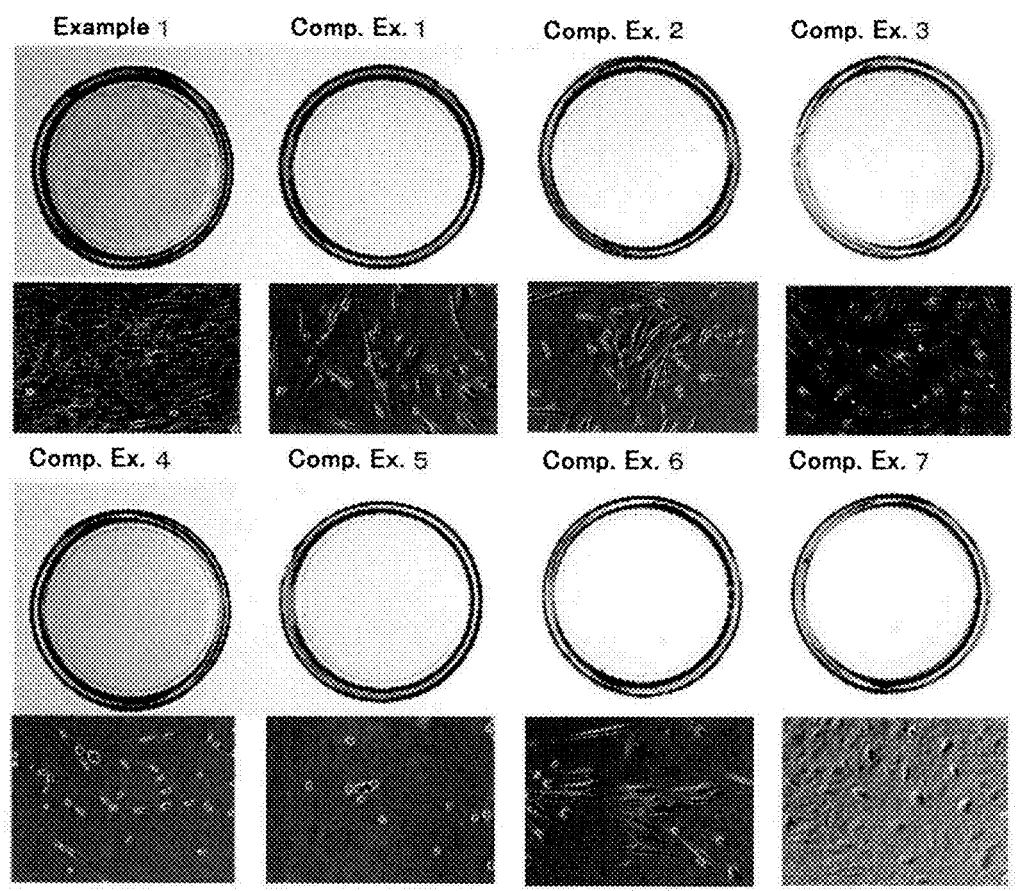

[Figure 16]
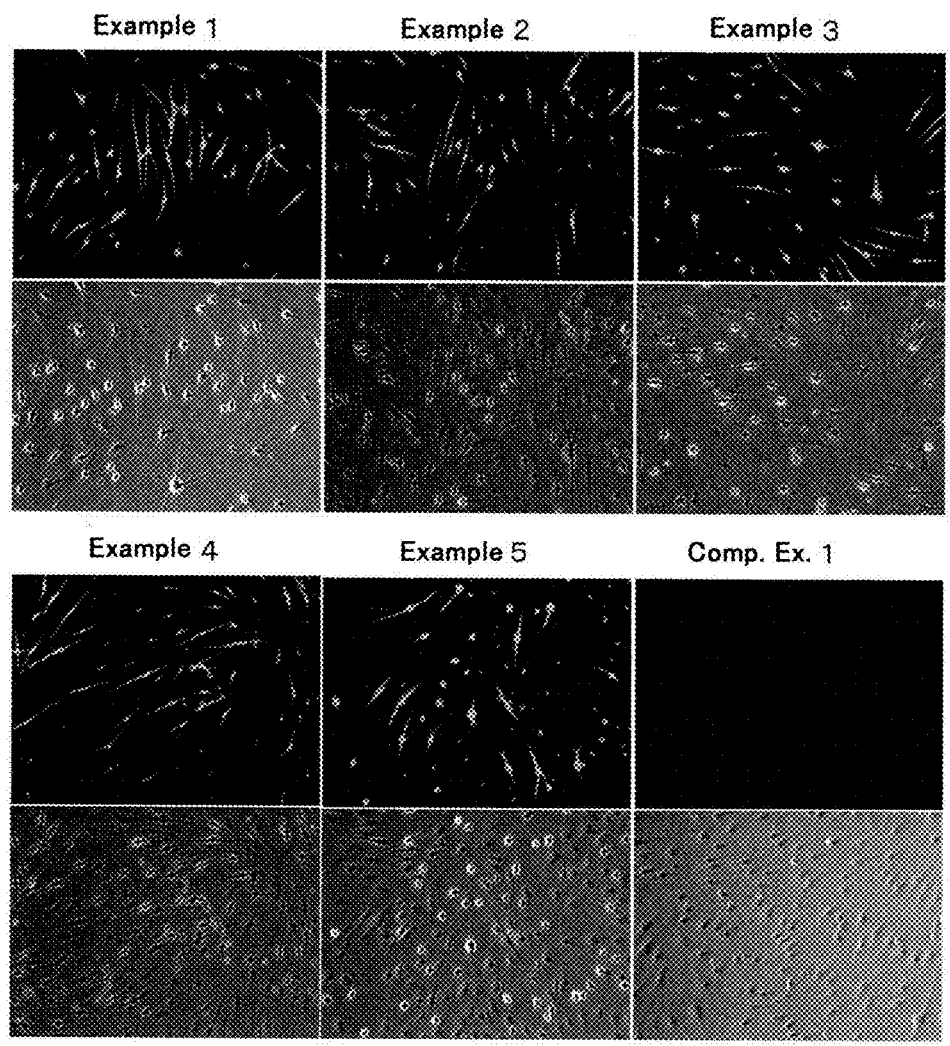

[Figure 17]
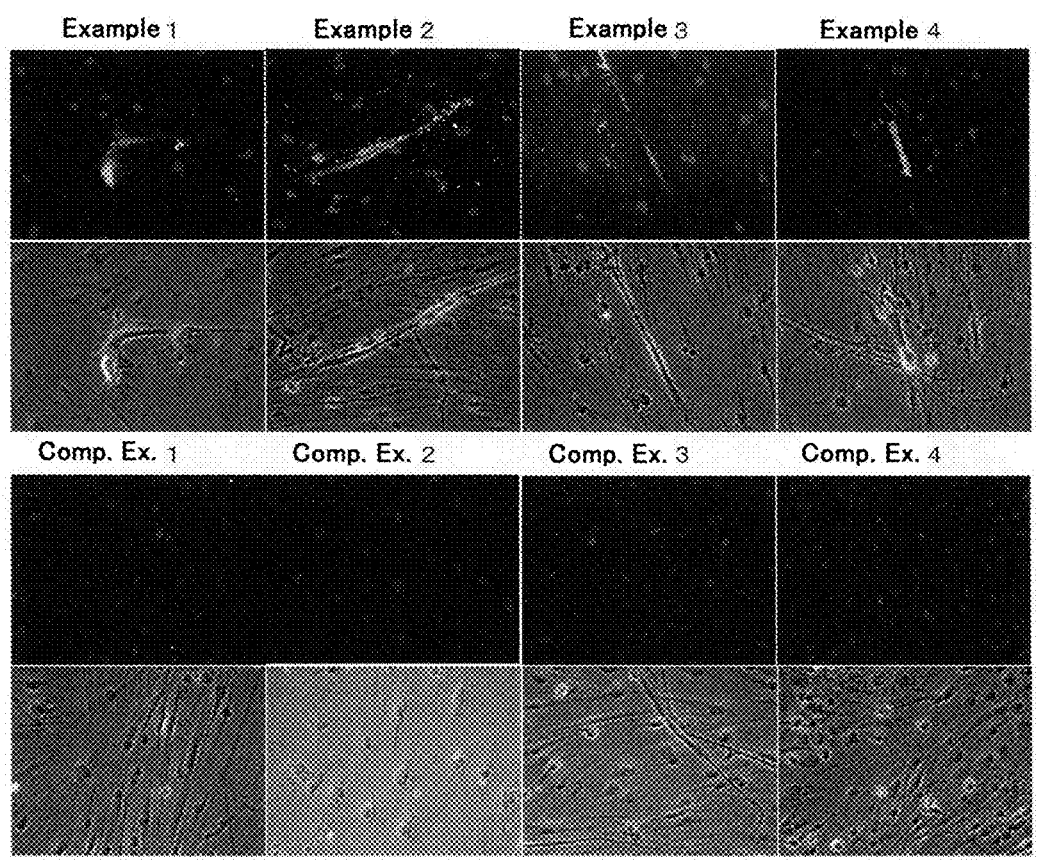

METHOD FOR PRODUCING SOMATIC CELL, SOMATIC CELL, AND COMPOSITION

CROSS REFERENCE TO RELATED APPLICATIONS

This patent application is a U.S. national stage application under 35 U.S.C. § 371 of International Patent Application No. PCT/JP2017/034955 filed on Sep. 27, 2017, which claims the benefit of foreign priority to: Japanese Patent Application No. JP 2016-193444 filed on Sep. 30, 2016; Japanese Patent Application No. JP 2016-193445 filed on Sep. 30, 2016; Japanese Patent Application No. JP 2016-193446 filed on Sep. 30, 2016; Japanese Patent Application No. JP 2016-193447 filed on Sep. 30, 2016: Japanese Patent Application No. JP 2016-193448 filed on Sep. 30, 2016: and Japanese Patent Application No. JP 2017-018779 filed on Feb. 3, 2017. The International Application was published in Japanese on Apr. 5, 2018, as International Publication No. WO 2018/062269 A1 under PCT Article 21(2).

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

The sequence listings disclosed in the ASCII text file submitted herewith, named "seqlist.txt" and created on Mar. 18, 2019, the size of which is 3,570 bytes, are hereby incorporated by reference.

FIELD OF THE INVENTION

The present invention relates to a method for producing somatic cells. The present invention further relates to the somatic cells, and a composition usable for the method for producing the somatic cells.

Specifically, the somatic cells produced by the production method according to the present invention refers to brown adipocytes, osteoblasts, chondrocytes, neural cells, or cardiomyocytes.

BACKGROUND ART

Thanks to the recent advance in cell-related studies, especially pluripotent cell-related studies, therapeutic cells are becoming available in qualities and amounts usable for transplantation into individuals. For some diseases, an attempt to transplant a therapeutically effective cell into a patient has started.

Mesenchymal cells constitute various organs in a living body, such as muscle, bone, cartilage, bone marrow, adipose tissue and connective tissue, and are promising materials for regenerative medicine. Mesenchymal stem cells (MSC) are undifferentiated cells present in tissues such as bone marrow, adipose tissue, blood, placenta and umbilical cord. Since the mesenchymal stem cells have the ability to differentiate into cells belonging to the mesenchymal system, the mesenchymal stem cells are attracting attention as starting materials in producing the mesenchymal cells. Also, a regenerative medicine in which the mesenchymal stem cells themselves are utilized for reconstruction of bone, cartilage, cardiac muscle or the like is studied.

Meanwhile, a method for directly transforming a somatic cell such as a fibroblast into another cell has also been reported. For example, it is known that a nerve cell is obtained by culturing a fibroblast together with a chemical substance (Non-Patent Document 1).

PRIOR ART LITERATURES

Patent Literature

Non-Patent Document 1: Journal of Clinical Biochemistry and Nutrition, 2015, Vol. 56, No. 3, pp. 166-170

SUMMARY OF THE INVENTION

Problem to be Solved by the Invention

Similarly to the method described in Non-Patent Document 1, a method for transforming a somatic cell into a desired cell without gene transfer may be an effective option as a means of acquiring a therapeutic cell. A main problem of the present invention to be solved is to provide a method for producing brown adipocytes, osteoblasts, chondrocytes, neural cells or cardiomyocytes from somatic cells without artificial gene transfer; brown adipocytes, osteoblasts, chondrocytes, neural cells or cardiomyocytes; or a composition containing a combination of chemical substances, usable for the production method.

Means for Solving Problem

As a result of intensive studies to solve the above problems, the present inventors have found that somatic cells can be transformed into brown adipocytes, osteoblasts, chondrocytes, neural cells, or cardiomyocytes by culturing the somatic cells in the presence or absence of a certain inhibitor or activator. The present invention has been accomplished based on this finding.

The prevent invention includes the followings, for example.

[1] A method of producing brown adipocytes, comprising a step a) of culturing a somatic cell in the presence of an ALK5 inhibitor and in the presence of at least one inhibitor selected from a group consisting of an ALK6 inhibitor and an AMPK inhibitor.

[2] The method of producing brown adipocytes according to the above [1], wherein the step a) is a step of culturing the somatic cell in the presence of the ALK6 inhibitor and the AMPK inhibitor.

[3] The method of producing brown adipocytes according to the above [1] or [2], wherein the step a) is a step of culturing the somatic cell in the presence of at least one activator and/or inhibitor selected from a group consisting of a cAMP activator, an ALK2 inhibitor, an ALK3 inhibitor, a GSK3 inhibitor, and an Erk inhibitor.

[4] The method of producing brown adipocytes according to any one of the above [1]-[3], wherein the step a) is a step of culturing the somatic cell in the presence of any of the followings:

(1) the ALK5 inhibitor, the ALK6 inhibitor, the AMPK inhibitor, the cAMP activator, the ALK2 inhibitor, the ALK3 inhibitor, the GSK3 inhibitor, and the Erk inhibitor;

(2) the ALK5 inhibitor, the ALK6 inhibitor, the AMPK inhibitor, the cAMP activator, the ALK2 inhibitor, and the ALK3 inhibitor;

(3) the ALK5 inhibitor, the ALK6 inhibitor, the AMPK inhibitor, the ALK2 inhibitor, the ALK3 inhibitor, the GSK3 inhibitor, and the Erk inhibitor;

(4) the ALK5 inhibitor, the ALK6 inhibitor, the AMPK inhibitor, the cAMP activator, the ALK2 inhibitor, the ALK3 inhibitor, and the Erk inhibitor;

(5) the ALK5 inhibitor, the ALK6 inhibitor, the AMPK inhibitor, the cAMP activator, the ALK2 inhibitor, the ALK3 inhibitor, and the GSK3 inhibitor:

(6) the ALK5 inhibitor, the ALK6 inhibitor, the AMPK inhibitor, the ALK2 inhibitor, and the ALK3 inhibitor.

[5] The method of producing brown adipocytes according to any one of the above [1]-[4], wherein the culturing the somatic cell in the presence of the at least one inhibitor selected from the group consisting of the ALK6 inhibitor and the AMPK inhibitor comprises culturing the somatic cell in the presence of dorsomorphin.

[6] The method of producing brown adipocytes according to the above [3] or [4], wherein the culturing the somatic cell in the presence of the at least one inhibitor selected from the group consisting of the ALK2 inhibitor and the ALK3 inhibitor comprises culturing the somatic cell in the presence of LDN193189 and/or dorsomorphin.

[7] The method of producing brown adipocytes according to any one of the above [1]-[6], wherein the step a) is a step of culturing the somatic cell in the presence of a p53 inhibitor.

[8] The method of producing brown adipocytes according to any one of the above [1]-[7], wherein the step a) is a step of culturing the somatic cell in the absence of components acting on histone

[9] The method of producing brown adipocytes according to any one of the above [1]-[8], wherein the somatic cell is fibroblast.

[10] A brown adipocyte produced by the method of producing brown adipocytes according to any one of the above [1]-[9].

[11] A composition containing at least one inhibitor selected from a group consisting of an ALK5 inhibitor, an ALK6 inhibitor, and an AMPK inhibitor.

[12] The composition according to the above [11], containing the ALK6 inhibitor and the AMPK inhibitor.

[13] The composition according to the above [11] or [12], further containing at least one activator and/or inhibitor selected from a group consisting of a cAMP activator, an ALK2 inhibitor, an ALK3 inhibitor, a GSK3 inhibitor, and an Erk inhibitor.

[14] The composition according to any one of the above [11]-[13], containing any of the following combinations:

(1) the ALK5 inhibitor, the ALK6 inhibitor, the AMPK inhibitor, the cAMP activator, the ALK2 inhibitor, the ALK3 inhibitor, the GSK3 inhibitor, and the Erk inhibitor;

(2) the ALK5 inhibitor, the ALK6 inhibitor, the AMPK inhibitor, the cAMP activator, the ALK2 inhibitor, and the ALK3 inhibitor;

(3) the ALK5 inhibitor, the ALK6 inhibitor, the AMPK inhibitor, the ALK2 inhibitor, the ALK3 inhibitor, the GSK3 inhibitor, and the Erk inhibitor;

(4) the ALK5 inhibitor, the ALK6 inhibitor, the AMPK inhibitor, the cAMP activator, the ALK2 inhibitor, the ALK3 inhibitor, and the Erk inhibitor;

(5) the ALK5 inhibitor, the ALK6 inhibitor, the AMPK inhibitor, the cAMP activator, the ALK2 inhibitor, the ALK3 inhibitor, and the GSK3 inhibitor;

(6) the ALK5 inhibitor, the ALK6 inhibitor, the AMPK inhibitor, the ALK2 inhibitor, and the ALK3 inhibitor.

[15] The composition according to any one of the above [11]-[14], wherein the at least one inhibitor selected from the group consisting of the ALK6 inhibitor and the AMPK inhibitor is dorsomorphin.

[16] The composition according to the above [13] or [14], wherein the at least one inhibitor selected from the group consisting of the ALK2 inhibitor and the ALK3 inhibitor is LDN193189 and/or dorsomorphin.

[17] The composition according to any one of the above [11]-[16], wherein the composition is for producing brown adipocytes from a somatic cell.

[18] A method of producing brown adipocytes, comprising a step b) of culturing a somatic cell in the presence of at least one group selected from five groups consisting of: (1) an Erk inhibitor; (2) an ALK2 inhibitor and an ALK3 inhibitor; (3) an ALK5 inhibitor; (4) an ALK6 inhibitor, an AMPK inhibitor, the ALK2 inhibitor, and the ALK3 inhibitor; and (5) a cAMP activator.

[19] The method of producing brown adipocytes according to the above [18], wherein the step b) is a step of culturing the somatic cell in the presence of at least two groups selected from five groups consisting of: (1) the Erk inhibitor; (2) the ALK2 inhibitor and the ALK3 inhibitor; (3) the ALK5 inhibitor; (4) the ALK6 inhibitor, the AMPK inhibitor, the ALK2 inhibitor and the ALK3 inhibitor; and (5) the cAMP activator.

[20] The method of producing brown adipocytes according to the above [18] or [19], wherein the step b) is a step of culturing the somatic cell in the presence of any of the followings:

(i) the ALK6 inhibitor, the AMPK inhibitor, the ALK2 inhibitor, and the ALK3 inhibitor, as well as the cAMP activator;

(ii) the ALK6 inhibitor, the AMPK inhibitor, the ALK2 inhibitor, and the ALK3 inhibitor, as well as the Erk inhibitor;

(iii) the ALK6 inhibitor, the AMPK inhibitor, the ALK2 inhibitor, and the ALK3 inhibitor, as well as the ALK5 inhibitor;

(iv) the cAMP activator, as well as the ALK2 inhibitor and the ALK3 inhibitor;

(v) the cAMP activator, as well as the Erk inhibitor (vi) the cAMP activator, as well as the ALK5 inhibitor;

(vii) the ALK2 inhibitor, and the ALK3 inhibitor, as well as the ALK5 inhibitor; and (viii) the Erk inhibitor, as well as the ALK5 inhibitor.

[21] The method of producing brown adipocytes according to the above [18] or [19], wherein the step b) is a step of culturing the somatic cell in the presence of at least three groups selected from five groups consisting of: (1) the Erk inhibitor; (2) the ALK2 inhibitor and the ALK3 inhibitor; (3) the ALK5 inhibitor; (4) the ALK6 inhibitor, the AMPK inhibitor, the ALK2 inhibitor, and the ALK3 inhibitor; and (5) the cAMP activator.

[22] The method of producing brown adipocytes according to any one of the above [18], [19] and [21], wherein the step b) is a step of culturing the somatic cell in the presence of at least four groups selected from five groups consisting of: (1) the Erk inhibitor; (2) the ALK2 inhibitor and the ALK3 inhibitor; (3) the ALK5 inhibitor; (4) the ALK6 inhibitor; the AMPK inhibitor, the ALK2 inhibitor, and the ALK3 inhibitor; and (5) the cAMP activator.

[23] A method of producing brown adipocytes, comprising a step b) of culturing a somatic cell in the presence of at least five groups selected from six groups consisting of: (1) an Erk inhibitor; (2) an ALK2 inhibitor and an ALK3 inhibitor; (3) an ALK5 inhibitor; (4) an ALK6 inhibitor, an AMPK inhibitor, the ALK2 inhibitor, and the ALK3 inhibitor; (5) a cAMP activator; and (6) a GSK3 inhibitor.

[24] The method of producing brown adipocytes according to any one of the above [18]-[23], wherein the culturing the somatic cell in the presence of the ALK6 inhibitor, the AMPK inhibitor, the ALK2 inhibitor, and the ALK3 inhibitor comprises culturing the somatic cell in the presence of dorsomorphin or in the presence of dorsomorphin and LDN193189. [25] The method of producing brown adipocytes according to any one of the above [18]-[24], wherein the step b) is a step of culturing the somatic cell in the absence of a p53 inhibitor.

[26] The method of producing brown adipocytes according to any one of the above [18]-[25], wherein the step b) is a step of culturing the somatic cell in the absence of components acting on histone.

[27] The method of producing brown adipocytes according to any one of the above [18]-[26], wherein the somatic cell is fibroblast.

[28] A brown adipocyte produced by the method of producing brown adipocytes according to any one of the above [18]-[27].

[29] A composition for producing brown adipocytes from a somatic cell, containing any one group selected from five groups consisting of: (1) an Erk inhibitor; (2) an ALK2 inhibitor and an ALK3 inhibitor; (3) an ALK5 inhibitor; (4) an ALK6 inhibitor, an AMPK inhibitor, the ALK2 inhibitor, and the ALK3 inhibitor; and (5) a cAMP activator.

[30] The composition for producing brown adipocytes from the somatic cell according to the above [29], containing at least two groups selected from five groups consisting of: (1) the Erk inhibitor; (2) the ALK2 inhibitor and the ALK3 inhibitor; (3) the ALK5 inhibitor; (4) the ALK6 inhibitor, the AMPK inhibitor, the ALK2 inhibitor and the ALK3 inhibitor; and (5) the cAMP activator.

[31] The composition for producing brown adipocytes from the somatic cell according to the above [29] or [30], containing any of the followings:
 (i) the ALK6 inhibitor, the AMPK inhibitor, the ALK2 inhibitor, and the ALK3 inhibitor, as well as the cAMP activator;
 (ii) the ALK6 inhibitor, the AMPK inhibitor, the ALK2 inhibitor, and the ALK3 inhibitor, as well as the Erk inhibitor;
 (iii) the ALK6 inhibitor, the AMPK inhibitor, the ALK2 inhibitor, and the ALK3 inhibitor, as well as the ALK5 inhibitor;
 (iv) the cAMP activator, as well as the ALK2 inhibitor and the ALK3 inhibitor;
 (v) the cAMP activator, as well as the Erk inhibitor
 (vi) the cAMP activator, as well as the ALK5 inhibitor;
 (vii) the ALK2 inhibitor, and the ALK3 inhibitor, as well as the ALK5 inhibitor; and
 (viii) the Erk inhibitor, as well as the ALK5 inhibitor.

[32] The composition for producing brown adipocytes from the somatic cell according to the above [29] or [30], containing at least three groups selected from five groups consisting of: (1) the Erk inhibitor; (2) the ALK2 inhibitor, the ALK3 inhibitor; (3) ALK5 inhibitor; (4) ALK6 inhibitor, the AMPK inhibitor, the ALK2 inhibitor, and the ALK3 inhibitor; and (5) the cAMP activator.

[33] The composition for producing brown adipocytes from the somatic cell according to any one of the above [29], [30] and [32], containing at least four groups selected from five groups consisting of: (1) the Erk inhibitor; (2) the ALK2 inhibitor and the ALK3 inhibitor; (3) the ALK5 inhibitor; (4) the ALK6 inhibitor; the AMPK inhibitor, the ALK2 inhibitor, and the ALK3 inhibitor; and (5) the cAMP activator.

[34] A composition for producing brown adipocytes from a somatic cell, containing at least five groups selected from six groups consisting of: (1) an Erk inhibitor; (2) an ALK2 inhibitor and an ALK3 inhibitor; (3) an ALK5 inhibitor; (4) an ALK6 inhibitor, an AMPK inhibitor, the ALK2 inhibitor, and the ALK3 inhibitor; (5) a cAMP activator; and (6) a GSK3 inhibitor.

[35] The composition for producing brown adipocytes from the somatic cell according to any one of the above [29]-[34], wherein the ALK6 inhibitor, the AMPK inhibitor, the ALK2 inhibitor, and the ALK3 inhibitor are dorsomorphin or in the presence of dorsomorphin and LDN193189.

[36] A method of producing osteoblasts, comprising a step c) of culturing a somatic cell in the presence of at least one inhibitor selected from a group consisting of an ALK5 inhibitor, a GSK3 inhibitor, an ALK2 inhibitor, and an ALK3 inhibitor, in the presence of a cAMP activator, and in the absence of an Erk inhibitor.

[37] The method of producing osteoblasts according to the above [36], wherein the step c) is a step of culturing the somatic cell in the presence of the ALK2 inhibitor and the ALK3 inhibitor.

[38] The method of producing osteoblasts according to the above [36] or [37], wherein the step c) is a step of culturing the somatic cell in the presence of at least one inhibitor selected from a group consisting of an ALK6 inhibitor and an AMPK inhibitor.

[39] The method of producing osteoblasts according to any one of the above [36]-[38], wherein the step c) is a step of culturing the somatic cell in the presence of any of the followings:
 (1) the ALK5 inhibitor, the GSK3 inhibitor, the ALK2 inhibitor, the ALK3 inhibitor, the ALK6 inhibitor, the AMPK inhibitor, and the cAMP activator, and in the absence of the Erk inhibitor;
 (2) the ALK5 inhibitor, the GSK3 inhibitor, the ALK2 inhibitor, the ALK3 inhibitor, and the cAMP activator, and in the absence of the Erk inhibitor.

[40] The method of producing osteoblasts according to the above [37] or [39], wherein the culturing the somatic cell in the presence of the ALK2 inhibitor and the ALK3 inhibitor comprises culturing the somatic cell in the presence of LDN193189 and/or dorsomorphin.

[41] The method of producing osteoblasts according to the above [38], wherein the culturing the somatic cell in the presence of the at least one inhibitor selected from the group consisting of the ALK6 inhibitor and the AMPK inhibitor comprises culturing the somatic cell in the presence of dorsomorphin.

[42] The method of producing osteoblasts according to any one of the above [36]-[41], wherein the step c) is a step of culturing the somatic cell in the absence of a p53 inhibitor.

[43] The method of producing osteoblasts according to any one of the above [36]-[42], wherein the step c) is a step of culturing the somatic cell in the absence of growth factors and/or cytokines.

[44] The method of producing osteoblasts according to any one of the above [36]-[43], wherein the step c) is a step of culturing the somatic cell in the absence of components acting on histone.

[45] The method of producing osteoblasts according to any one of the above [36]-[44], wherein the somatic cell is fibroblast

[46] An osteoblast produced by the method of producing osteoblasts according to any one of the above [36]-[45].

[47] A composition containing at least one inhibitor selected from a group consisting of an ALK5 inhibitor, a GSK3 inhibitor, an ALK2 inhibitor, and an ALK3 inhibitor, and a cAMP activator.

[48] The composition according to the above [47], containing at least the ALK2 inhibitor and the ALK3 inhibitor.
[49] The composition according to the above [47] or [48], further containing at least one inhibitor selected from a group consisting of an ALK6 inhibitor and an AMPK inhibitor.
[50] The composition according to the above [47] or [48], containing any of the following combinations:
(1) the ALK5 inhibitor, the GSK3 inhibitor, the ALK2 inhibitor, the ALK3 inhibitor, the ALK6 inhibitor, the AMPK inhibitor, and the cAMP activator;
(2) the ALK5 inhibitor, the GSK3 inhibitor, the ALK2 inhibitor, the ALK3 inhibitor, and the cAMP activator.
[51] The composition according to the above [48] or [50], wherein the ALK2 inhibitor and the ALK3 inhibitor are LDN193189 and/or dorsomorphin.
[52] The composition according to the above [49], wherein the at least one inhibitor selected from the group consisting of the ALK6 inhibitor and the AMPK inhibitor is dorsomorphin.
[53] The composition according to any one of the above [47]-[52], wherein the composition is for producing osteoblasts from a somatic cell.
[54] A method of producing chondrocytes, comprising a step d) of culturing a somatic cell in the presence of at least one inhibitor selected from a group consisting of a cAMP activator, an ALK5 inhibitor, an ALK2 inhibitor, an ALK3 inhibitor, and a GSK3 inhibitor, in the absence of an Erk inhibitor, and in the absence of at least one inhibitor selected from a group consisting of an ALK6 inhibitor and an AMPK inhibitor.
[55] The method of producing chondrocytes according to the above [54], wherein the step d) is a step of culturing the somatic cell in the presence of at least the ALK2 inhibitor and the ALK3 inhibitor.
[56] The method of producing chondrocytes according to the above [54] or [55], wherein the step d) is a step of culturing the somatic cell in the presence of the cAMP activator, the ALK5 inhibitor, the ALK2 inhibitor, the ALK3 inhibitor, and the GSK3 inhibitor, in the absence of the Erk inhibitor, and in the absence of the ALK6 inhibitor and the AMPK inhibitor.
[57] The method of producing chondrocytes according to the above [55] or [56], wherein the culturing the somatic cell in the presence of the ALK2 inhibitor and the ALK3 inhibitor comprises culturing the somatic cell in the presence of LDN193189.
[58] The method of producing chondrocytes according to any one of the above [54]-[57], wherein the step d) is a step of culturing the somatic cell in the absence of a p53 inhibitor.
[59] The method of producing chondrocytes according to any one of the above [54]-[58], wherein the step d) is a step of culturing the somatic cell in the absence of components acting on histone.
[60] The method of producing chondrocytes according to any one of the above [54]-[59], wherein the somatic cell is fibroblast.
[61] A chondrocyte produced by the method of producing chondrocytes according to any one of the above [54]-[60].
[62] A composition for producing chondrocytes from a somatic cell, containing at least one inhibitor selected from a group consisting of a cAMP activator, an ALK5 inhibitor, an ALK2 inhibitor, an ALK3 inhibitor, and a GSK3 inhibitor.
[63] The composition according to the above [62], containing at least the ALK2 inhibitor and the ALK3 inhibitor.
[64] A composition containing a cAMP activator, an ALK5 inhibitor, an ALK2 inhibitor, an ALK3 inhibitor, and a GSK3 inhibitor.
[65] The composition according to the above [63] or [64], wherein the ALK2 inhibitor and the ALK3 inhibitor are LDN193189.
[66] The composition according to the above [64] or [65], wherein the composition is for producing chondrocytes from the somatic cell.
[67] A method of producing neural cells, comprising a step e) of culturing a somatic cell in the presence of at least one inhibitor selected from a group consisting of an ALK6 inhibitor and an AMPK inhibitor.
[68] The method of producing neural cells according to the above [67], wherein the step e) is a step of culturing the somatic cell in the presence of the ALK6 inhibitor and the AMPK inhibitor.
[69] The method of producing neural cells according to the above [67] or [68], wherein the step e) is a step of culturing the somatic cell in the presence of at least one activator and/or inhibitor selected from a group consisting of a cAMP activator, an ALK2 inhibitor, an ALK3 inhibitor, an ALK5 inhibitor, a GSK3 inhibitor and an Erk inhibitor.
[70] The method of producing neural cells according to any one of the above [67]-[69], wherein the step e) is a step of culturing the somatic cell in the presence of any of the followings:
(1) the ALK6 inhibitor, the AMPK inhibitor, the cAMP activator, the ALK2 inhibitor, the ALK3 inhibitor, the ALK5 inhibitor, the GSK3 inhibitor, and the Erk inhibitor;
(2) the ALK6 inhibitor, the AMPK inhibitor, the ALK2 inhibitor, the ALK3 inhibitor, the ALK5 inhibitor, the GSK3 inhibitor, and the Erk inhibitor;
(3) the ALK6 inhibitor, the AMPK inhibitor, the cAMP activator, the ALK2 inhibitor, the ALK3 inhibitor, the ALK5 inhibitor, and the Erk inhibitor;
(4) the ALK6 inhibitor, the AMPK inhibitor, the cAMP activator, the ALK2 inhibitor, the ALK3 inhibitor, the ALK5 inhibitor, and the GSK3 inhibitor.
[71] The method of producing neural cells according to any one of the above [67]-[70], wherein culturing the somatic cell in the presence of the at least one inhibitor selected from the group consisting of the ALK6 inhibitor and the AMPK inhibitor comprises culturing the somatic cell in the presence of dorsomorphin.
[72] The method of producing neural cells according to the above [69], wherein culturing the somatic cell in the presence of the at least one inhibitor selected from the group consisting of the ALK2 inhibitor and the ALK3 inhibitor comprises culturing the somatic cell in the presence of LDN193189 and/or dorsomorphin.
[73] The method of producing neural cells according to any one of the above [67]-[72], wherein the step e) is a step of culturing the somatic cell in the absence of a p53 inhibitor.
[74] The method of producing neural cells according to any one of the above [67]-[73], wherein the step e) is a step of culturing the somatic cell in the absence of growth factors and/or cytokines.
[75] The method of producing neural cells according to any one of the above [67]-[74], wherein the step e) is a step of culturing the somatic cell in the absence of components acting on histone.
[76] The method of producing neural cells according to any one of the above [67]-[75], wherein the somatic cell is fibroblast.
[77] A neural cell produced by the method of producing neural cells according to any one of the above [67]-[76].

[78] A composition for producing neural cells from a somatic cell, containing at least one inhibitor selected from a group consisting of an ALK6 inhibitor and an AMPK inhibitor.

[79] A composition for producing neural cells from a somatic cell, containing an ALK6 inhibitor and an AMPK inhibitor.

[80] A composition for producing neural cells from a somatic cell, containing at least one inhibitor selected from a group consisting of an ALK6 inhibitor and an AMPK inhibitor, and at least one activator and/or inhibitor selected from a group consisting of a cAMP activator, an ALK2 inhibitor, an ALK3 inhibitor, an ALK5 inhibitor, a GSK3 inhibitor, and an Erk inhibitor.

[81] The composition according to the above [80], containing any of the following combinations:

(1) the ALK6 inhibitor, the AMPK inhibitor, the cAMP activator, the ALK2 inhibitor, the ALK3 inhibitor, the ALK5 inhibitor, the GSK3 inhibitor, and the Erk inhibitor;

(2) the ALK6 inhibitor, the AMPK inhibitor, the ALK2 inhibitor, the ALK3 inhibitor, the ALK5 inhibitor, the GSK3 inhibitor, and the Erk inhibitor;

(3) the ALK6 inhibitor, the AMPK inhibitor, the cAMP activator, the ALK2 inhibitor, the ALK3 inhibitor, the ALK5 inhibitor, and the Erk inhibitor;

(4) the ALK6 inhibitor, the AMPK inhibitor, the cAMP activator, the ALK2 inhibitor, the ALK3 inhibitor, the ALK5 inhibitor, and the GSK3 inhibitor.

[82] The composition according to the above [81], wherein the ALK6 inhibitor and the AMPK inhibitor are dorsomorphin.

[83] The composition according to the above [81], wherein the ALK2 inhibitor and the ALK3 inhibitor are LDN193189 and/or dorsomorphin.

[84] The composition according to any one of the above [80]-[83], wherein the composition is for producing the neural cells from the somatic cell.

[85] A method of producing cardiomyocytes, comprising a step f) of culturing a somatic cell in the presence of at least one inhibitor selected from a group consisting of an ALK6 inhibitor and an AMPK inhibitor, and in the presence of at least one inhibitor selected from a group consisting of a cAMP activator, an ALK5 inhibitor, and an Erk inhibitor.

[86] The method of producing cardiomyocytes according to the above [85], wherein the step f) is a step of culturing the somatic cell in the presence of the ALK6 inhibitor and the AMPK inhibitor, and in the presence of a cAMP activator, an ALK5 inhibitor, and an Erk inhibitor.

[87] The method of producing cardiomyocytes according to the above [85] or [86], wherein the step f) is a step of culturing the somatic cell in the presence of at least one inhibitor selected from a group consisting of an ALK2 inhibitor and an ALK3 inhibitor.

[88] The method of producing cardiomyocytes according to any one of the above [85]-[87], wherein the step f) is a step of culturing the somatic cell in the presence of a GSK3 inhibitor.

[89] The method of producing cardiomyocytes according to any one of the above [85]-[88], wherein the step f) is a step of culturing the somatic cell in the presence of any of the followings:

(1) the ALK6 inhibitor, the AMPK inhibitor, the cAMP activator, the ALK2 inhibitor, the ALK3 inhibitor, the ALK5 inhibitor, the GSK3 inhibitor, and the Erk inhibitor;

(2) the ALK6 inhibitor, the AMPK inhibitor, the cAMP activator, the ALK2 inhibitor, the ALK3 inhibitor, the ALK5 inhibitor, and the Erk inhibitor.

[90] The method of producing cardiomyocytes according to any one of the above [85]-[89], wherein the culturing the somatic cell in the presence of the at least one inhibitor selected from the group consisting of the ALK6 inhibitor and the AMPK inhibitor comprises culturing the somatic cell in the presence of dorsomorphin.

[91] The method of producing cardiomyocytes according to any one of the above [85]-[90], wherein the step f) is a step of culturing the somatic cell in the absence of an ALK4 inhibitor.

[92] The method of producing cardiomyocytes according to any one of the above [85]-[91], wherein the step f) is a step of culturing the somatic cell in the absence of a p53 inhibitor.

[93] The method of producing cardiomyocytes according to any one of the above [85]-[92], wherein the step f) is a step of culturing the somatic cell in the absence of components acting on histone.

[94] The method of producing cardiomyocytes according to any one of the above [85]-[93], wherein the somatic cell is fibroblast.

[95] A cardiomyocyte produced by the method of producing cardiomyocytes according to any one of the above [85]-[94]

[96] A composition containing at least one inhibitor selected from a group consisting of an ALK6 inhibitor and an AMPK inhibitor, as well as a cAMP activator, an ALK5 inhibitor, and an Erk inhibitor.

[97] The composition according to the above [96], containing the ALK6 inhibitor, the AMPK inhibitor, the cAMP activator, the ALK5 inhibitor, and the Erk inhibitor.

[98] The composition according to the above [96] or [97], further containing at least one inhibitor selected from a group consisting of an ALK2 inhibitor and an ALK3 inhibitor.

[99] The composition according to any one of the above [96]-[98], further containing a GSK3 inhibitor.

The composition according to any one of the above [96]-[98], containing any of the following combinations:

(1) the ALK6 inhibitor, the AMPK inhibitor, the cAMP activator, the ALK2 inhibitor, the ALK3 inhibitor, the ALK5 inhibitor, the GSK3 inhibitor, and the Erk inhibitor;

(2) the ALK6 inhibitor, the AMPK inhibitor, the cAMP activator, the ALK2 inhibitor, the ALK3 inhibitor, the ALK5 inhibitor, and the Erk inhibitor.

[101] The composition according to any one of the above [97]-[100], wherein the ALK6 inhibitor and the AMPK inhibitor are dorsomorphin.

[102] The composition according to any one of the above [96]-[101], wherein the composition is for producing the cardiomyocytes from the somatic cell.

Effects of the Invention

The production method or the composition according to the present invention makes it possible to produce brown adipocytes, osteoblasts, chondrocytes, neural cells or cardiomyocytes from somatic cells without gene transfer. The brown adipocytes, the osteoblasts, the chondrocytes, the neural cells, or the cardiomyocytes obtained according to the present invention are useful in regenerative medicine and the like.

BRIEF DESCRIPTION OF DRAWINGS

FIG. 1 shows results of immunostaining cells 21 days after onset of culturing and then immunostaining the cells.

FIG. 2 shows states of cells after 3-week treatment with each combination of compounds.

FIG. 3 shows results of quantifying Fabp 4 (adipocyte-specific gene) treated with each combination of compounds.

FIG. 4 shows results of immunostaining UCP1 proteins (green) and nucleus (blue) in a fibroblast of a 38-year-old subject. Since the photograph images in FIG. 4 are monochrome, green and blue are not displayed, but in the original photograph images of FIG. 4, green and blue are displayed.

FIG. 5 shows results of immunostaining UCP1 proteins (green) and nucleus (blue) in a fibroblast of a 38-year-old subject. Since the photograph images in FIG. 5 are monochrome, green and blue are not displayed, but in the original photograph images of FIG. 5, green and blue are displayed.

FIG. 6 shows results of immunostaining UCP1 proteins (green) and nucleus (blue) in a fibroblast of a 38-year-old subject. Since the photograph images in FIG. 6 are monochrome, green and blue are not displayed, but in the original photograph images of FIG. 6, green and blue are displayed.

FIG. 7 shows results of immunostaining UCP1 proteins (green) and nucleus (blue) in a fibroblast of a 38-year-old subject. Since the photograph images in FIG. 7 are monochrome, green and blue are not displayed, but in the original photograph images of FIG. 7, green and blue are displayed.

FIG. 8 shows results of immunostaining UCP1 proteins (green) and nucleus (blue) in a fibroblast of a 38-year-old subject. Since the photograph images in FIG. 8 are monochrome, green and blue are not displayed, but in the original photograph images of FIG. 8, green and blue are displayed.

FIG. 9 shows results of immunostaining UCP1 proteins (green) and mitochondria (red) in fibroblasts derived from 3 subjects aged 38—(A), 49 (B), and 0 (C). Since the photograph images in FIG. 9 are monochrome, green and red are not displayed, but in the original photograph images of FIG. 9, green and red are displayed.

FIG. 10 shows cells produced by culturing fibroblasts derived from 3 subjects aged 38—(A), 49 (B), and 0 (C) in a compound cocktail (5CORo-GM) for 3 weeks and then in only Ro for a week to allow them to mature.

FIG. 11 shows results quantifying expressions of Ucp1 gene, Ckmt1 gene, Cited1 gene, Colla2 gene, Fabp4 gene, AdipoQ gene and Pparγ gene in a control cell (untreated with a compound) and brown adipocytes derived from fibroblasts of subjects aged 0, 38, and 49. The data are indicated in mean±SD (n=3). Student t test: * $p<0.05$,  $p<0.01$, * $p<0.001$ FIG. 12 shows results of quantifying mRNAs of Ucp1, Ckmt1 and Cited1 in the brown adipocytes after treatment with isoproterenol (0.1 μM, 1 μM or 10 μM) or forskolin (0.1 μM, 1 μM or 10 μM). The first lane indicates an expression level of the control cell (with no compound), for which an expression level of the untreated brown adipocyte is standardized as 1. The data are indicated in mean±SD (n=3). Student t test: * $p<0.05$,  $p<0.01$, * $p<0.001$ FIG. 13 shows results of measuring oxygen consumption rates in the brown adipocytes (n=3 for each cell) derived from the control cell (with no compound) and fibroblasts (A: 38 years old, B: 49 years old, and C: 0 year old) using a Flux analyzer. At the times illustrated in the graph, Oligomycin (O), FCCP (F) and antimycin A/rotenone (A/R) were added. The data are indicated in mean±SD (n=3 to 5).

FIG. 14 shows results of staining cells 21 days after onset of culturing.

FIG. 15 shows results of staining cells 21 days after onset of culturing.

FIG. 16 shows results of immobilizing cells 14 days after onset of culturing and then immunostaining the cells.

FIG. 17 shows results of immobilizing cells 14 days after onset of culturing and then immunostaining the cells.

DESCRIPTION OF EMBODIMENTS

Hereinafter, embodiments of the present invention will be explained in detail.

1. Somatic Cell

Biological cells can be classified into somatic cells and reproductive cells. For the method according to the present invention, any somatic cell can be used as a starting material. The somatic cells are not particularly limited, and may be any of primary cultured cells collected from a living body or established cells. In the present invention, somatic cells at any of various differentiation stages, e.g. somatic cells at a terminal differentiation stage, somatic cells on the way to the terminal differentiation, or somatic cells that have been initialized to acquire pluripotency can be used. The somatic cells usable in the present invention are not particularly limited, and examples thereof include any somatic cell e.g. hematopoietic cells (various lymphocytes, macrophages, dendritic cells, bone marrow cells, etc.), organ-derived cells (hepatocytes, splenocytes, pancreatic cells, nephrocytes, pneumocytes, etc.), muscle cells (skeletal myocytes, smooth muscle cells, myoblasts, cardiomyocytes, etc.), fibroblasts, neural cells, osteoblasts, chondrocytes, endothelial cells, stromal cells, adipocytes (white adipocytes etc.), embryonic stem cells (ES cells), and the like. The method according to the present invention can also be applied to precursor cells and cancer cells of the aforementioned cells. Preferably, fibroblasts can be used as the somatic cells.

Examples of sources for the somatic cells include, but are not limited to, humans, nonhuman mammals, and nonmammal animals (birds, reptiles, amphibians, fishes, etc.). As the sources of the somatic cells, humans, and nonhuman mammals are preferable, and humans are particularly preferable. When brown adipocytes, osteoblasts, chondrocytes, neural cells, or cardiomyocytes are produced by the method according to the present invention for the purpose of administering the cells to humans, somatic cells collected from a donor having a histocompatibility antigen type identical to or similar to that of a recipient can be preferably used. Somatic cells collected from the recipient himself/herself may be used for producing brown adipocytes, osteoblasts, chondrocytes, neural cells or cardiomyocytes.

2. ALK5 Inhibitor

ALK5 is a TGFβ receptor subfamily member also referred to as TGFβR1 (transforming growth factor β receptor 1). The ALK5 is a serine/threonine kinase that forms a heterodimeric complex with a type II TGFβ receptor in response to binding with TGFβ, and transmits TGFβ signals from a cell surface to a cytoplasm.

The phrase "in the presence of the ALK5 inhibitor" refers to an aspect under a culture condition capable of inhibiting the ALK5. The means for inhibiting the ALK5 is not particularly limited, and any means capable of inhibiting the ALK5 can be used. In the present invention, a substance directly acting on the ALK5 and inhibit the function of the ALK5 (e.g. an anti-ALK5 antibody, and other drugs), an agent suppressing production of the ALK5 itself, and the like can be used. In addition, the ALK5 can also be inhibited by inhibiting the signaling involved with the ALK5 at an upstream of the signaling.

Although the ALK5 inhibitor is not particularly limited in the present invention, the following compounds can be used as the ALK5 inhibitor. Preferably, SB431542 can be used.

CultureSure® A83-01 (Wako Pure Chemical Industries, Ltd.) (CAS No.: 909910-43-6)

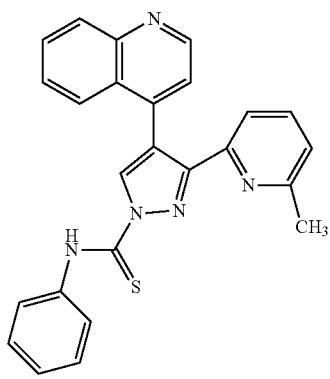

ALK5 Inhibitor (Wako Pure Chemical Industries, Ltd.) or Repsox (Abcam PLC) (CAS No.: 446859-33-2)

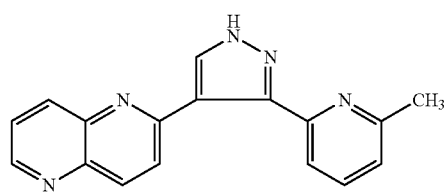

D4476 (Wako Pure Chemical Industries. Ltd.) (CAS No.: 301836-43-1)

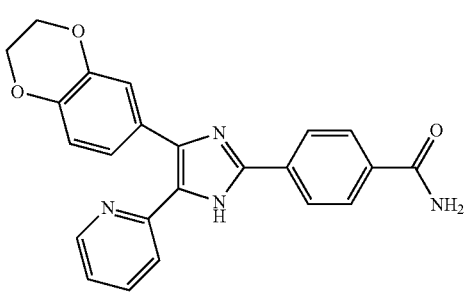

LY364947 (Wako Pure Chemical Industries, Ltd.) (CAS No.: 396129-53-6)

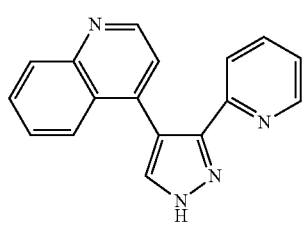

SB431542 (Wako Pure Chemical Industries, Ltd.) (CAS No.: 301836-41-9)

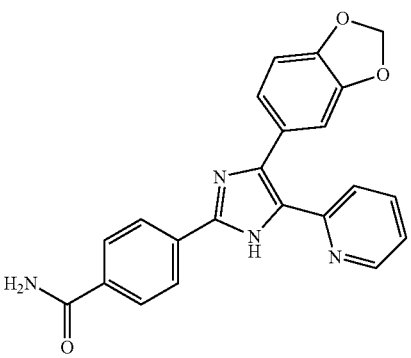

SB525334 (Wako Pure Chemical Industries, Ltd.) (CAS No.: 356559-20-1)

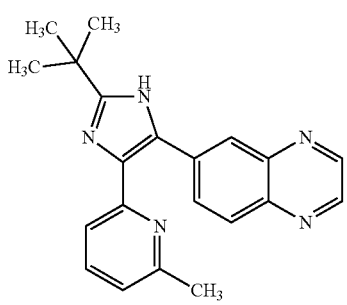

SD208 (Wako Pure Chemical Industries, Ltd.) (CAS No.: 627536-09-8)

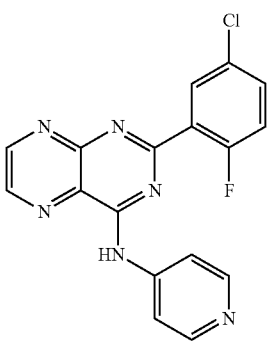

A concentration of the ALK5 inhibitor may be appropriately determined and is not particularly limited, but the ALK5 inhibitor can be used e.g. in a range of 0.2 µmol/L to 20 µmol/L, preferably 0.5 µmol/L to 10 µmol/L.

3. ALK6 Inhibitor

ALK6 is known also as BMPR1B, and is a transmembrane serine/threonine kinase member in the bone morphogenetic protein (BMP) receptor members. The ALK6 is considerably similar to activin receptors ACVR1 and ACVR2, and involved mainly in osteogenesis and embryogenesis in a cartilage.

The phrase "in the presence of the ALK6 inhibitor" refers to an aspect under a culture condition capable of inhibiting the ALK6. The means for inhibiting the ALK6 is not particularly limited, and any means capable of inhibiting the ALK6 can be used. In the present invention, a substance directly acting on the ALK6 and inhibit the function of the ALK6 (e.g. an anti-ALK6 antibody, and other drugs), an agent suppressing production of the ALK6 itself, and the like can be used. In addition, the ALK6 can also be inhibited by inhibiting the signaling involved with the ALK6 at an upstream of the signaling.

Although the ALK6 inhibitor is not particularly limited in the present invention, the following compounds can be used as the ALK6 inhibitor. Preferably, dorsomorphin can be used.

Dorsomorphin (Dorsomorphin: Wako Pure Chemical Industries, Ltd.) (CAS No.: 866405-64-3)

[Chem. 8]

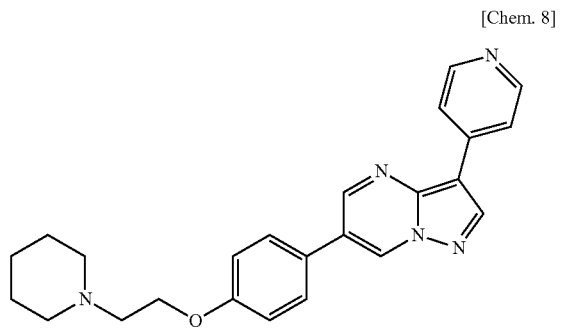 [SMILES: c1cc(-c2cnn3cc(-c4ccc(OCCN5CCCCC5)cc4)cnc23)ccn1]

K02288 (CAS No.: 1431985-92-0)

[Chem. 9]

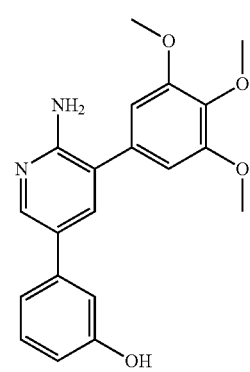

A concentration of the ALK6 inhibitor may be appropriately determined and is not particularly limited, but the ALK6 inhibitor can be used e.g. in a range of 0.1 μmol/L to 10 μmol/L, preferably 0.2 μmol/L to 5 μmol/L.

4. AMPK Inhibitor

AMPK (AMP-activated protein kinase) is a kind of serine/threonine kinases, and plays a role of a sensor for intracellular energy. Energy is generated in a process whereby s ATP is decomposed into AMP and phosphoric acid, and a protein kinase activated by the AMP at this time is the AMPK. Also, it is known that the AMPK affects the activity of several proteins related to control of cell proliferation.

The phrase "in the presence of the AMPK inhibitor" refers to an aspect under a culture condition capable of inhibiting the AMPK. The means for inhibiting the AMPK is not particularly limited, and any means capable of inhibiting the AMPK can be used. In the present invention, a substance directly acting on the AMPK and inhibit the function of the AMPK (e.g. an anti-AMPK antibody, and other drugs), an agent suppressing production of the AMPK itself, and the like can be used. In addition, the AMPK can also be inhibited by inhibiting the signaling involved with the AMPK at an upstream of the signaling.

Although the AMPK inhibitor is not particularly limited in the present invention, the following compounds can be used as the AMPK inhibitor. Preferably, dorsomorphin can be used.

Dorsomorphin (Dorsomorphin: Wako Pure Chemical Industries, Ltd.) (AMPK Inhibitor, also referred to as Compound C) (CAS No.: 866405-64-3)

Indirubin-3'-oxime (Wako Pure Chemical Industries, Ltd.) (CAS No.: 160807-49-8)

[Chem. 10]

Dorsomorphin dihydrochloride (CAS No.: 1219168-18-9)

Doxorubicin hydrochloride (CAS No.: 25316-40-9)

STO-609 (CAS No.: 52029-86-4)

A concentration of the AMPK inhibitor may be appropriately determined and is not particularly limited, but the AMPK inhibitor can be used e.g. in a range of 0.1 μmol/L to 10 μmol/L, preferably 0.2 μmol/L to 5 μmol/L.

5. cAMP Activator

As a second messenger, cAMP (cyclic adenosine monophosphate) is a substance involved in various intracellular signaling. In cells, the cAMP is produced by adenosine triphosphate (ATP) being cyclized by an adenylate cyclase.

The phrase "in the presence of the cAMP activator" refers to an aspect under a culture condition capable of activating the cAMP. The means for activating the cAMP is not particularly limited, and any means capable of increasing an intracellular cAMP level can be used. As a means for increasing the intracellular cAMP level, a substance capable of directly acting on an adenylate cyclase as an enzyme involved in production of the cAMP to activate the adenylate cyclase, a substance capable of enhancing expression of the adenylate cyclase, and furthermore a substance inhibiting a phosphodiesterase as a cAMP-decomposing enzyme, and the like can be used, for example. A dibutyryl cAMP which is a structural analog of the cAMP and has the same action as of the cAMP in cells can also be used.

Examples of the cAMP activator (adenylate cyclase activator) usable in the present invention include a forskolin (CAS No.: 66575-29-9) and a forskolin derivative (e.g. Japanese Patent Application Laid-Open No. 2002-348243) and the like. It is preferable that the forskolin can be used.

Forskolin (CAS No.: 66428-89-5)

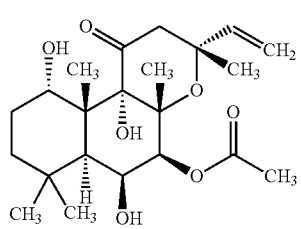

Isoproterenol (CAS No.: 7683-59-2)

NKH477 (CAS No.: 138605-00-2)

PACAP1-27 (CAS No.: 127317-03-7)

PACAP1-38 (CAS No.: 137061-48-4)

A concentration of the cAMP activator may be appropriately determined and is not particularly limited, but the cAMP activator can be used e.g. in a range of 0.5 µmol/L to 50 µmol/L, preferably 1 µmol/L to 30 µmol/L.

6. ALK2 Inhibitor and ALK3 Inhibitor

ALK2 is a receptor serine/threonine kinase which is an ALK family member, and locates upstream of a signaling pathway involving SMAD proteins, particularly SMAD 1/5/8. Motility of prostate cancer cells is decreased by endoglin through activation of an ALK2-Smad1 pathway. The ALK2 gene is a major gene involved in fibrodysplasia ossificans progressiva (FOP) which is a rare autosomal dominant congenital disease characterized by progressive heterotopia osteogenesis in muscle tissues.

ALK3 is a transmembrane serine/threonine kinase family member. The ALK3 gene acts as a minor susceptibility gene in PTEN (phosphatase and tensin homologue deleted on chromosome 10) mutation-negative Cowden's disease. ALK3 transportation plays an important role in FOP pathogenesis, and is also involved in human T cell differentiation.

The phrase "in the presence of the ALK2 inhibitor and the ALK3 inhibitor" refers to an aspect under a culture condition capable of inhibiting the ALK2 and the ALK3. The means for inhibiting the ALK2 and the ALK3 is not particularly limited, and any means capable of inhibiting the ALK2 and the ALK3 can be used. In the present invention, a substance directly acting on the ALK2 and the ALK3 and inhibit the function of the ALK2 and the ALK3 (e.g. an anti-ALK2 antibody, an anti-ALK3 antibody, and other drugs), an agent suppressing production of the ALK2 itself or the ALK3 itself, and the like can be used. In addition, the ALK2 and the ALK3 can also be inhibited by inhibiting the signaling involved with the ALK2 and the ALK3 at an upstream of the signaling.

Although the ALK2 inhibitor and the ALK3 inhibitor are not particularly limited in the present invention, the following compounds can be used as the ALK2 inhibitor and the ALK3 inhibitor. Preferably, LDN193189, which inhibits both the ALK2 and the ALK3, can be used.

DMH1 (ALK2 inhibitor) (CAS No.: 1206711-16-1)

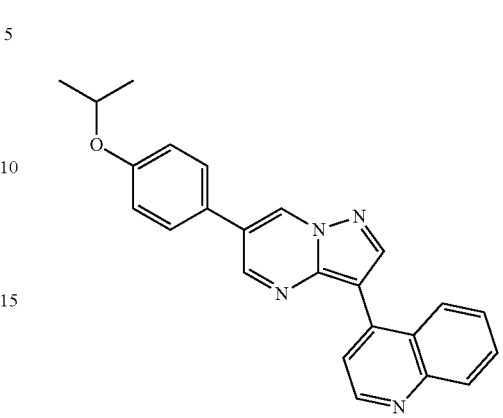

K02288 (ALK2 inhibitor and ALK3 inhibitor) (CAS No.: 1431985-92-0)

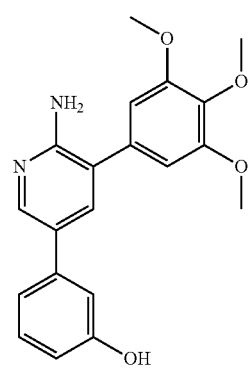

LDN212854 (ALK2 inhibitor and ALK3 inhibitor) (CAS No.: 1432597-26-6)

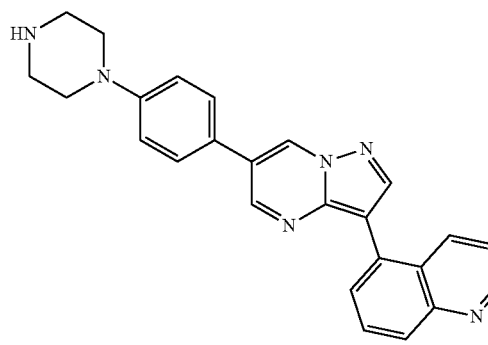

LDN193189 (ALK2 inhibitor and ALK3 inhibitor) (CAS No.: 1062368-24-4)

[Chem. 15]

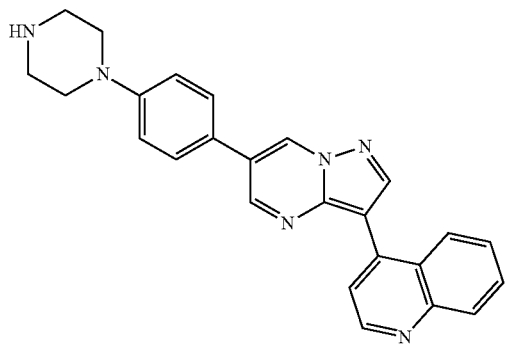

LDN193189 HC (ALK2 inhibitor and ALK3 inhibitor) (CAS No.: 1062368-62-0)

[Chem. 16]

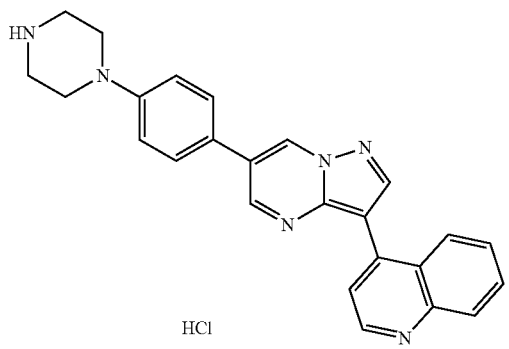

ML347 (ALK2 inhibitor and ALK3 inhibitor) (CAS No.: 1062368-49-3)

[Chem. 17]

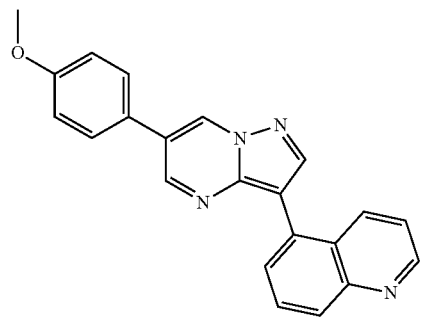

LDN214117 (CAS No.: 1627503-67-6)

Concentrations of the ALK2 inhibitor and the ALK3 inhibitor may be appropriately determined and is not particularly limited, but the ALK2 inhibitor and the ALK3 inhibitor can be used e.g. in a range of 0.1 µmol/L to 10 µmol/L, preferably 0.2 µmol/L to 5 µmol/L.

7. GSK3 Inhibitor

Glycogen synthase kinase (GSK) 3 was found as a protein kinase which phosphorylates and inactivates glycogen synthases. In mammals, the GSK3 is classified into 2 isoforms of 51 kDa of α (GSK3α) and 47 kDa of β (GSK3β). The GSK3 has an activity of phosphorylating various proteins and is involved in not only glycogen metabolism but also physiological phenomena such as cell division and cell proliferation.

The phrase "in the presence of the GSK3 inhibitor" refers to an aspect under a culture condition capable of inhibiting the GSK3. The means for inhibiting the GSK3 is not particularly limited, and any GSK3 activity-inhibiting substance, e.g. a GSK3 signal-inhibiting means such as an anti-GSK3 antibody and a GSK inhibitor can be used. In addition, since the GSK3 is inactivated when a specific site of its own is phosphorylated, a means for promoting the phosphorylation can also be used for inhibiting the GSK3 signals.

The following compounds can be used as the GSK3 inhibitor which can be used for the present invention. Preferably, CHIR99021 can be used.

CHIR99021 (CAS No.: 252917-06-9)

[Chem. 18]

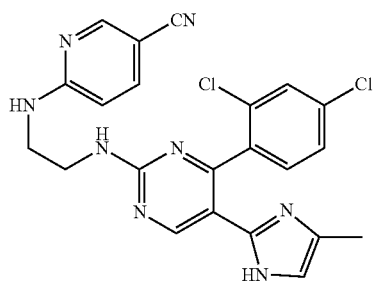

BIO((2'Z,3'E)-6-Bromoindinbin-3'-oxime) (CAS No.: 667463-62-9)

[Chem. 19]

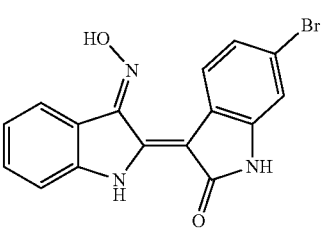

Kenpaullone (CAS No.: 142273-20-9)

[Chem. 20]

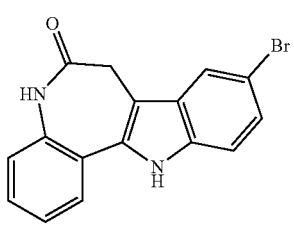

A1070722 (CAS No.: 1384424-80-9)

Olornoucine (CAS No.: 101622-51-9)

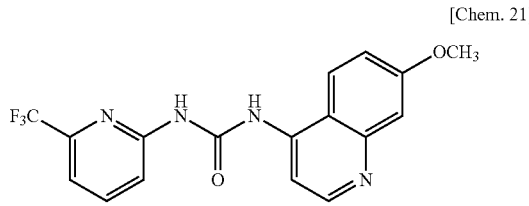

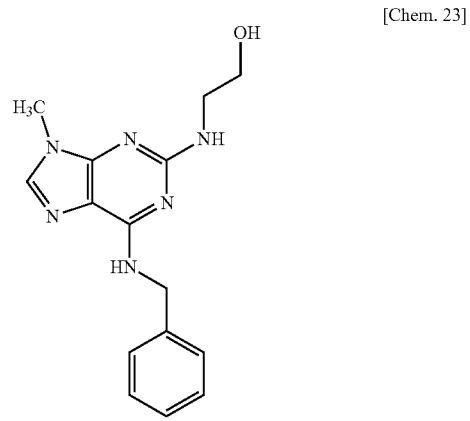 [SMILES: Cn1cnc2c(NCc3ccccc3)nc(NCCO)nc21]

SB216763 (CAS No.: 280744-09-4)
CHIR98014 (CAS No.: 556813-39-9)
TWS119 (CAS No.: 601514-19-6)
Tideglusib (CAS No.: 865854-05-3)
SB415286 (CAS No.: 264218-23-7)
Bikinin (CAS No.: 188011-69-0)
IM-12 (CAS No.: 1129669-05-1)
1-Azakenpaullone (CAS No.: 676596-65-9)
LY2090314 (CAS No.: 603288-22-8)
AZD1080 (CAS No.: 612487-72-6)
AZD2858 (CAS No.: 486424-20-8)
AR-A014418 (CAS No.: 487021-52-3)
TDZD-8 (CAS No.: 327036-89-5)
Indirubin (CAS No.: 479-41-4)

A concentration of the GSK3 inhibitor may be appropriately determined and is not particularly limited, but the GSK3 inhibitor can be used e.g. in a range of 0.1 μmol/L to 10 μmol/L, preferably 0.2 μmol/L to 5 μmol/L.

8. Erk Inhibitor

Erk is a MAPK subfamily which is activated by EGF (epidermal growth factor), serum stimulation or oxidative stress, or the like, and can be classified into ERK1/2, ERK5, ERK7, ERK8 depending on difference in the relevant signaling pathways. A ligand binds to a tyrosine kinase receptor such as an epidermal growth factor receptor (EGFR), thereby signaling occurs, and as a result, a TEY motif present in an activation loop of the Erk is phosphorylated and activated.

The phrase "in the presence of the Erk inhibitor" refers to an aspect under a culture condition capable of inhibiting the Erk. The means for inhibiting the Erk is not particularly limited, and a substance inhibiting the Erk activity, e.g., an Erk signal-inhibiting means such as an anti-Erk antibody and an Erk inhibitor can be used. Also, an enzyme involved in Erk activation, e.g., an Erk kinase, an Erk kinase kinase, or the like can be used for inhibiting the Erk.

Although the Erk inhibitor is not particularly limited in the present invention, the following compounds can be used as the Erk inhibitor. Preferably, PD0325901 can be used.

PD0325901 (CAS No.: 391210-10-9)

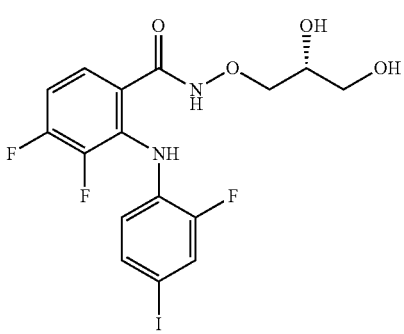

Amninopurvalanol A (CAS No.: 220792-57-4)

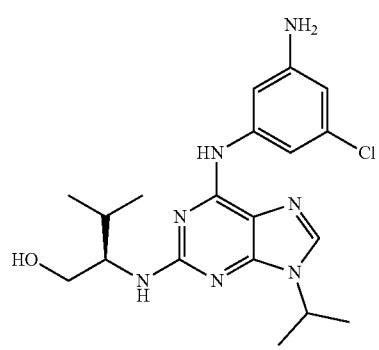

AS703026 (CAS No.: 1236699-92-5)
AZD8330 (CAS No.: 869357-68-6)
BIX02188 (CAS No.: 334949-59-6)
BIXO2189 (CAS No.: 1265916-41-3)
CI-1040 (CAS No.: 212631-79-3)
Cobimetirlib (CAS No.: 934660-93-2)
GDC-0623 (CAS No.: 1168091-68-6)
MEk162 (CAS No.: 606143-89-9)
PD318088 (CAS No.: 391210-00-7)
PD98059 (CAS No.: 167869-21-8)
Refametinib (CAS No.: 923032-37-5)
R04987655 (CAS No.: 874101-00-5)
SCH772984 (CAS No.: 942183-80-4)
Selumetinib (CAS No.: 606143-52-6)
SL327 (CAS No.: 305350-87-2)
Trametinib (CAS No.: 871700-17-3)
ARRY-142886 (CAS No.: 606143-52-6)
XL518 (CAS No.: 934660-93-2)
RDEA119 (CAS No.: 923032-38-6)

A concentration of the Erk inhibitor may be appropriately determined and is not particularly limited, but the Erk inhibitor can be used e.g. in a range of 0.1 μmol/L to 10 μmol/L, preferably 0.2 μmol/L to 5 μmol/L.

9. Preferable Culture Condition

Although the culture condition is not particularly limited in the present invention, it is preferable to culture somatic cells in the absence of the p53 inhibitor in steps a) to f). The phrase "in the absence of the p53 inhibitor" refers to an aspect that there is there is substantially no p53 inhibitor, and includes not only a case that there is no p53 inhibitor but also a case that there is a trace amount of the p53 inhibitor. The p53 protein is a product of the p53 gene known as a tumor suppressor gene, and is involved in cell cycle regulation and apoptosis regulation. The function of the p53 is exerted through specific binding with DNA and gene expression control. Examples of the p53 inhibitor include pifithrin-α (CAS No.: 63208-82-2), pifithrin-β (CAS No.: 511296-88-1), pifithrin-μ(CAS No.: 64984-31-2), NSC66811 (CAS No.: 6964-62-1), Nultin-3 (CAS No.: 548472-68-0), and the like. However, in the present invention, the somatic cells can be cultured in the absence of the aforementioned p53 inhibitors.

Preferably, the somatic cells are cultured in the absence of components acting on histone in steps a) to f), but this is not particularly limited in the present invention. The phrase "in the absence of the components acting on histone" refers to an aspect that there is there is substantially no component acting on histone, and includes not only a case that there is no component acting on histone, but also a case that there is a trace amount of the component acting on histone. Examples of the component acting on histone include a histone deacetylase inhibitor, and the like. If the histone deacetylase inhibitor which is said to promote reprogramming by a nuclear reprogramming factor is not used, a risk of induction of pluripotent cells which may cause unintended differentiation is lowered.

10. Culture of Somatic Cell

In the preset invention, the somatic cells should be cultured in the presence of the aforementioned various inhibitors (and optionally, activators) by selecting a medium, a temperature and other conditions according to the somatic cell type to be used. The medium can be selected from known media or commercially available media. For example, a medium prepared by adding appropriate components (serum, protein, amino acid, saccharide, vitamin, fatty acid, antibiotic, etc.) to a general medium MEM (Minimum Essential Medium), DMEM (Dulbecco's Modified Eagle Medium), DMEM/F12, or a modified medium of these media can be used.

As the culture condition, it is only necessary to select a general cell culture condition. The condition is exemplified by a condition at 37° C., 5% $CO_2$, and the like. During culture, it is preferable to change the medium at an appropriate interval (preferably once every 1 to 7 days, more preferably once every 3 to 4 days). When the method according to the present invention is carried out using fibroblasts as materials, brown adipocytes, osteoblasts, chondrocytes, neural cells, or cardiomyocytes appear under a condition at 37° C. and 5% $CO_2$, in 5-8 days to 3 weeks. As the somatic cells for use, somatic cells easy to culture are selected, so that somatic cells of which the number has been previously increased can be transformed into brown adipocytes, osteoblasts, chondrocytes, neural cells, or cardiomyocytes. Thus, upscaled brown adipocytes, osteoblasts, chondrocytes, neural cells or cardiomyocytes can also be easily produced.

For culturing somatic cells, a cell culture vessel such as a plate, a dish, a cell culture flask and a cell culture bag can be used. Note that, as the cell culture bag, a gas-permeable bag is preferable. If a large amount of cells are required, a large culture tank may be used. The culture can be carried out both in an open system or a closed system. However, when the obtained brown adipocytes, osteoblasts, chondrocytes, neural cells, or cardiomyocytes are intended for administration or the like to humans, culture in the closed system is preferable.

In the method according to the present invention, the somatic cells are cultured in the medium containing the aforementioned various inhibitors, so that brown adipocytes, osteoblasts, chondrocytes, neural cells, or cardiomyocytes can be produced from the somatic cells in one-step culture.

A. Invention Related to Brown Adipocyte

[1] A Method of Producing Brown Adipocyte

The present invention relates to a method of producing brown adipocytes, comprising a step a) of culturing a somatic cell in the presence of an ALK5 inhibitor and in the presence of at least one inhibitor selected from a group consisting of an ALK6 inhibitor and an AMPK inhibitor.

Preferably, the step a) is a step of culturing the somatic cell in the presence of the ALK6 inhibitor and the AMPK inhibitor.

Preferably, the step a) is a step of culturing the somatic cell in the presence of at least one activator and/or inhibitor selected from a group consisting of a cAMP activator, an ALK2 inhibitor, an ALK3 inhibitor, a GSK3 inhibitor, and an Erk inhibitor.

Particularly preferably, the step a) is a step of culturing the somatic cell in the presence of any of the followings:

(1) the ALK5 inhibitor, the ALK6 inhibitor, the AMPK inhibitor, the cAMP activator, the ALK2 inhibitor, the ALK3 inhibitor, the GSK3 inhibitor, and the Erk inhibitor;

(2) the ALK5 inhibitor, the ALK6 inhibitor, the AMPK inhibitor, the cAMP activator, the ALK2 inhibitor, and the ALK3 inhibitor;

(3) the ALK5 inhibitor, the ALK6 inhibitor, the AMPK inhibitor, the ALK2 inhibitor, the ALK3 inhibitor, the GSK3 inhibitor, and the Erk inhibitor;

(4) the ALK5 inhibitor, the ALK6 inhibitor, the AMPK inhibitor, the cAMP activator, the ALK2 inhibitor, the ALK3 inhibitor, and the Erk inhibitor;

(5) the ALK5 inhibitor, the ALK6 inhibitor, the AMPK inhibitor, the cAMP activator, the ALK2 inhibitor, the ALK3 inhibitor, and the GSK3 inhibitor;

(6) the ALK5 inhibitor, the ALK6 inhibitor, the AMPK inhibitor, the ALK2 inhibitor, and the ALK3 inhibitor.

The present invention further relates to a method of producing brown adipocytes, comprising a step b) of culturing a somatic cell in the presence of at least one group selected from five groups consisting of: (1) an Erk inhibitor; (2) an ALK2 inhibitor and an ALK3 inhibitor; (3) an ALK5 inhibitor; (4) an ALK6 inhibitor, an AMPK inhibitor, the ALK2 inhibitor, and the ALK3 inhibitor; and (5) a cAMP activator.

Preferably, the step b) is a step of culturing the somatic cell in the presence of at least two groups selected from five groups consisting of: (1) the Erk inhibitor; (2) the ALK2 inhibitor and the ALK3 inhibitor; (3) the ALK5 inhibitor; (4) the ALK6 inhibitor, the AMPK inhibitor, the ALK2 inhibitor and the ALK3 inhibitor; and (5) the cAMP activator.

Preferably, the step b) is a step of culturing the somatic cell in the presence of any of the followings:

(i) the ALK6 inhibitor, the AMPK inhibitor, the ALK2 inhibitor, and the ALK3 inhibitor, as well as the cAMP activator;

(ii) the ALK6 inhibitor, the AMPK inhibitor, the ALK2 inhibitor, and the ALK3 inhibitor, as well as the Erk inhibitor;

(iii) the ALK6 inhibitor, the AMPK inhibitor, the ALK2 inhibitor, and the ALK3 inhibitor, as well as the ALK5 inhibitor;

(iv) the cAMP activator, as well as the ALK2 inhibitor and the ALK3 inhibitor;

(v) the cAMP activator, as well as the Erk inhibitor (vi) the cAMP activator, as well as the ALK5 inhibitor;
(vii) the ALK2 inhibitor, and the ALK3 inhibitor, as well as the ALK5 inhibitor; and
(viii) the Erk inhibitor, as well as the ALK5 inhibitor.

Preferably, the step b) is a step of culturing the somatic cell in the presence of at least three groups (more preferably, at least four groups) selected from five groups consisting of: (1) the Erk inhibitor; (2) the ALK2 inhibitor and the ALK3 inhibitor; (3) the ALK5 inhibitor; (4) the ALK6 inhibitor, the AMPK inhibitor, the ALK2 inhibitor, and the ALK3 inhibitor; and (5) the cAMP activator.

The present invention further relates to a method of producing brown adipocytes, comprising a step b) of culturing a somatic cell in the presence of at least five groups selected from six groups consisting of: (1) an Erk inhibitor; (2) an ALK2 inhibitor and an ALK3 inhibitor; (3) an ALK5 inhibitor; (4) an ALK6 inhibitor, an AMPK inhibitor, the ALK2 inhibitor, and the ALK3 inhibitor; (5) a cAMP activator; and (6) a GSK3 inhibitor.

<Inhibitor Having Two or More Inhibitory Actions>

As the aforementioned various inhibitors, an inhibitor having 2 or more inhibitory actions may be used.

For example, as the ALK2 inhibitor and the ALK3 inhibitor, LDN193189 inhibiting both ALK2 and ALK3 can be used, or dorsomorphin inhibiting ALK2, ALK3, ALK6 and AMPK can also be used. That is, culture of the somatic cells in the presence of at least one inhibitor selected from the ALK2 inhibitor and the ALK3 inhibitor may be achieved by culturing the somatic cells in the presence of the LDN193189 and/or the dorsomorphin.

In addition, as the ALK6 inhibitor and the AMPK inhibitor, the dorsomorphin inhibiting both ALK6 and the AMPK can be used. That is, culture of the somatic cells in the presence of at least one inhibitor selected from a group consisting of the ALK6 inhibitor and the AMPK inhibitor may be achieved by culturing the somatic cells in the presence of the dorsomorphin.

In addition, as the ALK6 inhibitor, the AMPK inhibitor, the ALK2 inhibitor and the ALK3 inhibitor, the dorsomorphin inhibiting the ALK6, AMPK, ALK2 and ALK3 can be used. That is, culture of the somatic cells in the presence of the ALK6 inhibitor, the AMPK inhibitor, the ALK2 inhibitor and the ALK3 inhibitor may be achieved by culturing the somatic cells in the presence of the dorsomorphin.

<Culture of Somatic Cell>

In the present invention, brown adipocytes are produced from somatic cells. As a substance effective for differentiation induction into adipocytes, dexamethasone, insulin, 3-isobutyl-1-methylxanthine, rosiglitazone, glucocorticoid, phosphodiesterase inhibitor, triiodothyronine (also referred to as T3) and the like are known. As a substance effective for differentiation induction into brown adipocytes, for example, a substance commercially available as a differentiation inducer can be used. In the present invention, it is preferable to culture the somatic cells in the presence of the aforementioned substance.

Preferably, 1 or more kinds, preferably 2 or more kinds, more preferably 3 or more kinds, even more preferably four kinds selected from dexamethasone, insulin, 3-isobutyl-1-methylxanthine and rosiglitazone can be used.

When using dexamethasone, the concentration of dexamethasone is not particularly limited, but is preferably within a range of 0.2 µmol/L to 20 µmol/L, preferably 0.5 µmol/L to 10 µmol/L.

When using insulin, the concentration of insulin is not particularly limited, but is preferably within a range of 1 µg/mL to 100 µg/mL, preferably 2 gµg/mL to 50 µg/mL.

When using 3-isobutyl-1-methylxanthine, the concentration of 3-isobutyl-1-methylxanthine is not particularly limited, but is preferably within a range of 0.05 µmol/L to 50 µmol/L, preferably 0.1 µmol/L to 10 µmol/L.

When using rosiglitazone, the concentration of rosiglitazone is not particularly limited, but is preferably within a range of 0.1 µmol/L to 10 µmol/L, preferably 0.2 µmol/L to 5 µmol/L.

<Brown Adipocyte>

A cell population containing the brown adipocytes can be obtained by the aforementioned method for producing the brown adipocytes according to the present invention. The brown adipocytes produced by the method for producing the brown adipocytes according to the present invention are also within the scope of the present invention. The brown adipocytes produced by the method according to the present invention may be terminally differentiated cells or precursor cells destined to differentiate into the brown adipocytes. In addition, the brown adipocytes produced by the method according to the present invention may also be beige cells or bright cells known as brown adipocyte-like cells.

The brown adipocytes produced by the method according to the present invention can be detected, confirmed and separated using e.g. the morphological change of the cells, the characteristic property of the brown adipocytes, and a specific marker.

In the adipocytes, fat accumulates. Thus, the adipocytes can be detected by intracellular fat staining using Oil Red O.

The specific marker of the brown adipocytes includes but not limited to: UCP1; EVOL3 (Elongation of very long chain fatty acid protein 3); PGC1A (PPAR gamma coactivator 1-alpha); PRDM 16 (PRD1-BF1-RIZ1 homologous domain containing 16); CIDEA (Cell Death-Inducing DFFA-Like Effector A); and the like. UCP1 is a kind of uncoupling proteins.

The specific marker can be detected by using a quarantine method (detection by antibodies), meanwhile the protein molecules may be detected by quantifying an amount of its mRNAs. An antibody capable of recognizing a specific marker of the brown adipocytes is also useful for isolating and purifying the brown adipocytes obtained by the method according to the present invention.

The brown adipocytes produced by the method according to the present invention can be used e.g. for the purpose of repairing tissues after surgical treatment. The brown adipocytes produced by the method according to the present invention can be used to produce a pharmaceutical composition for the tissue repair or the like. In addition, transplantation and administration of the brown adipocytes to living bodies are expected to have effects on metabolism improvement, obesity prevention and the like for the living bodies.

When the brown adipocyte is used as a pharmaceutical composition, the composition should be formulated into a pharmaceutical preparation in a form suitable for administration to an individual e.g. by mixing the brown adipocyte with a pharmaceutically acceptable carrier in accordance with a conventional method. The carrier can include distilled water for injection, which is made isotonic by adding physiological saline, glucose and other adjuvants (e.g. D-sorbitol, D-mannitol, sodium chloride, etc.). Furthermore, a buffer (e.g. phosphate buffer, a sodium acetate buffer), an analgesic (e.g. benzalkonium chloride, procaine hydrochloride, etc.), a stabilizer (e.g. human serum albumin, polyethylene glycol, etc.), a preservative, an antioxidant, and the like may be blended.

Furthermore, the brown adipocyte can be made into a composition combined with other cells and components effective for functionality exertion and bioadhesiveness improvement of the brown adipocyte.

Furthermore, the brown adipocytes produced by the method according to the present invention can also be used for screening a drug candidate compound capable of acting on the brown adipocyte and for evaluating safety of the drug candidate compound. Since the present invention can provide a large amount of brown adipocytes in one operation, a reproducible study result can be obtained with no influence from the difference in lot of the cells.

[2] Compositions

The present invention further relates to a composition containing an ALK5 inhibitor and at least one inhibitor selected from a group consisting of an ALK6 inhibitor and an AMPK inhibitor.

Preferably, the composition according to the present invention contains the ALK6 inhibitor and the AMPK inhibitor.

Preferably, the composition according to the present invention contains an AMP activator, an ALK2 inhibitor, an ALK3 inhibitor, a GSK3 inhibitor, and an Erk inhibitor.

Specific examples of the composition according to the present invention include compositions containing any of the followings:

(1) the ALK5 inhibitor, the ALK6 inhibitor, the AMPK inhibitor, the cAMP activator, the ALK2 inhibitor, the ALK3 inhibitor, the GSK3 inhibitor, and the Erk inhibitor;

(2) the ALK5 inhibitor, the ALK6 inhibitor, the AMPK inhibitor, the cAMP activator, the ALK2 inhibitor, and the ALK3 inhibitor;

(3) the ALK5 inhibitor, the ALK6 inhibitor, the AMPK inhibitor, the ALK2 inhibitor, the ALK3 inhibitor, the GSK3 inhibitor, and the Erk inhibitor;

(4) the ALK5 inhibitor, the ALK6 inhibitor, the AMPK inhibitor, the cAMP activator, the ALK2 inhibitor, the ALK3 inhibitor, and the Erk inhibitor;

(5) the ALK5 inhibitor, the ALK6 inhibitor, the AMPK inhibitor, the cAMP activator, the ALK2 inhibitor, the ALK3 inhibitor, and the GSK3 inhibitor;

(6) the ALK5 inhibitor, the ALK6 inhibitor, the AMPK inhibitor, the ALK2 inhibitor, and the ALK3 inhibitor.

Specific examples and preferable examples of the above-mentioned activators and inhibitors have been already described herein.

The present invention further relates to a composition for producing brown adipocytes from the somatic cell, containing at least one group (preferably at least two groups, at least three groups, or at least four groups) selected from five groups consisting of: (1) an Erk inhibitor; (2) an ALK2 inhibitor and an ALK3 inhibitor; (3) an ALK5 inhibitor; (4) an ALK6 inhibitor, an AMPK inhibitor, the ALK2 inhibitor, and the ALK3 inhibitor; and (5) a cAMP activator.

Specific examples of the composition according to the present invention include compositions containing any of the followings:

(i) the ALK6 inhibitor, the AMPK inhibitor, the ALK2 inhibitor, and the ALK3 inhibitor, as well as the cAMP activator;

(ii) the ALK6 inhibitor, the AMPK inhibitor, the ALK2 inhibitor, and the ALK3 inhibitor, as well as the Erk inhibitor;

(iii) the ALK6 inhibitor, the AMPK inhibitor, the ALK2 inhibitor, and the ALK3 inhibitor, as well as the ALK5 inhibitor;

(iv) the cAMP activator, as well as the ALK2 inhibitor and the ALK3 inhibitor;

(v) the cAMP activator, as well as the Erk inhibitor (vi) the cAMP activator, as well as the ALK5 inhibitor;

(vii) the ALK2 inhibitor, and the ALK3 inhibitor, as well as the ALK5 inhibitor; and (viii) the Erk inhibitor, as well as the ALK5 inhibitor.

The present invention further relates to a composition for producing brown adipocytes, containing at least five groups selected from groups consisting of: (1) an Erk inhibitor; (2) an ALK2 inhibitor and an ALK3 inhibitor; (3) an ALK5 inhibitor; (4) an ALK6 inhibitor, an AMPK inhibitor, the ALK2 inhibitor, and the ALK3 inhibitor; (5) a cAMP activator; and (6) a GSK3 inhibitor.

The composition according to the present invention can be used as a composition for producing the brown adipocytes from the somatic cells. The composition according to the present invention can also be used as a medium for producing the brown adipocytes from the somatic cells.

The medium used for producing the brown adipocytes from the somatic cells can be exemplified by a medium prepared by adding the ALK5 inhibitor and at least one inhibitor selected from a group consisting of the ALK6 inhibitor and the AMPK inhibitor as active ingredients to a basal medium prepared by mixing components necessary for cell culture. It is only necessary for the aforementioned active ingredients to be contained at a concentration effective for producing the brown adipocytes, and the concentration of the active ingredients can be appropriately determined by a person skilled in the art. The basal medium can be selected from known media or commercially available media. For example, general media MEM (minimum essential medium), DMEM (Dulbecco's modified eagle medium) and DMEM/F12, or a medium prepared by modifying them can be used as the basal medium.

Furthermore, known medium components aforementioned in the present specification, e.g. serum, proteins (albumin, transferrin, growth factor etc.), amino acids, saccharides, vitamins, fatty acids, antibiotics, or the like may be added to the medium.

Furthermore, substances effective for inducing differentiation into adipocytes aforementioned in the present specification, such as dexamethasone, insulin, 3-isobutyl-1-methylxanthine, rosiglitazone, glucocorticoid, and phosphodiesterase inhibitor may be added to the medium.

Furthermore, in the present invention, the brown adipocytes can also be produced from the somatic cells in a living body by administering the ALK5 inhibitor, and at least one inhibitor selected from a group consisting of the ALK6 inhibitor and the AMPK inhibitor to a living body. That is, the present invention provides a method for producing the brown adipocytes from the somatic cells in the living body, which includes administering the ALK5 inhibitor, and at least one inhibitor selected from the group consisting of the ALK6 inhibitor and the AMPK inhibitor to the living body. A preferable combination of inhibitors to be administered to the living body is as described in the present specification. Examples of the living body include humans, nonhuman mammals, and nonmammal animals (birds, reptiles, amphibians, fishes, etc.), and the human is particularly preferable. By administering the ALK5 inhibitor, and at least one inhibitor selected from the group consisting of the ALK6 inhibitor and the AMPK inhibitor to a specific site in a living body, the brown adipocytes can be produced from the somatic cells at the specific site.

B. Invention Related to Osteoblast

[1] A Method of Producing Osteoblast

The present invention relates to a method of producing osteoblasts, comprising a step c) of culturing a somatic cell in the presence of at least one inhibitor selected from a group consisting of an ALK5 inhibitor, a GSK3 inhibitor, an ALK2 inhibitor, and an ALK3 inhibitor, in the presence of a cAMP activator, and in the absence of an Erk inhibitor.

Preferably, the step c) is a step of culturing the somatic cell in the presence of the ALK2 inhibitor and the ALK3 inhibitor.

Preferably, the step c) is a step of culturing the somatic cell in the presence of at least one inhibitor selected from a group consisting of an ALK6 inhibitor and an AMPK inhibitor.

Particularly preferably, the step c) is a step of culturing the somatic cell in the presence of any of the followings:

(1) the ALK5 inhibitor, the GSK3 inhibitor, the ALK2 inhibitor, the ALK3 inhibitor, the ALK6 inhibitor, the AMPK inhibitor, and the cAMP activator, and in the absence of the Erk inhibitor;

(2) the ALK5 inhibitor, the GSK3 inhibitor, the ALK2 inhibitor, the ALK3 inhibitor, and the cAMP activator, and in the absence of the Erk inhibitor.

<Erk Inhibitor>

In the present invention, the somatic cells are cultured in the absence of the Erk inhibitor. The phrase "in the absence of the Erk inhibitor" refers to an aspect that there is there is substantially no Erk inhibitor, and includes not only a case that there is no Erk inhibitor but also a case that there is a trace amount of the Erk inhibitor. That is, the somatic cells are cultured in the absence of a substance inhibiting the Erk activity, e.g. an Erk signal-inhibiting means such as an anti-Erk antibody and an Erk inhibitor. Also, the somatic cells are cultured in the absence of a means for inhibiting an enzyme involved in Erk activation, e.g. an Erk kinase, an Erk kinase kinase, or the like.

<Inhibitor Having Two or More Inhibitory Actions>

As the aforementioned various inhibitors, an inhibitor having 2 or more inhibitory actions may be used.

For example, as the ALK2 inhibitor and the ALK3 inhibitor, LDN193189 inhibiting both ALK2 and ALK3 can be used, or dorsomorphin inhibiting ALK2, ALK3, ALK6 and AMPK can also be used. That is, culture of the somatic cells in the presence of the ALK2 inhibitor and the ALK3 inhibitor may be achieved by culturing the somatic cells in the presence of the LDN193189 and/or the dorsomorphin.

In addition, as the ALK6 inhibitor and the AMPK inhibitor, the dorsomorphin inhibiting both ALK6 and the AMPK can be used. That is, culture of the somatic cells in the presence of at least one inhibitor selected from a group consisting of the ALK6 inhibitor and the AMPK inhibitor may be achieved by culturing the somatic cells in the presence of the dorsomorphin.

<Other Preferable Conditions>

Although the culture condition is not particularly limited in the present invention, it is preferable to culture the somatic cells in the absence of growth factors and/or cytokines in step c). The phrase "in the absence of growth factors and/or cytokines" refers to an aspect that there are substantially no growth factors and/or cytokines, and includes not only a case that there is no growth factor and/or cytokine but also a case that there is a trace amount of growth factors and/or cytokines. An advantage of culturing the somatic cells in the absence of growth factors and/or cytokines is capability to produce osteoblasts at a low cost.

The growth factor is a general term for endogenous proteins capable of promoting proliferation and differentiation of specific cells in a living body. The cytokine refers to a protein secreted from immune cells, and serves information transmission in which any target cell is not specified. The cytokines include many cytokines involved in immunity and inflammation, and include some cytokines involved in cell proliferation, differentiation, cell death, or wound healing. Incidentally, some growth factors are included in cytokines, and conceptionally the growth factors and cytokines are not exclusive from each other.

The growth factor includes: Epidermal Growth Factor (EGF); Insulin-like Growth Factor (IGF); Transforming Growth Factor (TGF); Nerve Growth Factor (NGF); Vesicular Endothelial Growth Factor (VEGF); basic Fibroblast Growth Factor (bFGF); Hepatocyte Growth Factor (HGF); and the like.

Cytokines include: Interleukin (IL); (Interferon (IFN); leptin; and the like.

<Culture of Somatic Cell>

In the present invention, osteoblasts are produced from somatic cells. As a substance effective for differentiation induction into osteoblasts, dexamethasone, hydrocortisone, ascorbic acid, β-glycerophosphoric acid and the like are known. As a substance effective for differentiation induction into osteoblasts, for example, a substance commercially available as a differentiation inducer can be used. In the present invention, it is preferable to culture the somatic cells in the presence of the aforementioned substance.

<Osteoblast>

A cell population containing the osteoblasts can be obtained by the aforementioned method for producing the osteoblasts according to the present invention. The osteoblasts produced by the method for producing the osteoblasts according to the present invention are also within the scope of the present invention. The osteoblasts produced by the method according to the present invention may be terminally differentiated cells or precursor cells destined to differentiate into the osteoblasts.

The osteoblasts produced by the method according to the present invention can be detected, confirmed and separated using e.g. the morphological change of the cells, the characteristic property of the osteoblasts, and a specific marker.

As a specific marker for osteoblasts, a bone-specific alkaline phosphatase and an osteocalcin are known, which can be used as indicators to detect osteoblasts. In addition, since the osteoblasts have a property of depositing calcium on the outside of the cells, the osteoblasts can also be detected by staining the extracellular calcium through von Kossa staining or alizarin red staining.

The specific marker can be detected by using a quarantine method (detection by antibodies), meanwhile the protein molecules may be detected by quantifying an amount of its mRNAs. An antibody capable of recognizing a specific marker of the osteoblasts is also useful for isolating and purifying the osteoblasts obtained by the method according to the present invention.

The osteoblasts produced by the method according to the present invention are useful e.g. for regenerative medicine for complementing cells of which the number is decreased or the functionality is lowered in a living body. A tissue prepared by using the osteoblasts produced by the method according to the present invention alone or in combination with other cells or substrates (biopolymers etc.) can also be used for treatment. The osteoblasts produced by the method according to the present invention can be used to produce a pharmaceutical composition for tissue repair or the like.

When the osteoblast is used as a pharmaceutical composition, the composition should be formulated into a pharmaceutical preparation in a form suitable for administration to an individual e.g. by mixing the osteoblast with a pharmaceutically acceptable carrier in accordance with a conventional method. The carrier can include distilled water for injection, which is made isotonic by adding physiological saline, glucose and other adjuvants (e.g. D-sorbitol, D-mannitol, sodium chloride, etc.). Furthermore, a buffer (e.g. phosphate buffer, a sodium acetate buffer), an analgesic (e.g. benzalkonium chloride, procaine hydrochloride, etc.), a stabilizer (e.g. human serum albumin, polyethylene glycol, etc.), a preservative, an antioxidant, and the like may be blended.

Furthermore, the osteoblast can be made into a composition combined with other cells and components effective for functionality exertion and bioadhesiveness improvement of the osteoblast.

Furthermore, the osteoblasts produced by the method according to the present invention can also be used for screening a drug candidate compound capable of acting on the osteoblast and for evaluating safety of the drug candidate compound. Since the present invention can provide a large amount of osteoblasts in one operation, a reproducible study result can be obtained with no influence from the difference in lot of the cells.

[2] Compositions

The present invention further relates to a composition containing at least one inhibitor selected from a group consisting of an ALK5 inhibitor, a GSK3 inhibitor, an ALK2 inhibitor, and an ALK3 inhibitor, and a cAMP activator.

Preferably, the composition according to the present invention contains at least the ALK2 inhibitor and the ALK3 inhibitor.

Preferably, the composition according to the present invention further contains at least one inhibitor selected from a group consisting of an ALK6 inhibitor and an AMPK inhibitor.

Specific examples of the composition according to the present invention include compositions containing any of the following combinations:

(1) the ALK5 inhibitor, the GSK3 inhibitor, the ALK2 inhibitor, the ALK3 inhibitor, the ALK6 inhibitor, the AMPK inhibitor, and the cAMP activator;

(2) the ALK5 inhibitor, the GSK3 inhibitor, the ALK2 inhibitor, the ALK3 inhibitor, and the cAMP activator.

Specific examples and preferable examples of the above-mentioned activators and inhibitors have been already described herein.

The composition according to the present invention can be used as a composition for producing the osteoblasts from the somatic cells. The composition according to the present invention can also be used as a medium for producing the osteoblasts from the somatic cells.

The medium used for producing the osteoblasts from the somatic cells can be exemplified by a medium prepared by adding at least one inhibitor selected from a group consisting of the ALK5 inhibitor, the GSK3 inhibitor, the ALK2 inhibitor and the ALK3 inhibitor, and the cAMP activator as active ingredients to a basal medium prepared by mixing components necessary for cell culture. It is only necessary for the aforementioned active ingredients to be contained at a concentration effective for producing the osteoblasts, and the concentration of the active ingredients can be appropriately determined by a person skilled in the art. The basal medium can be selected from known media or commercially available media. For example, general media MEM (minimum essential medium), DMEM (Dulbecco's modified eagle medium) and DMEM/F12, or a medium prepared by modifying them can be used as the basal medium.

Furthermore, known medium components aforementioned in the present specification, e.g. serum, proteins (albumin, transferrin, growth factor etc.), amino acids, saccharides, vitamins, fatty acids, antibiotics, or the like may be added to the medium.

Furthermore, substances effective for inducing differentiation into osteoblasts aforementioned in the present specification, such as dexamethasone, hydrocortisone, ascorbic acid, and β-glycerophosphoric acid may be added to the medium.

For the method and the composition according to the present invention, a case may be excluded in which a medium prepared by adding a commercially available osteoblast differentiation inducer (Osteoblast-Inducer Reagent; Takara Bio Inc.) to a D-MEM (High Glucose) with L-Glutamate, Phenol Red and Sodium Pyruvate (Wako Pure Chemical Industries, Ltd.) containing SB-431524 (final concentration: 2 μmol/L), LDN-193189 (final concentration: 1 μmol/L), CHIR99021 (final concentration: 1 μmol/L), pifithrin-α (final concentration: 5 μmol/L) and forskolin (final concentration: 7.5 μmol/L) (1 mL of ascorbic acid, 200 μL of hydrocortisone, 2 mL of β-glycerophosphoric acid were added per 100 mL of the medium) is used.

For the method and the composition according to the present invention, a case may be excluded in which a medium prepared by adding the osteoblast differentiation inducer to the D-MEM containing SB-431524, LDN-193189, CHIR99021, pifithrin-α and forskolin.

For the method and the composition according to the present invention, a case may be excluded in which a medium prepared by adding the osteoblast differentiation inducer to a medium containing SB-431524, LDN-193189, CHIR99021, pifithrin-α and forskolin.

Furthermore, in the present invention, the osteoblasts can also be produced from the somatic cells in a living body by administering at least one inhibitor selected from a group consisting of the ALK5 inhibitor, the GSK3 inhibitor, the ALK2 inhibitor and the ALK3 inhibitor and the cAMP activator to a living body. That is, the present invention provides a method for producing the osteoblasts from the somatic cells in the living body, which includes administering at least one inhibitor selected from a group consisting of the ALK5 inhibitor, the GSK3 inhibitor, the ALK2 inhibitor and the ALK3 inhibitor and the cAMP activator to the living body. A preferable combination of inhibitors to be administered to the living body is as described in the present specification. Examples of the living body include humans, nonhuman mammals, and nonmammal animals (birds, reptiles, amphibians, fishes, etc.), and the human is particularly preferable. By administering at least one inhibitor selected from a group consisting of the ALK5 inhibitor, the GSK3 inhibitor, the ALK2 inhibitor and the ALK3 inhibitor and the cAMP activator to a specific site in a living body, the osteoblasts can be produced from the somatic cells at the specific site.

C. Invention Related to Chondrocyte

[1] A Method of Producing Chondrocyte

The present invention relates to a method of producing chondrocytes, comprising a step d) of culturing a somatic cell in the presence of at least one inhibitor selected from a group consisting of a cAMP activator, an ALK5 inhibitor, an ALK2 inhibitor, an ALK3 inhibitor, and a GSK3 inhibitor, in the absence of an Erk inhibitor, and in the absence of at least one inhibitor selected from a group consisting of an ALK6 inhibitor and an AMPK inhibitor.

Preferably, the step d) is a step of culturing the somatic cell in the presence of at least the ALK2 inhibitor and the ALK3 inhibitor.

Preferably, the step d) is a step of culturing the somatic cell in the presence of the cAMP activator, the ALK5 inhibitor, the ALK2 inhibitor, the ALK3 inhibitor, and the GSK3 inhibitor, in the absence of the Erk inhibitor, and in the absence of the ALK6 inhibitor and the AMPK inhibitor.

<ALK6 Inhibitor and AMPK Inhibitor>

In the present invention, the somatic cells are cultured in the absence of at least one inhibitor selected from the group consisting of the ALK6 inhibitor and the AMPK inhibitor.

The phrase "in the absence of at least one inhibitor selected from the group consisting of the ALK6 inhibitor and the AMPK inhibitor" refers to an aspect that there is there is substantially no at least one inhibitor selected from the group consisting of the ALK6 inhibitor and the AMPK inhibitor, and includes not only a case that there is none of at least one selected from the group consisting of the ALK6 inhibitor and the AMPK inhibitor but also a case that there is a trace amount of at least one inhibitor selected from the group consisting of the ALK6 inhibitor and the AMPK inhibitor.

In one example of the present invention, the somatic cells can be cultured in the absence of the aforementioned ALK6 inhibitor or AMPK inhibitor.

<Erk Inhibitor>

In the present invention, the somatic cells are cultured in the absence of the Erk inhibitor. The phrase "in the absence of the Erk inhibitor" refers to an aspect that there is there is substantially no Erk inhibitor, and includes not only a case that there is no Erk inhibitor but also a case that there is a trace amount of the Erk inhibitor. That is, the somatic cells are cultured in the absence of a substance inhibiting the Erk activity, e.g. an Erk signal-inhibiting means such as an anti-Erk antibody and an Erk inhibitor. Also, the somatic cells are cultured in the absence of a means for inhibiting an enzyme involved in Erk activation, e.g. an Erk kinase, an Erk kinase kinase, or the like.

<Inhibitor Having Two or More Inhibitory Actions>

As the aforementioned various inhibitors, an inhibitor having 2 or more inhibitory actions may be used.

For example, as the ALK2 inhibitor and the ALK3 inhibitor, LDN193189 inhibiting both ALK2 and ALK3 can be used.

<Culture of Somatic Cell>

In the present invention, chondrocytes are produced from somatic cells. As a substance effective for differentiation induction into chondrocytes, insulin, ascorbic acid, ascorbic acid-2-phosphate, hydrocortisone, TGF-β (transforming growth factor-β), dexamethasone and the like are known. As a substance effective for differentiation induction into chondrocytes, for example, a substance commercially available as a differentiation inducer can be used. In the present invention, it is preferable to culture the somatic cells in the presence of the aforementioned substance.

<Chondrocyte>

A cell population containing the chondrocytes can be obtained by the aforementioned method for producing the chondrocytes according to the present invention. The chondrocytes produced by the method for producing the chondrocytes according to the present invention are also within the scope of the present invention. The chondrocytes produced by the method according to the present invention may be terminally differentiated cells or precursor cells destined to differentiate into the chondrocytes.

The chondrocytes produced by the method according to the present invention can be detected, confirmed and separated using e.g. the morphological change of the cells, the characteristic property of the chondrocytes, and a specific marker.

Since the chondrocytes contain acidic mucopolysaccharides such as dermatan sulfate and chondroitin sulfate, the chondrocytes can be detected by staining cells with Alcian Blue used for dyeing acidic mucopolysaccharides In addition, the chondrocytes can be detected by Safranin O staining known as a cartilage tissue-staining method. Also, type II collagen and aggrecan which are highly expressed in chondrocytes are specific markers useful for confirming the chondrocytes.

The specific marker can be detected by using a quarantine method (detection by antibodies), meanwhile the protein molecules may be detected by quantifying an amount of its mRNAs. An antibody capable of recognizing a specific marker of the chondrocytes is also useful for isolating and purifying the chondrocytes obtained by the method according to the present invention.

The chondrocytes produced by the method according to the present invention are useful e.g. for regenerative medicine for complementing cells of which the number is decreased or the functionality is lowered in a living body. A tissue prepared by using the chondrocytes produced by the method according to the present invention alone or in combination with other cells or substrates (biopolymers etc.) can also be used for treatment. For example, a tissue prepared by combining the chondrocytes with a scaffolding substance (extracellular matrix component etc.) can be transplanted into a patient. The chondrocytes produced by the method according to the present invention can be used to produce a pharmaceutical composition for tissue repair or the like. For example, the chondrocytes may be administered to a patient for the purpose of treating joint injury associated with trauma and aging, and joint disease, or relieving their symptoms.

When the chondrocyte is used as a pharmaceutical composition, the composition should be formulated into a pharmaceutical preparation in a form suitable for administration to an individual e.g. by mixing the chondrocyte with a pharmaceutically acceptable carrier in accordance with a conventional method. The carrier can include distilled water for injection, which is made isotonic by adding physiological saline, glucose and other adjuvants (e.g. D-sorbitol, D-mannitol, sodium chloride, etc.). Furthermore, a buffer (e.g. phosphate buffer, a sodium acetate buffer), an analgesic (e.g. benzalkonium chloride, procaine hydrochloride, etc.), a stabilizer (e.g. human serum albumin, polyethylene glycol, etc.), a preservative, an antioxidant, and the like may be blended.

Furthermore, the chondrocyte can be made into a composition combined with other cells and components effective for functionality exertion and bioadhesiveness improvement of the chondrocyte.

Furthermore, the chondrocytes produced by the method according to the present invention can also be used for screening a drug candidate compound capable of acting on the chondrocytes and for evaluating safety of the drug candidate compound. Since the present invention can provide a large amount of chondrocytes in one operation, a reproducible study result can be obtained with no influence from the difference in lot of the cells.

[2] Composition

The present invention further relates to a composition for producing chondrocytes from a somatic cell, containing at least one inhibitor selected from a group consisting of a cAMP activator, an ALK5 inhibitor, an ALK2 inhibitor, an ALK3 inhibitor, and a GSK3 inhibitor. Preferably, the composition according to the present invention contains at least the ALK2 inhibitor and the ALK3 inhibitor.

The present invention further relates to a composition containing a cAMP activator, an ALK5 inhibitor, an ALK2 inhibitor, an ALK3 inhibitor, and a GSK3 inhibitor, and preferably, the composition is for producing chondrocytes from the somatic cell.

Specific examples and preferable examples of the above-mentioned activators and inhibitors have been already described herein.

The composition according to the present invention can be used as a composition for producing the chondrocytes from the somatic cells. The composition according to the present invention can also be used as a medium for producing the chondrocytes from the somatic cells.

The medium used for producing the chondrocytes from the somatic cells can be exemplified by a medium prepared by adding at least one inhibitor selected from a group consisting of the cAMP activator, the ALK5 inhibitor, the ALK2 inhibitor, the ALK3 inhibitor and the GSK3 inhibitor as active ingredients to a basal medium prepared by mixing components necessary for cell culture. It is only necessary for the aforementioned active ingredients to be contained at a concentration effective for producing the chondrocytes, and the concentration of the active ingredients can be appropriately determined by a person skilled in the art. The basal medium can be selected from known media or commercially available media. For example, general media MEM (minimum essential medium), DMEM (Dulbecco's modified eagle medium) and DMEM/F12, or a medium prepared by modifying them can be used as the basal medium.

Furthermore, known medium components aforementioned in the present specification, e.g. serum, proteins (albumin, transferrin, growth factor etc.), amino acids, saccharides, vitamins, fatty acids, antibiotics, or the like may be added to the medium.

Furthermore, substances effective for inducing differentiation into chondrocytes aforementioned in the present specification, such as insulin, ascorbic acid, ascorbic acid-2-phosphate, hydrocortisone, TGF-β (transforming growth factor-β), and dexamethasone may be added to the medium.

For the method and the composition according to the present invention, a case may be excluded in which a D-MEM, High Glucose, Pyruvate (Thermo Fisher Scientific, Inc.) containing SB-431524 (final concentration: 2 μmol/L), LDN-193189 (final concentration: 1 μmol/L), CHIR99021 (final concentration: 1 μmol/L), pifthrin-α (final concentration: 5 μmol/L), Forskolin (final concentration: 7.5 μmol/L), Insulin-Transferrin-Selenium (final concentration: 1%), ascorbic acid-2-phosphate (final concentration: 50 μg/ml), dexamethasone (final concentration: 100 μmol/L), TGF-β3 (final concentration: 10 ng/ml), L-proline (final concentration: 40 μg/ml), and Antibiotic-Antimycotic (Thermo Fisher Scientific, Inc., final concentration: 1×) is used.

For the method and the composition according to the present invention, a case may be excluded in which the D-MEM containing SB-431524, LDN-193189, CHIR99021, pifthrin-α, forskolin, Insulin-Transferrin-Selenium, ascorbic acid-2-phosphate, dexamethasone, TGF-β, L-proline, and Antibiotic-Antimycotic (Thermo Fisher Scientific, Inc.) is used.

For the method and the composition according to the present invention, a case may be excluded in which a medium containing SB-431524, LDN-193189, CHIR99021, pifthrin-α, forskolin, Insulin-Transferrin-Selenium, ascorbic acid-2-phosphate, dexamethasone, TGF-β3, L-proline, and Antibiotic-Antimycotic (Thermo Fisher Scientific, Inc.) is used.

Furthermore, in the present invention, the chondrocytes can also be produced from the somatic cells in a living body by administering at least one inhibitor selected from a group consisting of the cAMP activator, the ALK5 inhibitor, the ALK2 inhibitor, the ALK3 inhibitor and the GSK3 inhibitor to a living body. That is, the present invention provides a method for producing the chondrocytes from the somatic cells in the living body, which includes administering at least one inhibitor selected from a group consisting of the cAMP activator, the ALK5 inhibitor, the ALK2 inhibitor, the ALK3 inhibitor and the GSK3 inhibitor to the living body. A preferable combination of inhibitors to be administered to the living body is as described in the present specification. Examples of the living body include humans, nonhuman mammals, and nonmammal animals (birds, reptiles, amphibians, fishes, etc.), and the human is particularly preferable. By administering at least one inhibitor selected from a group consisting of the cAMP activator, the ALK5 inhibitor, the ALK2 inhibitor, the ALK3 inhibitor and the GSK3 inhibitor to a specific site in a living body, the chondrocytes can be produced from the somatic cells at the specific site.

D. Invention Related to Neural Cell

[1] A Method of Producing Neural Cell

The present invention relates to a method of producing neural cells, comprising a step e) of culturing a somatic cell in the presence of at least one inhibitor selected from a group consisting of an ALK6 inhibitor and an AMPK inhibitor.

Preferably, the step e) is a step of culturing the somatic cell in the presence of the ALK6 inhibitor and the AMPK inhibitor.

Preferably, the step e) is a step of culturing the somatic cell in the presence of at least one activator and/or inhibitor selected from a group consisting of a cAMP activator, an ALK2 inhibitor, an ALK3 inhibitor, an ALK5 inhibitor, a GSK3 inhibitor and an Erk inhibitor.

Particularly preferably, the step e) is a step of culturing the somatic cell in the presence of any of the followings:

(1) the ALK6 inhibitor, the AMPK inhibitor, the cAMP activator, the ALK2 inhibitor, the ALK3 inhibitor, the ALK5 inhibitor, the GSK3 inhibitor, and the Erk inhibitor;

(2) the ALK6 inhibitor, the AMPK inhibitor, the ALK2 inhibitor, the ALK3 inhibitor, the ALK5 inhibitor, the GSK3 inhibitor, and the Erk inhibitor;

(3) the ALK6 inhibitor, the AMPK inhibitor, the cAMP activator, the ALK2 inhibitor, the ALK3 inhibitor, the ALK5 inhibitor, and the Erk inhibitor;

(4) the ALK6 inhibitor, the AMPK inhibitor, the cAMP activator, the ALK2 inhibitor, the ALK3 inhibitor, the ALK5 inhibitor, and the GSK3 inhibitor.

<Inhibitor Having Two or More Inhibitory Actions>

As the aforementioned various inhibitors, an inhibitor having 2 or more inhibitory actions may be used.

For example, as the ALK2 inhibitor and the ALK3 inhibitor, LDN193189 inhibiting both ALK2 and ALK3 can be used, or dorsomorphin inhibiting ALK2, ALK3, ALK6 and AMPK can also be used. That is, culture of the somatic cells in the presence of at least one inhibitor selected from the ALK2 inhibitor and the ALK3 inhibitor may be achieved by culturing the somatic cells in the presence of the LDN193189 and/or the dorsomorphin.

In addition, as the ALK6 inhibitor and the AMPK inhibitor, the dorsomorphin inhibiting both ALK6 and the AMPK can be used. That is, culture of the somatic cells in the presence of at least one inhibitor selected from a group consisting of the ALK6 inhibitor and the AMPK inhibitor may be achieved by culturing the somatic cells in the presence of the dorsomorphin.

<Other Preferable Conditions>

Although the culture condition is not particularly limited in the present invention, it is preferable to culture the somatic cells in the absence of growth factors and/or cytokines in step e). The phrase "in the absence of growth factors and/or cytokines" refers to an aspect that there are substantially no growth factors and/or cytokines, and includes not only a case that there is no growth factor and/or cytokine but also a case that there is a trace amount of growth factors and/or cytokines. An advantage of culturing the somatic cells in the absence of growth factors and/or cytokines is capability to produce neural cells at a low cost.

The growth factor is a general term for endogenous proteins capable of promoting proliferation and differentiation of specific cells in a living body. The cytokine refers to a protein secreted from immune cells, and serves information transmission in which any target cell is not specified. The cytokines include many cytokines involved in immunity and inflammation, and include some cytokines involved in cell proliferation, differentiation, cell death, or wound healing. Incidentally, some growth factors are included in cytokines, and conceptionally the growth factors and cytokines are not exclusive from each other.

The growth factor includes: Epidermal Growth Factor (EGF); Insulin-like Growth Factor (IGF); Transforming Growth Factor (TGF); Nerve Growth Factor (NGF); Vesicular Endothelial Growth Factor (VEGF); basic Fibroblast Growth Factor (bFGF); Hepatocyte Growth Factor (HGF); and the like.

Cytokines include: Interleukin (IL); (Interferon (IFN); leptin; and the like.

<Culture of Somatic Cell>

In the present invention, neural cells are produced from somatic cells. As a substance effective for differentiation induction into neural cells, Brain-Derived Neurotrophic Factor (BDNF), Glial cell-Derived Neurotrophic Factor (GDNF), cAMP, ascorbic acid, ascorbic acid-2-phosphate and the like are known. As a substance effective for differentiation induction into neural cells, for example, a substance commercially available as a differentiation inducer can be used. In the present invention, the somatic cells may be cultured in the presence of the aforementioned substance.

<Neural Cell>

A cell population containing the neural cells can be obtained by the aforementioned method for producing the neural cells according to the present invention. The neural cells produced by the method for producing the neural cells according to the present invention are also within the scope of the present invention. The neural cells produced by the method according to the present invention are exemplified by, but not limited to, neurons, glial cells (astrocytes, oligodendrocytes, microglia), Schwann cells and the like. The neural cells may be the above-mentioned terminally differentiated cells or precursor cells destined to differentiate into the neural cells.

The neural cells produced by the method according to the present invention can be confirmed e.g. by morphological change of the cell. Since the neural cells take a characteristic morphology depending on the cell type, the presence of the neural cells can be confirmed by comparing morphologies of cells before and after the culture. Also, the neural cells can be confirmed by detecting molecules peculiar to the neural cells, e.g. enzymes, receptors, low molecular weight compounds or the like. Examples of the molecules peculiar to the neural cells include, but are not limited to, β3-tubulin, synapsin I, vesicular glutamate transporter (vGULT), microtubule-associated protein (MAP) 2, γ-aminobutyric acid (GABA), tyrosine hydroxylase, and the like.

The above-mentioned molecules can be detected by using a quarantine method (detection by antibodies), meanwhile the protein molecules may be detected by quantifying an amount of its mRNAs. An antibody capable of recognizing a molecule peculiar to the neural cells is also useful for isolating and purifying the neural cells obtained by the method according to the present invention.

For example, the neural cells produced by the method according to the present invention are useful for treating nervous system diseases. The nervous system diseases include, but are not limited to, spinal cord injury, cerebrovascular disorder (cerebral infarction etc.), Parkinson's disease, Alzheimer's disease, amyotrophic lateral sclerosis, and the like. The neural cells produced by the method according to the present invention can be used to produce a pharmaceutical composition for treating nervous system diseases.

When the neural cell is used as a pharmaceutical composition, the composition should be formulated into a pharmaceutical preparation in a form suitable for administration to an individual e.g. by mixing the neural cell with a pharmaceutically acceptable carrier in accordance with a conventional method. The carrier can include distilled water for injection, which is made isotonic by adding physiological saline, glucose and other adjuvants (e.g. D-sorbitol, D-mannitol, sodium chloride, etc.). Furthermore, a buffer (e.g. phosphate buffer, a sodium acetate buffer), an analgesic (e.g. benzalkonium chloride, procaine hydrochloride, etc.), a stabilizer (e.g. human serum albumin, polyethylene glycol, etc.), a preservative, an antioxidant, and the like may be blended.

Furthermore, the neural cell can be made into a composition combined with other cells and components effective for functionality exertion and bioadhesiveness improvement of the neural cell.

Furthermore, the neural cells produced by the method according to the present invention can also be used for screening a drug candidate compound capable of acting on the neural cell and for evaluating safety of the drug candidate compound. Since the present invention can provide a large amount of neural cells in one operation, a reproducible study result can be obtained with no influence from the difference in lot of the cells.

[2] Compositions

The present invention further relates to a composition for producing neural cells from a somatic cell, containing at least one inhibitor selected from a group consisting of an ALK6 inhibitor and an AMPK inhibitor. The composition may contain the ALK6 inhibitor and the AMPK inhibitor.

The present invention further relates to a composition containing at least one inhibitor selected from a group consisting of an ALK6 inhibitor and an AMPK inhibitor, and at least one activator and/or inhibitor selected from a group consisting of a cAMP activator, an ALK2 inhibitor, an ALK3 inhibitor, an ALK5 inhibitor, a GSK3 inhibitor, and an Erk inhibitor.

Specific examples of the composition according to the present invention include compositions containing any of the following combinations:

(1) the ALK6 inhibitor, the AMPK inhibitor, the cAMP activator, the ALK2 inhibitor, the ALK3 inhibitor, the ALK5 inhibitor, the GSK3 inhibitor, and the Erk inhibitor;

(2) the ALK6 inhibitor, the AMPK inhibitor, the ALK2 inhibitor, the ALK3 inhibitor, the ALK5 inhibitor, the GSK3 inhibitor, and the Erk inhibitor;

(3) the ALK6 inhibitor, the AMPK inhibitor, the cAMP activator, the ALK2 inhibitor, the ALK3 inhibitor, the ALK5 inhibitor, and the Erk inhibitor;

(4) the ALK6 inhibitor, the AMPK inhibitor, the cAMP activator, the ALK2 inhibitor, the ALK3 inhibitor, the ALK5 inhibitor, and the GSK3 inhibitor.

Specific examples and preferable examples of the above-mentioned activators and inhibitors have been already described herein.

The composition according to the present invention can be used as a composition for producing the neural cells from the somatic cells. The composition according to the present invention can also be used as a medium for producing the neural cells from the somatic cells.

The medium used for producing the neural cells from the somatic cells can be exemplified by a medium prepared by adding at least one inhibitor selected from a group consisting of the ALK6 inhibitor and the AMPK inhibitor as active ingredients to a basal medium prepared by mixing components necessary for cell culture. It is only necessary for the aforementioned active ingredients to be contained at a concentration effective for producing the neural cells, and the concentration of the active ingredients can be appropriately determined by a person skilled in the art. The basal medium can be selected from known media or commercially available media. For example, general media MEM (minimum essential medium), DMEM (Dulbecco's modified eagle medium) and DMEM/F12, or a medium prepared by modifying them can be used as the basal medium.

Furthermore, known medium components aforementioned in the present specification, e.g. serum, proteins (albumin, transferrin, growth factor etc.), amino acids, saccharides, vitamins, fatty acids, antibiotics, or the like may be added to the medium.

Furthermore, substances effective for inducing differentiation into neural cells aforementioned in the present specification, such as Brain-Derived Neurotrophic Factor (BDNF), Glial cell-Derived Neurotrophic Factor (GDNF), cAMP, ascorbic acid, and ascorbic acid-2-phosphate may be added to the medium.

Furthermore, in the present invention, the neural cells can also be produced from the somatic cells in a living body by administering at least one inhibitor selected from a group consisting of the ALK6 inhibitor and the AMPK inhibitor to a living body. That is, the present invention provides a method for producing the neural cells from the somatic cells in the living body, which includes administering at least one inhibitor selected from a group consisting of the ALK6 inhibitor and the AMPK inhibitor to the living body. A preferable combination of inhibitors to be administered to the living body is as described in the present specification. Examples of the living body include humans, nonhuman mammals, and nonmammal animals (birds, reptiles, amphibians, fishes, etc.), and the human is particularly preferable. By administering at least one inhibitor selected from a group consisting of the ALK6 inhibitor and the AMPK inhibitor to a specific site in a living body, the neural cells can be produced from the somatic cells at the specific site.

E. Invention Related to Cardiomyocyte

[1] A Method of Producing Cardiomyocyte

The present invention relates to a method of producing cardiomyocytes, comprising a step f) of culturing a somatic cell in the presence of at least one inhibitor selected from a group consisting of an ALK6 inhibitor and an AMPK inhibitor, and in the presence of at least one inhibitor selected from a group consisting of a cAMP activator, an ALK5 inhibitor, and an Erk inhibitor.

Preferably, the step f) is a step of culturing the somatic cell in the presence of the ALK6 inhibitor and the AMPK inhibitor, and in the presence of a cAMP activator, an ALK5 inhibitor, and an Erk inhibitor.

Preferably, the step f) is a step of culturing the somatic cell in the presence of at least one inhibitor selected from a group consisting of an ALK2 inhibitor and an ALK3 inhibitor.

Preferably, the step f) is a step of culturing the somatic cell in the presence of a GSK3 inhibitor.

Particularly preferably, the step f) is a step of culturing the somatic cell in the presence of any of the followings:

(1) the ALK6 inhibitor, the AMPK inhibitor, the cAMP activator, the ALK2 inhibitor, the ALK3 inhibitor, the ALK5 inhibitor, the GSK3 inhibitor, and the Erk inhibitor;

(2) the ALK6 inhibitor, the AMPK inhibitor, the cAMP activator, the ALK2 inhibitor, the ALK3 inhibitor, the ALK5 inhibitor, and the Erk inhibitor.

<Inhibitor Having Two or More Inhibitory Actions>

As the aforementioned various inhibitors, an inhibitor having 2 or more inhibitory actions may be used.

For example, as the ALK2 inhibitor and the ALK3 inhibitor, LDN93189 inhibiting both ALK2 and ALK3 can be used, or dorsomorphin inhibiting ALK2, ALK3, ALK6 and AMPK can also be used. That is, culture of the somatic cells in the presence of at least one inhibitor selected from the ALK2 inhibitor and the ALK3 inhibitor may be achieved by culturing the somatic cells in the presence of the LDN193189 and/or the dorsomorphin.

In addition, as the ALK6 inhibitor and the AMPK inhibitor, the dorsomorphin inhibiting both ALK6 and the AMPK can be used. That is, culture of the somatic cells in the presence of at least one inhibitor selected from a group consisting of the ALK6 inhibitor and the AMPK inhibitor may be achieved by culturing the somatic cells in the presence of the dorsomorphin.

<Other Preferable Conditions>

Although the culture condition is not particularly limited in the present invention, it is preferable to culture the somatic cells in the absence of the ALK4 inhibitor in step f). The phrase "in the absence of the ALK4 inhibitor" refers to an aspect that there are substantially no ALK4 inhibitors, and includes not only a case that there are no ALK4 inhibitors but also a case that there is a trace amount of the ALK4 inhibitors. The ALK4 is a subfamily member of receptor serine/threonine kinases, and mediates signaling through activin. The ALK4 mediates Nodal signaling in the presence of Cripto at a developmental stage of a vertebrate.

The SB431542 (Wako Pure Chemical Industries, Ltd.) exemplarily described as one of the ALK5 inhibitors in the present specification also has an ALK4 inhibitory action, but in the present invention, preferably a compound having no ALK4 inhibitory action is used as the ALK5 inhibitor.

<Culture of Somatic Cell>

In the present invention, cardiomyocytes are produced from somatic cells. As a substance effective for differentiation induction into cardiomyocytes, 5-azacytidine, TGF-β (Transforming growth factor-β), angiotensin-II, BMP-2 (Bone Morphogenetic Protein 2), dimethylsulfoxide (DMSO) and the like are known. As a substance effective for differentiation induction into cardiomyocytes, for example, a substance commercially available as a differentiation inducer can be used. In the present invention, it is preferable to culture the somatic cells in the presence of the aforementioned substance.

<Cardiomyocyte>

A cell population containing the cardiomyocytes can be obtained by the aforementioned method for producing the cardiomyocytes according to the present invention. The cardiomyocytes produced by the method for producing the cardiomyocytes according to the present invention are also within the scope of the present invention. The cardiomyocytes produced by the method according to the present invention may be terminally differentiated cells or precursor cells destined to differentiate into the cardiomyocytes.

The cardiomyocytes produced by the method according to the present invention can be detected, confirmed and separated using e.g. the morphological change of the cells, the characteristic property of the cardiomyocytes, and a specific marker.

The cardiomyocytes have a characteristic of autonomous beating which is absent in other cells, and can be distinguished from other cells by microscopic observation. In addition, examples of the specific marker for the cardiomyocytes include, but are not limited to, cardiac troponin C (cTnT), α myosin heavy chain, a actin, and the like.

The specific marker can be detected by using a quarantine method (detection by antibodies), meanwhile the protein molecules may be detected by quantifying an amount of its mRNAs. An antibody capable of recognizing a specific marker of the cardiomyocytes is also useful for isolating and purifying the cardiomyocytes obtained by the method according to the present invention.

The cardiomyocytes produced by the method according to the present invention can be used e.g. for the purpose of repairing tissues. The cardiomyocytes produced by the method according to the present invention can be used to produce a pharmaceutical composition for the tissue repair or the like. As a means for treating heart diseases such as heart failure and myocardial infarction, a production method for cardiomyocytes and a transplantation method for cardiomyocytes have been developed. For example, since a myocardial sheet formed by laminating cardiomyocytes, and endothelial cells or the like has excellent therapeutic effect and bioadhesiveness, the myocardial sheet is expected to be usable for treating severe heart failure.

When the cardiomyocyte is used as a pharmaceutical composition, the composition should be formulated into a pharmaceutical preparation in a form suitable for administration to an individual e.g. by mixing the cardiomyocyte with a pharmaceutically acceptable carrier in accordance with a conventional method. The carrier can include distilled water for injection, which is made isotonic by adding physiological saline, glucose and other adjuvants (e.g. D-sorbitol, D-mannitol, sodium chloride, etc.). Furthermore, a buffer (e.g. phosphate buffer, a sodium acetate buffer), an analgesic (e.g. benzalkonium chloride, procaine hydrochloride, etc.), a stabilizer (e.g. human serum albumin, polyethylene glycol, etc.), a preservative, an antioxidant, and the like may be blended.

Furthermore, the cardiomyocyte can be made into a composition combined with other cells and components effective for functionality exertion and bioadhesiveness improvement of the cardiomyocyte.

Furthermore, the cardiomyocytes produced by the method according to the present invention can also be used for screening a drug candidate compound capable of acting on the cardiomyocyte and for evaluating safety of the drug candidate compound. The cardiomyocytes are an important tool for evaluating cardiotoxicity of drug candidate compounds. Since the present invention can provide a large amount of cardiomyocytes in one operation, a reproducible study result can be obtained with no influence from the difference in lot of the cells.

[2] Compositions

The present invention further relates to a composition containing at least one inhibitor selected from a group consisting of an ALK6 inhibitor and an AMPK inhibitor, as well as a cAMP activator, an ALK5 inhibitor, and an Erk inhibitor.

Preferably, the composition according to the present invention contains the ALK6 inhibitor, the AMPK inhibitor, the cAMP activator, the ALK5 inhibitor, and the Erk inhibitor.

Preferably, the composition according to the present invention further contains at least one inhibitor selected from a group consisting of an ALK2 inhibitor and an ALK3 inhibitor.

Preferably, the composition according to the present invention further contains a GSK3 inhibitor.

Specific examples of the composition according to the present invention include compositions containing any of the following combinations:

(1) the ALK6 inhibitor, the AMPK inhibitor, the cAMP activator, the ALK2 inhibitor, the ALK3 inhibitor, the ALK5 inhibitor, the GSK3 inhibitor, and the Erk inhibitor;

(2) the ALK6 inhibitor, the AMPK inhibitor, the cAMP activator, the ALK2 inhibitor, the ALK3 inhibitor, the ALK5 inhibitor, and the Erk inhibitor.

Specific examples and preferable examples of the abovementioned activators and inhibitors have been already described herein.

The composition according to the present invention can be used as a composition for producing the cardiomyocytes from the somatic cells. The composition according to the present invention can also be used as a medium for producing the cardiomyocytes from the somatic cells.

The medium used for producing the cardiomyocytes from the somatic cells can be exemplified by a medium prepared by adding at least one inhibitor selected from a group consisting of the ALK6 inhibitor and the AMPK inhibitor, as well as the cAMP activator, the ALK5 inhibitor and the Erk inhibitor as active ingredients to a basal medium prepared by mixing components necessary for cell culture. It is only necessary for the aforementioned active ingredients to be contained at a concentration effective for producing the cardiomyocytes, and the concentration of the active ingredients can be appropriately determined by a person skilled in the art. The basal medium can be selected from known media or commercially available media. For example, general media MEM (minimum essential medium), DMEM (Dulbecco's modified eagle medium) and DMEM/F12, or a medium prepared by modifying them can be used as the basal medium.

Furthermore, known medium components aforementioned in the present specification, e.g. serum, proteins (albumin, transferrin, growth factor etc.), amino acids, saccharides, vitamins, fatty acids, antibiotics, or the like may be added to the medium.

Furthermore, substances effective for inducing differentiation into cardiomyocytes aforementioned in the present specification may be added to the medium.

Furthermore, in the present invention, the cardiomyocytes can also be produced from the somatic cells in a living body by administering at least one inhibitor selected from a group consisting of the ALK6 inhibitor and the AMPK inhibitor, as well as the cAMP activator, the ALK5 inhibitor and the Erk inhibitor to a living body. That is, the present invention provides a method for producing the cardiomyocytes from the somatic cells in the living body, which includes administering at least one inhibitor selected from a group consisting of the ALK6 inhibitor and the AMPK inhibitor, as well as the cAMP activator, the ALK5 inhibitor and the Erk inhibitor to the living body. A preferable combination of inhibitors to be administered to the living body is as described in the present specification. Examples of the living body include humans, nonhuman mammals, and nonmammal animals (birds, reptiles, amphibians, fishes, etc.), and the human is particularly preferable. By administering at least one inhibitor selected from a group consisting of the ALK6 inhibitor and the AMPK inhibitor, as well as the cAMP activator, the ALK5 inhibitor and the Erk inhibitor to a specific site in a living body, the cardiomyocytes can be produced from the somatic cells at the specific site.

EXAMPLES

Hereinafter, the present invention will be specifically described with reference to Examples, but the present invention is not limited to the scope of Examples.

Example A: Brown Adipocyte Production 1

<Induction of Brown Adipocyte from Human Fibroblast>
(1) Human Fibroblast

As materials, human fibroblasts were purchased from DS Pharma Biomedical Co., Ltd. The fibroblasts were derived from a skin of a 38-year-old human.

(2) Direct Induction from Human Fibroblast to Brown Adipocyte

The human fibroblasts were seeded on 35 mm dishes at a rate of $8 \times 10^4$ cells per a dish, and cultured in DMEM high glucose medium (Wako Pure Chemical Industries, Ltd.) to which 10% fetal bovine serum (FBS), 100 U/ml penicillin and 100 μg/ml streptomycin under a condition at 37° C. and 5% $CO_2$ were added for 2 days. Note that the DMEM refers to a Dulbecco's Modified Eagle Medium.

The medium in the dish containing the human fibroblasts was exchanged to a DMEM (high glucose) with L-Glutamine Phenol Red, Sodium Pyruvate (Wako Pure Chemical Industries, Ltd.) containing insulin (final concentration: 10 μg/ml), dexamethasone (final concentration: 2.5 μmol/L), 3-isobutyl-1-methylxanthine (final concentration: 0.5 mmol/L), rosiglitazone (final concentration: 1 μmol/L), and a low molecular weight compound added according to Table 1. Subsequently, the cells were cultured under the condition at 37° C. and 5% $CO_2$ while exchanging the medium to the medium having the same composition every 3 days. The details of the compounds listed in Table 1 are as aforementioned in the present specification.

TABLE 1

(The unit of numerical value in the table is μmol/L)

| Chemical compound | function | Ex. 1 | Ex. 2 | Ex. 3 | Ex. 4 | Ex. 5 | Ex. 6 | Comp. Ex. 1 | Comp. Ex. 2 | Comp. Ex. 3 |
|---|---|---|---|---|---|---|---|---|---|---|
| Forskolin | cAMP activator | — | 7.5 | 7.5 | 7.5 | 7.5 | — | 7.5 | 7.5 | — |
| SB431542 | TGF inhibitor (ALK5 inhibition) | 2 | 2 | 7 | 2 | 2 | 2 | 2 | — | — |
| LDN193189 | BMP inhibitor (ALK2/3 inhibition) | 1 | — | 1 | 1 | 1 | 1 | 1 | 1 | — |
| Dorsomorphin | BMP inhibitor (ALK2/3/6 inhibition) AMPK inhibitor | 1 | 1 | 1 | 1 | 1 | 1 | — | 1 | — |
| CHIR99021 | GSK3 β inhibitor | 1 | 1 | — | 1 | — | — | 1 | 1 | — |
| PD0325901 | Erk inhibitor | 1 | 1 | 1 | — | — | — | 1 | 1 | — |

(3) Evaluation of Brown Adipocyte

As a result of culturing the human fibroblasts in accordance with the above (2), adipocyte-like cells appeared 6 days after the onset of culturing. Twenty-one days after the onset of culturing, the cells were immobilized with 2% paraformaldehyde, and then immunostained. For staining, an anti-UCP1 antibody (ab10983, Abcam PLC; diluted 400-fold) was used. The results are shown in FIG. 1. In the figure, the upper pictures present the results of immunostaining, blue represents the results of staining the nuclears with DAPI (4',6-diamidino-2-phenylindole), and green represents the results of staining the UCP-1. Note that, since the photograph images are monochrome in FIG. 1, blue and green are not displayed, but in the original photograph images of FIG. 1, green and blue are displayed. The lower pictures show phase-contrast microscopic images in the same visual fields as of the upper pictures.

As shown in FIG. 1, the brown adipocyte marker UCP-1 positive cells appear by culturing with a plurality of low molecular weight compounds. Furthermore, it is shown that, the TGF inhibitor SB431542, and among the BMP inhibitor, dorsomorphin having an ALK 6 inhibitory ability and an AMPK inhibitory ability are preferable for differentiation into brown adipocytes.

Example B: Brown Adipocyte Production 2

Abbreviations of the compounds are as below.
G: CHIR99021
M: PD0325901
S: SB431542

L: LDN193189
F: Forskolin
D: Dorsomorphin
Ro: Rosiglitazone

Note that 5C means a combination of the 5 compounds G, M, S, L and F. 5CD means the 5C plus D. 5CDRo means the 5C plus D and Ro. 5CDRo-G means the 5CDRo excluding G. These abbreviations also applies to the other notations.

<Method>
(Cell Culture)

Human skin fibroblasts were purchased from DS Pharma Biomedical Co., Ltd. Cell information is described in the following table.

TABLE 2

| Catalog # | Lot # | Passage number | BMI | Age | Gender | Site | abbreviation |
|---|---|---|---|---|---|---|---|
| NHDF | DFMF112410B | 4 | unknown | 0 | Male | Prepuce | Neo |
| NHDF | DFM090214A | 3 | 23.1 | 38 | Male | Abdomen | DC38 |
| NHDF | 3101601.2 | 2 | unknown | 49 | Female | Chest | PC49 |

About $1.5 \times 10^5$ cells were seeded on a 35 mm dish containing a high-glucose DMEM medium (11995-065, Gibco, MA, USA) to which 10% fetal bovine serum (FBS) (HyClone, Utah, USA) and penicillin/streptomycin (Gibco) were added.

(Direct Transformation from Human Fibroblast to Brown Adipocyte)

After each of the human fibroblasts reached 80-90% confluence, the medium was changed to start direct transformation into the brown adipocyte. The adipocyte medium for use was prepared by adding an additive reagent containing ascorbic acid, biotin, pantothenic acid, triiodothyronine, octanoic acid, insulin, dexamethasone, IBLMX (3-isobutyl-1-methylxanthine), FBS and penicillin/streptomycin (MK425, Takara Bio Inc.) to a high-glucose DMEM medium (043-30085, Wako Pure Chemical Industries, Ltd.). All low molecular weight compounds were purchased from Wako Pure Chemical Industries, Ltd., and added to the adipocyte medium at the following final concentrations: CHIR99021 (1 µM), PD0325901 (1 µM), SB431542 (2 µM), LDN193189 (1 µM), forskolin (7.5 µM), pifithrin-α (5 µM), dorsomorphin (1 µM), and rosiglitazone (1 µM). The human fibroblasts were cultured in the adipocyte medium containing each of the indicated compounds for 3 weeks. The medium was exchanged every 3 days. The cells were cultured in the adipocyte medium containing only rosiglitazone (1 µM) for another week to mature chemically-induced brown adipocyte-like cells.

(Immunostaining)

Immunocytochemistry was performed in accordance with a previous report (Dai P, et al. J Clin Biochem Nutr. 2015; 56 (3): 166-70). First, the cells were fixed with 2% paraformaldehyde (NACALAI TESQUE). The cells were washed with phosphate buffered saline (PBS) 3 times, and then incubated in PBS containing 0.1% Triton X-100 for 10 minutes. Subsequently, the cells were blocked with PBS containing 3% of skim milk at room temperature for 1 hour. A UCP-1 antibody (ab10983, Abcam PLC, Cambridge, UK) was diluted with a blocking solution in a ratio of 1/500. The cells were incubated with antibodies at 4° C. overnight. The cells were washed with PBS 3 times, and then incubated with Alexa Fluor 488 Donkey anti-Rabbit IgG (A-21206, Thermo Fisher Scientific, Inc.) at room temperature for 2 hours. Cell nuclei were stained with a DAPI solution (Dojindo Molecular Technologies, Inc.). All images were acquired using a fluorescence microscope (Axio Vert. A1, Carl Zeiss, Oberkochen, Germany). Mitochondria were stained with MitoTracker® Red CMXRos (Thermo Fisher Scientific, Inc.).

(RNA Isolation and QRT-PCR)

For the purpose of quantifying gene expression, the whole RNA was extracted from the fibroblasts treated with each compound, using the RNeasy Mini kit (QIAGEN N.V). As a control, a fibroblast was cultured in parallel, in the adipocyte medium. The cells were treated with 0.1 µM, 1 µM and 10 µM isoproterenol or forskolin for 3 hours or 6 hours, and then the whole RNA was extracted from the brown adipocytes induced with the compound and the control cell. The whole RNA was reversely transferred with ReverTraAce® PCR RT Master Mix with gDNA Remover (TOYOBO CO., LTD.), and then subjected to a real-time PCR analysis using Power SYBR Green PCR Master Mix (Thermo Fisher Scientific, Inc.). For one standard, 3 reactions were carried out under the following condition: 40 cycles of reactions at 95° C. for 10 minutes, at 95° C. for 15 seconds, and at 60° C. for 60 seconds. All results were standardized by the amount of the Tbp mRNA. Primers used in the QRT-PCR are shown in the following table.

TABLE 3

| Gene | Sense primer | Antisense primer |
|---|---|---|
| Tbp | ACTACGGGTTA TCACCTGTGAG (sequence number 1) | GTGCAGGAGTA GGCCACATTAC (sequence number 2) |
| Ucp1 | TCTACGACAC GGTCCAGGAG (sequence number 3) | GAATACTGCCA CTCCTCCAGTC (sequence number 4) |
| Ckmt1a | AGCAGGAATG GCTCGAGAC (sequence number 5) | ATCCTCCTCAT TCACCCAGATC (sequence number 6) |
| Cited 1 | TGGCACCTCA CCTGCGAAG (sequence number 7) | GCAGAATGGC CACTGCTTTG (sequence number 8) |
| Col1a2 | TCGCACATGC CGTGACTTG (sequence number 9) | CCCATTTCTGC ACATGTACCAG (sequence number 10) |
| Fabp4 | GCCAGGAATTT GACGAAGTCA (sequence number 11) | CCCATTTCTGC ACATGTACCAG (sequence number 12) |
| Adipo Q | CTGGTGAGAAG GGTGAGAAAG (sequence number 13) | GTTTCACCGAT GTCTCCCTTAG (sequence number 14) |
| Ppar γ | TGGAATTAGATG ACAGCGACTTG (sequence number 15) | CTTCAATGGGC TTCACATTCAG (sequence number 16) |

(Measurement of Oxygen Consumption Rate)

For the purpose of measuring an oxygen consumption rate (OCR) of mitochondria, 3 different fibroblasts of subjects aged 0, 38 and 49 were directly transformed with a combination of compounds (5CDRo-GM; i.e. SB431542, LDN193189, forskolin, dorsomorphin, rosiglitazone) on a 96-well plate for 3 weeks. As a control, a fibroblast was cultured in parallel, in the adipocyte medium. For the purpose of maturation, these cells were cultured in the adipocyte medium containing only rosiglitazone for another week. The cells were incubated in a non-$CO_2$ incubator at 37° C. for 1 hour, then the oxygen consumption rate in each well containing the brown adipocyte induced with the compound was analyzed using XF96 Extracellular Flux Analyzer (Seahorse Bioscience Inc., Billerica, Mass.) in accordance with the user instruction. During the analysis, oligomycin, FCCP (carbonyl cyanide 4-(trifluoromethoxy) phenyl hydrazone) and antimycin A/rotenone were added to each well through an injection device so that their final concentrations were 2 μM, 0.25 μM, and 0.5 μM respectively.

<Result>

(Identification of Compound for Direct Transformation from Human Fibroblast to Adipocyte)

As shown in FIG. 2, direct transformation was promoted by combinations of the 5CDRo. When excluding CHIR99021 and PD0325901 from the combinations of the 5CDRo (CHIR99021, PD0325901, SB431542, LDN193189, forskolin, dorsomorphin, rosiglitazone), a transformation efficiency and lipid droplet formation were improved (FIG. 2).

Expression of adipocyte-specific genes was quantified in the cells treated with the combinations of the compounds. Compared to the control, the expression of the Fabp4 was increased in the cells treated with the combinations of the compounds (FIG. 3).

(Increase of Ucp1 Expression and Mitochondria Generation in Compound-Induced Adipocyte-Like Cell)

Cells were incubated with each combination of the compounds for 3 weeks, then compounds other than rosiglitazone were removed from the adipocyte medium, and the cells were incubated for 1 week. Thereby, maturation of the adipocyte-like cells was clearly promoted, and the amount of the lipid droplet was increased.

The 5CDRo-G (PD0325901, SB431542, LDN193189, forskolin, dorsomorphin, rosiglitazone) efficiently produced brown adipocytes (FIG. 4 and the following table).

FIG. 5 shows results of excluding one of compounds other than CHIR99021 from the 5CDRo-G. When the PD0325901 or LDN193189 was excluded, a production efficiency of the adipocyte-like cells was maximized. Combinations including 3 compounds, such as "forskolin, dorsomorphin and SB431542", "forskolin, LDN193189 and SB431542", "dorsomorphin, LDN193189 and SB431542" and "dorsomorphin, PD032590 and SB431542", and the like made the fibroblasts to be efficiently transformed into the adipocyte-like cells (FIG. 6). Also in the case of 2 or less compounds, direct transformation was observed (FIG. 7 and FIG. 8).

The efficiencies of transformation into the adipocyte-like cells with various combinations of the compounds were evaluated from the results shown in FIG. 4 to FIG. 8, and the results are shown in the following table. Note that FIG. 4 to FIG. 8 show the results of observing the results of immunostaining with a phase contrast microscope, and the efficiency was comprehensively judged from the states of the cells. In the table, the larger the number of the marks "+" is, the higher the transformation efficiency is. For example, the mark "++++" indicates that almost all of the fibroblasts were transformed into brown adipocytes. The mark "−" indicates that the fibroblasts were not transformed into brown adipocytes.

TABLE 4

| Combination | Efficiency |
| --- | --- |
| 6 chemical compounds | |
| 5 CDRo (GMSLDFRo) | + |
| 5 chemical compounds | |
| 5 CDRo-G (MSLDFRo) | +++ |
| 5 CDRo-M (GSLDFRo) | + |
| 5 CDRo-S (GMLDFRo) | + |
| 5 CDRo-L (GMSDFRo) | ++ |
| 5 CDRo-D (GMSLFRo) | ++ |
| 5 CDRo-F (GMSLDRo) | + |
| 4 chemical compounds | |
| 5 CDRo-GM (SLDFRo) | ++++ |
| 5 CDRo-GS (MLDFRo) | + |
| 5 CDRo-GL (MSDFRo) | ++++ |
| 5 CDRo-GD (MSLFRo) | +++ |
| 5 CDRo-GF (MSLDRo) | +++ |

TABLE 5

| Combination | Efficiency |
| --- | --- |
| 3 chemical compounds | |
| FDLRo | ++ |
| FDMRo | ++ |
| FDSRo | +++ |
| FLMRo | + |
| FLSRo | +++ |
| FMSRo | ++ |
| DLMRo | ++ |
| DLSRo | +++ |
| DMSRo | +++ |
| LMSRo | ++ |
| 2 chemical compounds | |
| DFRo | + |
| DLRo | + |
| DMRo | ++ |
| DSRo | ++ |
| FLRo | ++ |
| FMRo | ++ |
| FSRo | +++ |
| LSRo | +++ |
| MSRo | ++ |
| 1 chemical compound | |
| GRo | − |
| MRo | + |
| LRo | + |
| SRo | ++ |
| DRo | + |
| FRo | + |
| Ro only | − |

For the purpose of confirming the usefulness of direct transformation with the 5CDRo-GM (SB431542, LDN193189, forskolin, dorsomorphin, rosiglitazone), 3 fibroblasts derived from human adults and newborn (aged 38, 49, and 0) were tested. After maturation by rosiglitazone on the last week, all the fibroblasts produced adipocyte-like cells (FIG. 9 A to C).

Immunocytochemical analysis was also carried out to analyze the protein expression and the UCP1 cellular localization. As a result, most of the adipocyte-like cells were proven to be UCP-1 positive, indicating that the adipocyte-like cells had the characteristics of the brown adipocytes.

Furthermore, staining of the UCP-1 was sufficiently overlapped with the increased mitochondrial signals. The oil red staining confirmed that the adipocyte-like cells had a large amount of lipid droplet (FIG. 10).

(Induction of Human Brown Adipocyte Specific Gene Expression in Compound-Induced Brown Adipocyte)

For the purpose of characterizing gene expression of the compound-induced brown adipocytes, a plurality of marker genes specific to the human brown adipose tissues were quantified by QRT-PCR. The human-derived fibroblasts of 3 subjects aged 0 (newborn), 38, and 49 were cultured together with the 5CDRo-GM for 3 weeks, and then matured with rosiglitazone for 1 week.

The Ucp1 mRNA was induced in all fibroblasts, compared to the control without the compounds (FIG. 11 A). Expressions of the Ckmt1 (mitochondrial creatine kinase) and the Cited1 (human brown adipocyte marker) were induced in all fibroblasts (FIG. 11 A). The Col1a2 (one of fibroblast markers) decreased by about 40% to 80%, indicating that the cell fate changed from the fibroblast to the brown adipocyte (FIG. 11 B). Regarding all of the fibroblasts, expressions of fat generation/differentiation markers Fabp4, AdipoQ, and Pparγ were increased in the brown adipocytes induced with the compounds (FIG. 11 C). Note that the 5CD in FIG. 11 means the 5CDRo, and the 5CD-MG is synonymous with the 5CDRo-MG.

(Functional β Adrenergic Receptor Signal for Thermogenesis in Compound-Induced Brown Adipocyte)

Thermogenesis through the Ucp1 is regulated through the sympathetic nervous system and the 3 adrenergic receptor signaling pathway in the brown adipocytes. For the purpose of evaluating the thermogenetic ability in the crown adipocytes induced with the compounds, the brown adipocytes were treated with isoproterenols (β adrenergic receptor agonist) at 3 different concentrations for 3 hours or 6 hours, and then the Ucp1 mRNA was quantified (FIG. 12 A). The Ucp1 mRNA was slightly increased through the 3-hour treatment, and markedly increased through the 6 hour-treatment about 4 to 5 times as much as the untreated cells. For the purpose of confirming whether the Ucp1 was induced through the increase of the intracellular cAMP level, the cells were treated with forskolin at 3 different concentrations for 3 hours or 6 hours (FIG. 12 B). The Ucp1 expression in the cells treated for 6 hours was more enhanced than that in the cells treated for 3 hours, when comparing with the untreated cells. In contrast, there was no significant change in expression of other human brown adipocyte-specific genes Ckmt1 and Cited1. The above results suggest that the increased expression is specific to thermogenic genes such as Ucp1 (FIGS. 12 C and D). Also, the above results indicate that the thermogenic gene induction can respond to the β adrenergic receptor signaling pathway.

(Increase of Oxygen Consumption Rate (OCR) in Compound-Induced Brown Adipocyte)

For the purpose of demonstrating that the increase of mitochondria in the compound-induced brown adipocytes was associated with the increased oxygen consumption rate, brown adipocytes derived from different human fibroblasts were analyzed by a Flux analyzer. The OCR value was typically changed by adding a perturbation reagent during measurement, and the brown adipocyte derived from the fibroblast of the 38-year old subject exhibited a higher OCR than that of the control (FIG. 13 A). The brown adipocytes derived from the other fibroblasts also exhibited increased OCR (FIGS. 13 B and C). The above results showed that oxidative metabolism in mitochondria was accelerated and activated in the brown adipocytes induced with the compounds.

Example C: Osteoblast Production 1

<Induction of Osteoblast from Human Fibroblast>
(1) Human Fibroblast

As materials, human fibroblasts were purchased from DS Pharma Biomedical Co., Ltd. The fibroblasts were derived from a skin of a 38-year-old human.

(2) Direct Induction from Human Fibroblast to Osteoblast

The human fibroblasts were seeded on 35 mm dishes at a rate of $5 \times 10^4$ cells per a dish, and cultured in DMEM medium (Gibco) to which 10% fetal bovine serum (FBS), 100 U/ml penicillin and 100 µg/ml streptomycin under a condition at 37° C. and 5% $CO_2$ were added to become confluent. Note that the DMEM refers to a Dulbecco's Modified Eagle Medium.

The medium in the dish containing the human fibroblasts was exchanged to a RPMI1640 with L-Glutamine and Phenol Red (Wako Pure Chemical Industries, Ltd.) containing an osteoblast-inducer reagent (Takara Bio Inc.), and a low molecular weight compound added according to Table 1. Subsequently, the cells were cultured under the condition at 37° C. and 5% $CO_2$ while exchanging the medium to the medium having the same composition every 3 days. The details of the compounds listed in Table 6 are as aforementioned in the present specification.

TABLE 6

(The unit of numerical value in the table is 1 µmol/L)

| Chemical compound | function | Ex. 1 | Ex. 2 | Comp. Ex. 1 | Comp. Ex. 2 | Comp. Ex. 3 | Comp. Ex. 4 | Comp. Ex. 5 | Comp. Ex. 6 | Comp. Ex. 7 |
|---|---|---|---|---|---|---|---|---|---|---|
| Forskolin | cAMP activator | 7.5 | 7.5 | 7.5 | — | 7.5 | 7.5 | 7.5 | — | — |
| SB431542 | TGF inhibitor (ALK5 inhibition) | 2 | 2 | 2 | 2 | — | 2 | 2 | 2 | — |
| LDN193189 | BMP inhibitor (ALK2/3 inhibition) | 1 | 1 | 1 | 1 | 1 | — | 1 | 1 | — |
| Dorsomorphin | BMP inhibitor (ALK2/3/6 inhibition) AMPK inhibitor | 1 | — | 1 | 1 | 1 | 1 | 1 | 1 | — |

TABLE 6-continued (The unit of numerical value in the table is 1 μmol/L)

| Chemical compound | function | Ex. 1 | Ex. 2 | Comp. Ex. 1 | Comp. Ex. 2 | Comp. Ex. 3 | Comp. Ex. 4 | Comp. Ex. 5 | Comp. Ex. 6 | Comp. Ex. 7 |
|---|---|---|---|---|---|---|---|---|---|---|
| CHIR99021 | GSK3 β inhibitor | 1 | 1 | 1 | 1 | 1 | 1 | — | 1 | — |
| PD0325901 | Erk inhibitor | — | — | 1 | 1 | 1 | 1 | 1 | — | — |

(3) Evaluation of Osteoblast

As a result of culturing human fibroblasts according to the above (2), osteoblast-like cells appeared 7 days after the onset of culturing. Twenty-one days after the onset of culturing, the cells were subjected to von Kossa staining according to a conventional method, to evaluate the presence or absence of calcium deposition. The results are shown in FIG. 14. In the figure, the upper pictures show the results of von Kossa staining, and the lower pictures present phase-contrast microscopic images in the same visual fields as of the upper pictures.

As shown in FIG. 14, it can be seen in Example 1 and Example 2 that cells appear in which calcium deposition can be recognized by von Kossa staining. Furthermore, it is shown that, among the cAMP activator forskolin, the TGF inhibitor SB431542 and the BMP inhibitor, the LDN193189 having the ALK2/3 inhibitory ability but not the ALK6 inhibitory ability and the AMPK inhibitory ability, and the GSK-3β inhibitor CHIR99021 are important for differentiation of the osteoblasts, and the Erk inhibitor PD325901 should not be added.

Example D: Chondrocyte Production 1

<Induction of Chondrocyte from Human Fibroblast>
(1) Human Fibroblast

As materials, human fibroblasts were purchased from DS Pharma Biomedical Co., Ltd. The fibroblasts were derived from a skin of a 38-year-old human.

(2) Direct Induction from Human Fibroblast to Chondrocyte

The human fibroblasts were seeded on 35 mm dishes at a rate of $5\times10^4$ cells per a dish, and cultured in DMEM medium (Gibco) to which 10% fetal bovine serum (FBS), 100 U/ml penicillin and 100 μg/ml streptomycin under a condition at 37° C. and 5% $CO_2$ were added to become confluent. Note that the DMEM refers to a Dulbecco's Modified Eagle Medium.

The medium in the dish containing the human fibroblasts was exchanged to a DMEM (Thermo Fisher Scientific, Inc.) containing Insulin-Transferrin-Selenium (Thermo Fisher Scientific, Inc., final concentration: 1%), ascorbic acid-2-phosphate (Wako Pure Chemical Industries, Ltd., final concentration: 50 μg/ml), dexamethasone (Wako Pure Chemical Industries, Ltd., final concentration: 0.1 μM), TGF-β3 (PeproTech, Inc., final concentration: 10 ng/ml), L-proline (Nacalai Tesque, final concentration: 40 μg/ml), Antibiotic-Antimycotic (Thermo Fisher Scientific, Inc., final concentration: 1×), and a low molecular weight compound added according to Table 1. Subsequently, the cells were cultured under the condition at 37° C. and 5% $CO_2$ while exchanging the medium to the medium having the same composition every 3 days. The details of the compounds listed in Table 7 are as aforementioned in the present specification.

TABLE 7

(The unit of numerical value in the table is μmol/L)

| Chemical compound | function | Ex. 1 | Comp. Ex. 1 | Comp. Ex. 2 | Comp. Ex. 3 | Comp. Ex. 4 | Comp. Ex. 5 | Comp. Ex. 6 | Comp. Ex. 7 |
|---|---|---|---|---|---|---|---|---|---|
| Forskolin | cAMP activator | 7.5 | 7.5 | — | 7.5 | 7.5 | 7.5 | 7.5 | — |
| SB431542 | TGF inhibitor (ALK5 inhibition) | 2 | 2 | 2 | 2 | 2 | 2 | — | — |
| LDN193189 | BMP inhibitor (ALK2/3 inhibition) | 1 | 1 | 1 | 1 | — | 1 | 1 | — |
| Dorsomorphin | BMP inhibitor (ALK2/3/6 inhibition) AMPK inhibitor | — | 1 | 1 | 1 | 1 | 1 | 1 | — |
| CHIR99021 | GSK3 β inhibitor | 1 | 1 | 1 | — | 1 | 1 | 1 | — |
| PD0325901 | Erk inhibitor | — | 1 | 1 | 1 | 1 | — | 1 | — |

(3) Evaluation of Chondrocyte

As a result of culturing human fibroblasts according to Example (2), chondrocyte-like cells appeared 7 days after the onset of culturing. Twenty-one days after the onset of culturing, the cells were subjected to Alcian Blue staining according to a conventional method, to evaluate the presence or absence of acid polysaccharides which are a cartilage matrix. The results are shown in FIG. 15. In the figure, the upper pictures show the results of Alcian Blue staining, and the lower pictures present phase-contrast microscopic images in the same visual fields as of the upper pictures.

As shown in FIG. 15, it can be seen in Example 1 that cells appear in which production of acid polysaccharides can be recognized by Alcian Blue staining. Furthermore, it is shown that, among the cAMP activator forskolin, the TGF inhibitor SB431542 and the BMP inhibitor, addition of the LDN193189 having the ALK⅔ inhibitory and the GSK-3β inhibitor CHIR99021 is important for differentiation of the chondrocytes, and it is desirable that, among the BMP inhibitors, dorsomorphin having the ALK6 inhibitory ability and the AMPK inhibitory ability and the Erk inhibitor PD325901 are not contained.

Example E: Neural Cell Production 1

<Induction of Neural Cell from Human Fibroblast>
(1) Human Fibroblast

As materials, human fibroblasts were purchased from DS Pharma Biomedical Co., Ltd. The fibroblasts were derived from a skin of a 38-year-old human.

(2) Direct Induction from Human Fibroblast to Neural Cell

The human fibroblasts were seeded on 35 mm dishes at a rate of $8 \times 10^4$ cells per a dish, and cultured in DMEM high glucose medium (Wako Pure Chemical Industries, Ltd.) to which 10% fetal bovine serum (FBS), 100 U/ml penicillin and 100 μg/ml streptomycin under a condition at 37° C. and 5% $CO_2$ were added for 2 days. Note that the DMEM refers to a Dulbecco's Modified Eagle Medium.

The medium in the dish containing the human fibroblasts was exchanged to a DMEM (high glucose) with a medium containing 0.5% N-2 supplement (Thermo Fisher Scientific, Inc.), 1% B-27 supplement (Thermo Fisher Scientific, Inc.), 50% DMEM/F12, 50% Neurobasal Medium (Thermo Fisher Scientific, Inc.), and a low molecular weight compound added according to Table 1. Subsequently, the cells were cultured under the condition at 37° C. and 5% $CO_2$ while exchanging the medium to the medium having the same composition every 3 days. The details of the compounds listed in Table 8 are as aforementioned in the present specification.

TABLE 8

(The unit of numerical value in the table is μmol/L)

| Chemical compound | function | Ex. 1 | Ex. 2 | Ex. 3 | Ex. 4 | Ex. 5 | Comp. Ex. 1 |
|---|---|---|---|---|---|---|---|
| Forskolin | cAMP activator | 7.5 | — | 7.5 | 7.5 | 7.5 | 7.5 |
| SB431542 | TGF inhibitor (ALK5 inhibition) | 2 | 2 | 2 | 2 | 2 | 2 |
| LDN193189 | BMP inhibitor (ALK2/3 inhibition) | 1 | 1 | — | 1 | 1 | 1 |
| Dorsomorphin | BMP inhibitor (ALK2/3/6 inhibition) AMPK inhibitor | 1 | 1 | 1 | 1 | 1 | — |
| CHIR99021 | GSK3 β inhibitor | 1 | 1 | 1 | — | 1 | 1 |
| PD0325901 | Erk inhibitor | 1 | 1 | 1 | 1 | — | 1 |

(3) Evaluation of Neural Cell

As a result of culturing the human fibroblasts in accordance with the above (2), nerve-like projection structures were recognized 5 days after the onset of culturing. Fourteen days after the onset of culturing, the cells were immobilized with 2% paraformaldehyde, and then immunostained. For staining, an anti-βIII-tubulin antibody (MMS-435P, Covance; diluted 1000-fold) was used. The results are shown in FIG. 16. In the figure, the upper pictures present the results of immunostaining, blue represents the results of staining the nuclears with DAPI (4',6-diamidino-2-phenylindole), and green represents the results of staining the βIII-tubulin. The lower pictures show phase-contrast microscopic images in the same visual fields as of the upper pictures.

As shown in FIG. 16, the βIII-tubulin positive cells appear in Examples 1 to 5. Furthermore, it is shown that, among the BMP inhibitor, dorsomorphin having an ALK 6 inhibitory ability and an AMPK inhibitory ability is important for differentiation into neural cells.

Example F: Cardiomyocyte Production 1

<Induction of Cardiomyocyte from Human Fibroblast>
(1) Human Fibroblast

As materials, human fibroblasts were purchased from DS Pharma Biomedical Co., Ltd. The fibroblasts were derived from a skin of a 38-year-old human.

(2) Direct Induction from Human Fibroblast to Cardiomyocyte

The human fibroblasts were seeded on 35 mm dishes at a rate of $8 \times 10^4$ cells per a dish, and cultured in DMEM high glucose medium (Gibco) to which 10% fetal bovine serum (FBS), 100 U/ml penicillin and 100 μg/ml streptomycin under a condition at 37° C. and 5% $CO_2$ were added for 2 days. Note that the DMEM refers to a Dulbecco's Modified Eagle Medium.

The medium in the dish containing the human fibroblasts was exchanged to a DMEM (high glucose) with DMEM (High Glucose) with L-Glutamine Phenol Red, Sodium Pyruvate (Wako Pure Chemical Industries, Ltd.) containing 10% fetal bovine serum, 1% N-2 supplement (Thermo Fisher Scientific, Inc.), 2% B-27 supplement (Thermo Fisher Scientific, Inc.), 1×MEM non-essential amino acid (Thermo Fisher Scientific, Inc.), 0.1 mM 2-mercaptoethanol, 50 μg/ml penicillin, 100 μg/ml streptomycin, and a low molecular weight compound added according to Table 1. Subsequently, the cells were cultured under the condition at 37° C. and 5% $CO_2$ while exchanging the medium to the medium having the same composition every 3 days. The details of the compounds listed in Table 9 are as aforementioned in the present specification.

TABLE 9

(The unit of numerical value in the table is μmol/L)

| Chemical compound | function | Ex. 1 | Ex. 2 | Ex. 3 | Ex. 4 | Comp. Ex. 1 | Comp. Ex. 2 | Comp. Ex. 3 | Comp. Ex. 4 |
|---|---|---|---|---|---|---|---|---|---|
| Forskolin | cAMP activator | 7.5 | 7.5 | 7.5 | 7.5 | — | 7.5 | 7.5 | 7.5 |
| Repsox | TGF inhibitor (ALK5 inhibition) | 5 | 5 | 5 | 5 | 5 | — | 5 | 5 |
| LDN193189 | BMP inhibitor (ALK2/3 inhibition) | 1 | — | 1 | — | 1 | 1 | 1 | 1 |
| Dorsomorphin | BMP inhibitor (ALK2/3/6 inhibition) AMPK inhibitor | 1 | 1 | 1 | 1 | 1 | 1 | — | 1 |
| CHIR99021 | GSK3 β inhibitor | 1 | 1 | — | — | 1 | 1 | 1 | 1 |
| PD0325901 | Erk inhibitor | 1 | 1 | 1 | 1 | 1 | 1 | 1 | — |

(3) Evaluation of Cardiomyocyte

As a result of culturing the human fibroblasts in accordance with the above (2), shrinking or beating single cells or small cell masses were recognized 8 days after the onset of culturing. Twenty-one or more days after the onset of culturing, a large number of shrinking or beating cardiomyocyte-like masses were observed. Twenty-one days after the onset of culturing, the cells were immobilized with 2% paraformaldehyde, and then immunostained. For staining, an anti-cTnT antibody (ab10214, Abcam PLC; diluted 200-fold) was used. The results are shown in FIG. 17. In the figure, the upper pictures present the results of immunostaining, blue represents the results of staining the nuclears with DAPI (4',6-diamidino-2-phenylindole), and green represents the results of staining the cTnT. The lower pictures show phase-contrast microscopic images in the same visual fields as of the upper pictures.

As shown in FIG. 17, the cTnT positive cells appear in Examples 1 to 4. Furthermore, it is shown that, the cAMP activator forskolin, the TGF inhibitor Repsox, and among the BMP inhibitor, dorsomorphin having an ALK 6 inhibitory ability and an AMPK inhibitory ability, as well as the Erk inhibitor PD0325901 are important for differentiation into cardiomyocytes.

The invention claimed is:

1. A method of producing brown adipocytes, comprising a step a) of culturing a fibroblast as a starting material in the presence of an ALK5 inhibitor, an ALK6 inhibitor, an AMPK inhibitor, an ALK2 inhibitor, and an ALK3 inhibitor, and optionally in the further presence of a cAMP activator and/or an Erk inhibitor, wherein the inhibitors and the activator are in combination with a brown adipocyte differentiation induction medium, and in the absence of a GSK3 inhibitor, wherein brown adipocytes are produced.

2. The method of producing brown adipocytes according to claim 1, wherein the step a) is performed in the presence of one of the following combinations:
   (1) the ALK5 inhibitor, the ALK6 inhibitor, the AMPK inhibitor, the ALK2 inhibitor, the ALK3 inhibitor, and the cAMP activator;
   (2) the ALK5 inhibitor, the ALK6 inhibitor, the AMPK inhibitor, the ALK2 inhibitor, the ALK3 inhibitor, and the Erk inhibitor; and
   (3) the ALK5 inhibitor, the ALK6 inhibitor, the AMPK inhibitor, the ALK2 inhibitor, the ALK3 inhibitor, the cAMP activator, and the Erk inhibitor.

3. The method of producing brown adipocytes according to claim 1, wherein the step a) is performed in the absence of a p53 inhibitor.

4. The method of producing brown adipocytes according to claim 1, wherein the step a) is performed in the absence of components acting on histone.

5. The method of producing brown adipocytes according to claim 1, wherein the fibroblast is a human fibroblast.

6. A method of producing brown adipocytes, comprising a step a) of culturing a fibroblast as a starting material in the presence of an ALK5 inhibitor and dorsomorphin, and
   optionally in the further presence of a cAMP activator and/or an Erk inhibitor,
   wherein the inhibitors and the activator are in combination with a brown adipocyte differentiation induction medium, and
   in the absence of a GSK3 inhibitor, wherein brown adipocytes are produced.

7. A method of producing brown adipocytes, comprising a step a) of culturing a fibroblast as a starting material
   in the presence of an ALK5 inhibitor, an ALK6 inhibitor, an AMPK inhibitor, and LDN193189, and
   optionally in the further presence of a cAMP activator and/or an Erk inhibitor,
   wherein the inhibitors and the activator are in combination with a brown adipocyte differentiation induction medium, and
   in the absence of a GSK3 inhibitor, wherein brown adipocytes are produced.

8. The method of producing brown adipocytes according to claim 6, wherein the ALK5 inhibitor is SB431542.

9. The method of producing brown adipocytes according to claim 7, wherein the ALK5 inhibitor is SB431542.

* * * * *

SEQUENCE LISTING

```
<160> NUMBER OF SEQ ID NOS: 14

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 1
actacggggt tatcacctgt gag                                            23

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 2
gtgcaggagt aggccacatt ac                                             22

<210> SEQ ID NO 3
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      DNA

<400> SEQUENCE: 3
tctacgacac ggtccaggag                                                   20

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
gaatactgcc actcctccag tc                                                22

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
agcaggaatg gctcgagac                                                    19

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 6
atcctcctca ttcacccaga tc                                                22

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
tggcacctca cctgcgaag                                                    19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
gcagaatggc cactgctttg                                                   20

<210> SEQ ID NO 9
<211> LENGTH: 19
<212> TYPE: DNA
<213> ORGANISM: Artificial Sequence
<220> FEATURE:
```

```
<223> OTHER INFORMATION: Description of Artificial Sequence: Synthetic
      DNA

<400> SEQUENCE: 9
tcgcacatgc cgtgacttg                                                19

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 10
gatagcatcc atagtgcatc cttg                                          24

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 11
gccaggaatt tgacgaagtc a                                             21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 12
cccatttctg cacatgtacc ag                                            22

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 13
ctggtgagaa gggtgagaaa g                                             21

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 14
gtttcaccga tgtctccctt ag                                            22
```